United States Patent
Marks et al.

(10) Patent No.: US 12,270,074 B1
(45) Date of Patent: Apr. 8, 2025

(54) COMPOSITIONS AND METHODS FOR GENE EXPRESSION LIBRARY ANALYSIS

(71) Applicant: 10x Genomics, Inc., Pleasanton, CA (US)

(72) Inventors: Patrick J. Marks, San Francisco, CA (US); Michael Schnall-Levin, San Francisco, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 0 days.

(21) Appl. No.: 18/589,354

(22) Filed: Feb. 27, 2024

Related U.S. Application Data

(63) Continuation of application No. PCT/US2023/021925, filed on May 11, 2023.

(60) Provisional application No. 63/340,730, filed on May 11, 2022.

(51) Int. Cl.
| | |
|---|---|
| *C12Q 1/6869* | (2018.01) |
| *C12N 15/10* | (2006.01) |
| *C12Q 1/48* | (2006.01) |
| *C12Q 1/6874* | (2018.01) |

(52) U.S. Cl.
CPC ....... *C12Q 1/6869* (2013.01); *C12N 15/1086* (2013.01); *C12Q 1/485* (2013.01); *C12Q 1/6874* (2013.01)

(58) Field of Classification Search
CPC .... C12Q 1/6869; C12Q 1/485; C12Q 1/6874; C12Q 2531/125; C12Q 2543/10; C12Q 2565/102; C12N 15/1086
See application file for complete search history.

(56) References Cited

U.S. PATENT DOCUMENTS

| | | | |
|---|---|---|---|
| 4,318,846 A | 3/1982 | Khanna et al. | |
| 4,757,141 A | 7/1988 | Fung et al. | |
| 5,066,580 A | 11/1991 | Lee | |
| 5,091,519 A | 2/1992 | Cruickshank | |
| 5,151,507 A | 9/1992 | Hobbs et al. | |
| 5,188,934 A | 2/1993 | Menchen | |
| 5,366,860 A | 11/1994 | Bergot et al. | |
| 5,635,352 A | 6/1997 | Urdea et al. | |
| 5,688,648 A | 11/1997 | Mathies | |
| 5,695,940 A | 12/1997 | Drmanac et al. | |
| 5,800,996 A | 9/1998 | Lee et al. | |
| 5,847,162 A | 12/1998 | Lee et al. | |
| 5,990,479 A | 11/1999 | Weiss et al. | |
| 6,054,274 A | 4/2000 | Sampson et al. | |
| 6,207,392 B1 | 3/2001 | Weiss et al. | |
| 6,251,303 B1 | 6/2001 | Bawendi et al. | |
| 6,265,552 B1 | 7/2001 | Schatz | |
| 6,291,187 B1 | 9/2001 | Kingsmore et al. | |
| 6,306,597 B1 | 10/2001 | Macevicz | |
| 6,319,426 B1 | 11/2001 | Bawendi et al. | |
| 6,322,901 B1 | 11/2001 | Bawendi et al. | |
| 6,323,009 B1 | 11/2001 | Lasken et al. | |
| 6,344,329 B1 | 2/2002 | Lizardi et al. | |
| 6,368,801 B1 | 4/2002 | Faruqi | |
| 6,391,937 B1 | 5/2002 | Beuhler et al. | |
| 6,423,551 B1 | 7/2002 | Weiss et al. | |
| 6,426,513 B1 | 7/2002 | Bawendi et al. | |
| 6,444,143 B2 | 9/2002 | Bawendi et al. | |
| 6,534,266 B1 | 3/2003 | Singer | |
| 6,576,291 B2 | 6/2003 | Bawendi et al. | |
| 7,255,994 B2 | 8/2007 | Lao | |
| 7,345,159 B2 | 3/2008 | Ju et al. | |
| 7,473,767 B2 | 1/2009 | Dimitrov | |
| 7,534,991 B2 | 5/2009 | Miller et al. | |
| 7,544,794 B1 | 6/2009 | Benner | |
| 7,555,155 B2 | 6/2009 | Levenson et al. | |
| 7,566,537 B2 | 7/2009 | Balasubramanian et al. | |
| 7,632,641 B2 | 12/2009 | Dirks et al. | |
| 7,655,898 B2 | 2/2010 | Miller | |
| 7,721,721 B1 | 5/2010 | Kronengold et al. | |
| 7,893,227 B2 | 2/2011 | Wu et al. | |
| 7,910,304 B2 | 3/2011 | Drmanac | |
| 7,941,279 B2 | 5/2011 | Hwang et al. | |
| 7,956,171 B2 | 6/2011 | Siddiqi | |
| 7,989,166 B2 | 8/2011 | Koch et al. | |
| 8,034,923 B1 | 10/2011 | Benner et al. | |
| 8,071,755 B2 | 12/2011 | Efcavitch et al. | |
| 8,124,751 B2 | 2/2012 | Pierce et al. | |
| 8,133,672 B2 | 3/2012 | Bjornson et al. | |

(Continued)

FOREIGN PATENT DOCUMENTS

| | | |
|---|---|---|
| EP | 3702474 | 9/2020 |
| WO | WO 2013/119827 | 8/2013 |

(Continued)

OTHER PUBLICATIONS

Ke et al. "In situ sequencing for RNA analysis in preserved tissue and cells," Nature Methods (2013) 10(9):857-862.

(Continued)

*Primary Examiner* — Narayan K Bhat
(74) *Attorney, Agent, or Firm* — MORRISON & FOERSTER LLP

(57) ABSTRACT

Methods and compositions for analyzing a library comprising a plurality of amplicons comprising identifier sequences are provided, for example, a library of amplicons in a cell or tissue sample attached to a solid support. For example, amplicons are sequenced using a polymerase to incorporate a plurality of cognate nucleotides into the sequencing primer or an extension product thereof to generate a plurality of extension products.

20 Claims, 5 Drawing Sheets

Specification includes a Sequence Listing.

(56) References Cited

U.S. PATENT DOCUMENTS

| | | |
|---|---|---|
| 8,199,999 B2 | 6/2012 | Hoyt et al. |
| 8,257,954 B2 | 9/2012 | Clark et al. |
| 8,268,554 B2 | 9/2012 | Schallmeiner |
| 8,330,087 B2 | 12/2012 | Domenicali |
| 8,343,746 B2 | 1/2013 | Rank et al. |
| 8,415,102 B2 | 4/2013 | Geiss et al. |
| 8,431,691 B2 | 4/2013 | McKernan et al. |
| 8,460,865 B2 | 6/2013 | Chee et al. |
| 8,462,981 B2 | 6/2013 | Determan et al. |
| 8,481,258 B2 | 7/2013 | Church et al. |
| 8,519,115 B2 | 8/2013 | Webster et al. |
| 8,551,710 B2 | 10/2013 | Bernitz et al. |
| 8,632,975 B2 | 1/2014 | Vander Horn et al. |
| 8,658,361 B2 | 2/2014 | Wu et al. |
| 8,658,365 B2 | 2/2014 | Bjornson et al. |
| 8,703,461 B2 | 4/2014 | Peris et al. |
| 8,771,950 B2 | 7/2014 | Church et al. |
| 8,808,989 B1 | 8/2014 | Efcavitch et al. |
| 8,921,086 B2 | 12/2014 | Hanzel et al. |
| 8,986,926 B2 | 3/2015 | Ferree et al. |
| 9,201,063 B2 | 12/2015 | Sood et al. |
| 9,273,349 B2 | 3/2016 | Nguyen et al. |
| 9,279,155 B2 | 3/2016 | Bjornson et al. |
| 9,371,563 B2 | 6/2016 | Geiss et al. |
| 9,371,598 B2 | 6/2016 | Chee |
| 9,376,717 B2 | 6/2016 | Gao et al. |
| 9,399,798 B2 | 7/2016 | Stupi et al. |
| 9,453,258 B2 | 9/2016 | Kain et al. |
| 9,512,422 B2 | 12/2016 | Barnard et al. |
| 9,541,504 B2 | 1/2017 | Hoyt |
| 9,551,032 B2 | 1/2017 | Landegren et al. |
| 9,624,538 B2 | 4/2017 | Church et al. |
| 9,650,406 B2 | 5/2017 | Zhou et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,889,422 B2 | 2/2018 | Smith et al. |
| 9,909,167 B2 | 3/2018 | Samusik et al. |
| 9,951,385 B1 | 4/2018 | Vijayan et al. |
| 10,032,064 B2 | 7/2018 | Hoyt |
| 10,059,990 B2 | 8/2018 | Boyden et al. |
| 10,126,242 B2 | 11/2018 | Miller et al. |
| 10,138,509 B2 | 11/2018 | Church et al. |
| 10,179,932 B2 | 1/2019 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,545,075 B2 | 1/2020 | Deisseroth et al. |
| 10,550,429 B2 | 2/2020 | Harada et al. |
| 10,580,128 B2 | 3/2020 | Miller |
| 10,640,816 B2 | 5/2020 | Beechem et al. |
| 10,640,826 B2 | 5/2020 | Church et al. |
| 10,655,176 B2 | 5/2020 | Stromberg et al. |
| 10,669,569 B2 | 6/2020 | Gullberg et al. |
| 10,746,981 B2 | 8/2020 | Tomer et al. |
| 10,768,173 B1 | 9/2020 | Arslan et al. |
| 10,774,372 B2 | 9/2020 | Chee et al. |
| 10,774,374 B2 | 9/2020 | Frisén et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,829,814 B2 | 11/2020 | Fan et al. |
| 10,844,426 B2 | 11/2020 | Daugharthy et al. |
| 10,858,698 B2 | 12/2020 | Church et al. |
| 10,872,679 B2 | 12/2020 | Cai et al. |
| 10,964,001 B2 | 3/2021 | Miller |
| 10,982,280 B2 | 4/2021 | Arslan et al. |
| 11,078,520 B2 | 8/2021 | Church et al. |
| 11,085,072 B2 | 8/2021 | Church et al. |
| 11,174,281 B1 | 11/2021 | Graham et al. |
| 11,225,688 B2 | 1/2022 | Glezer et al. |
| 11,287,422 B2 | 3/2022 | Previte et al. |
| 11,293,052 B2 | 4/2022 | Church et al. |
| 11,434,525 B2 | 9/2022 | Glezer |
| 11,459,603 B2 | 10/2022 | Tyagi et al. |
| 11,492,662 B2 | 11/2022 | Glezer et al. |
| 11,499,185 B2 | 11/2022 | Vijayan et al. |
| 11,643,679 B2 | 5/2023 | Glezer et al. |
| 11,702,649 B2 * | 7/2023 | Blainey .................. C40B 40/10 506/26 |
| 11,999,999 B2 | 6/2024 | Ju et al. |
| 2002/0045045 A1 | 4/2002 | Adams et al. |
| 2003/0017264 A1 | 1/2003 | Treadway et al. |
| 2006/0234261 A1 | 10/2006 | Pierce et al. |
| 2010/0055733 A1 | 3/2010 | Lutolf et al. |
| 2011/0223585 A1 | 9/2011 | Gullberg et al. |
| 2013/0288249 A1 | 10/2013 | Gullbert |
| 2013/0323729 A1 | 12/2013 | Landegren et al. |
| 2016/0108458 A1 | 4/2016 | Frei et al. |
| 2016/0115533 A1 | 4/2016 | Fabani et al. |
| 2016/0116384 A1 | 4/2016 | Chen et al. |
| 2016/0305856 A1 | 10/2016 | Boyden et al. |
| 2016/0376642 A1 | 12/2016 | Landegren et al. |
| 2017/0009278 A1 | 1/2017 | Söderberg et al. |
| 2017/0081489 A1 | 3/2017 | Rodriques et al. |
| 2017/0101672 A1 | 4/2017 | Luo et al. |
| 2017/0220733 A1 | 8/2017 | Zhuang et al. |
| 2017/0253918 A1 | 9/2017 | Kohman |
| 2018/0052081 A1 | 2/2018 | Kohman |
| 2018/0080876 A1 | 3/2018 | Rockel et al. |
| 2018/0208967 A1 | 7/2018 | Larman et al. |
| 2018/0223358 A1 | 8/2018 | Drmanac et al. |
| 2018/0237864 A1 | 8/2018 | Imler et al. |
| 2018/0305749 A1 | 10/2018 | Stromberg et al. |
| 2018/0320226 A1 | 11/2018 | Church et al. |
| 2019/0017106 A1 | 1/2019 | Frisen et al. |
| 2019/0032128 A1 | 1/2019 | Chen et al. |
| 2019/0055594 A1 | 2/2019 | Samusik et al. |
| 2019/0106733 A1 | 4/2019 | Kishi et al. |
| 2019/0112599 A1 | 4/2019 | Church et al. |
| 2019/0119735 A1 | 4/2019 | Deisseroth et al. |
| 2019/0155835 A1 | 5/2019 | Daugharthy et al. |
| 2019/0161796 A1 | 5/2019 | Hauling et al. |
| 2019/0177718 A1 | 6/2019 | Church et al. |
| 2019/0177800 A1 | 6/2019 | Boutet et al. |
| 2019/0194709 A1 | 6/2019 | Church et al. |
| 2019/0218608 A1 | 7/2019 | Daugharthy et al. |
| 2019/0249248 A1 | 8/2019 | Beechem et al. |
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2019/0339203 A1 | 11/2019 | Miller et al. |
| 2019/0367969 A1 | 12/2019 | Belhocine |
| 2020/0010891 A1 | 1/2020 | Beechem et al. |
| 2020/0071751 A1 | 3/2020 | Daugharthy et al. |
| 2020/0123597 A1 | 4/2020 | Daniel |
| 2020/0140920 A1 | 5/2020 | Pierce et al. |
| 2020/0224243 A1 | 7/2020 | Desai et al. |
| 2020/0224244 A1 | 7/2020 | Nilsson et al. |
| 2020/0239946 A1 | 7/2020 | Dewal |
| 2020/0255888 A1 * | 8/2020 | Jensen .................. G16B 30/00 |
| 2020/0354774 A1 | 11/2020 | Church et al. |
| 2020/0354782 A1 | 11/2020 | Dewal |
| 2020/0362398 A1 | 11/2020 | Kishi et al. |
| 2020/0370113 A1 | 11/2020 | Kellinger et al. |
| 2020/0393343 A1 | 12/2020 | Kennedy-Darling et al. |
| 2020/0399689 A1 | 12/2020 | Luo et al. |
| 2021/0017587 A1 | 1/2021 | Cai et al. |

(56) References Cited

U.S. PATENT DOCUMENTS

| | | |
|---|---|---|
| 2021/0115504 A1 | 4/2021 | Cai et al. |
| 2021/0164039 A1 | 6/2021 | Wang et al. |
| 2021/0198723 A1 | 7/2021 | Kuhnemund et al. |
| 2021/0198727 A1 | 7/2021 | Kuhnemund et al. |
| 2021/0238662 A1 | 8/2021 | Bava |
| 2021/0238674 A1 | 8/2021 | Bava |
| 2021/0254140 A1 | 8/2021 | Stahl et al. |
| 2021/0262018 A1 | 8/2021 | Bava et al. |
| 2021/0277460 A1 | 9/2021 | Bava |
| 2021/0340621 A1 | 11/2021 | Daugharthy et al. |
| 2021/0388423 A1 | 12/2021 | Bava et al. |
| 2021/0388424 A1 | 12/2021 | Bava |
| 2022/0049302 A1 | 2/2022 | Daugharthy et al. |
| 2022/0049303 A1 | 2/2022 | Busby et al. |
| 2022/0064697 A1 | 3/2022 | Zhuang et al. |
| 2022/0083832 A1 | 3/2022 | Shah |
| 2022/0084628 A1 | 3/2022 | Shah |
| 2022/0084629 A1 | 3/2022 | Shah |
| 2022/0136049 A1 | 5/2022 | Bava et al. |
| 2022/0186300 A1 | 6/2022 | Bava |
| 2022/0195498 A1 | 6/2022 | Kuhnemund et al. |
| 2022/0213529 A1 | 7/2022 | Kuhnemund et al. |
| 2022/0228200 A1 | 7/2022 | Bava |
| 2022/0235403 A1 | 7/2022 | Costa |
| 2022/0282306 A1 | 9/2022 | Bava et al. |
| 2022/0282316 A1 | 9/2022 | Bava et al. |
| 2022/0282319 A1 | 9/2022 | Verheyen et al. |
| 2022/0372570 A1 | 11/2022 | Costa |
| 2022/0380838 A1 | 12/2022 | Kuhnemund et al. |
| 2022/0403458 A1 | 12/2022 | Bava et al. |
| 2023/0002808 A1 | 1/2023 | Mignardi |
| 2023/0012607 A1 | 1/2023 | Kuhnemund et al. |
| 2023/0013775 A1 | 1/2023 | Chen |
| 2023/0015226 A1 | 1/2023 | Chen |
| 2023/0026886 A1 | 1/2023 | Chen |
| 2023/0031305 A1 | 2/2023 | Neuta et al. |
| 2023/0031996 A1 | 2/2023 | Neuta et al. |
| 2023/0035685 A1 | 2/2023 | Neuta et al. |
| 2023/0037182 A1 | 2/2023 | Bava et al. |
| 2023/0039148 A1 | 2/2023 | Verheyen et al. |
| 2023/0041485 A1 | 2/2023 | Neuta et al. |
| 2023/0044650 A1 | 2/2023 | Dockter |
| 2023/0057571 A1 | 2/2023 | Costa et al. |
| 2023/0061542 A1 | 3/2023 | Kuhnemund et al. |
| 2023/0084407 A1 | 3/2023 | Neuta et al. |
| 2023/0159997 A1 | 5/2023 | Belhocine et al. |
| 2023/0160794 A1 | 5/2023 | Dockter et al. |
| 2023/0183787 A1 | 6/2023 | Bava et al. |
| 2023/0242974 A1 | 8/2023 | Costa et al. |
| 2023/0265499 A1 * | 8/2023 | Wells ................ C12N 15/1065 435/6.11 |
| 2023/0279465 A1 | 9/2023 | He et al. |
| 2023/0279475 A1 | 9/2023 | Kuhnemund et al. |
| 2023/0279480 A1 | 9/2023 | Kuhnemund et al. |
| 2023/0287478 A1 | 9/2023 | Bava |
| 2023/0314327 A1 | 10/2023 | Hoffman |
| 2023/0314328 A1 | 10/2023 | Costa |
| 2023/0323427 A1 | 10/2023 | Levin |
| 2023/0323430 A1 | 10/2023 | Shastry |
| 2023/0323437 A1 | 10/2023 | Chen |
| 2023/0374573 A1 | 11/2023 | Qian et al. |
| 2023/0374580 A1 | 11/2023 | Costa |
| 2023/0416821 A1 | 12/2023 | Bava et al. |
| 2024/0002902 A1 | 1/2024 | Jakobsen et al. |
| 2024/0026426 A1 | 1/2024 | Costa |
| 2024/0026427 A1 | 1/2024 | Kuhnemund et al. |
| 2024/0026439 A1 | 1/2024 | Sasaki et al. |
| 2024/0026448 A1 | 1/2024 | Costa |
| 2024/0035070 A1 | 2/2024 | Christopherson |
| 2024/0035071 A1 | 2/2024 | Delaney et al. |
| 2024/0035072 A1 | 2/2024 | Christopherson |
| 2024/0043910 A1 | 2/2024 | Shastry |
| 2024/0043914 A1 | 2/2024 | Chen |
| 2024/0060119 A1 | 2/2024 | Bava et al. |
| 2024/0084373 A1 | 3/2024 | Shastry |
| 2024/0084378 A1 | 3/2024 | Marks et al. |
| 2024/0101978 A1 | 3/2024 | Boghospor |
| 2024/0132938 A1 | 4/2024 | Kuhnemund et al. |
| 2024/0141418 A1 | 5/2024 | Mielinis |
| 2024/0150816 A1 | 5/2024 | Feng et al. |
| 2024/0158852 A1 | 5/2024 | Belhocine et al. |
| 2024/0167081 A1 | 5/2024 | Bava et al. |
| 2024/0175082 A1 | 5/2024 | Costa |
| 2024/0175083 A1 | 5/2024 | Bava et al. |
| 2024/0191297 A1 | 6/2024 | Christopherson et al. |
| 2024/0209330 A1 | 6/2024 | Shastry et al. |
| 2024/0218424 A1 | 7/2024 | Costa et al. |
| 2024/0218437 A1 | 7/2024 | Belhocine et al. |
| 2024/0263219 A1 | 8/2024 | Kuhnemund |
| 2024/0263220 A1 | 8/2024 | Olofsson |
| 2024/0264155 A1 | 8/2024 | Costa |

FOREIGN PATENT DOCUMENTS

| | | | | |
|---|---|---|---|---|
| WO | WO 2014/163886 | | 10/2014 | |
| WO | WO 2017/117235 | | 7/2017 | |
| WO | WO 2017/143155 | | 8/2017 | |
| WO | WO-2018115852 A1 * | | 6/2018 | ......... C12N 15/1065 |
| WO | WO 2019/199579 | | 10/2019 | |
| WO | WO 2020/076976 | | 4/2020 | |
| WO | WO 2020/076979 | | 4/2020 | |
| WO | WO 2020/096687 | | 5/2020 | |
| WO | WO 2020/099640 | | 5/2020 | |
| WO | WO 2020/117914 | | 6/2020 | |
| WO | WO 2020/123316 | | 6/2020 | |
| WO | WO 2020/123742 | | 6/2020 | |
| WO | WO 2020/142490 | | 7/2020 | |
| WO | WO 2020/240025 | | 12/2020 | |
| WO | WO 2020/254519 | | 12/2020 | |
| WO | WO 2021/123282 | | 6/2021 | |
| WO | WO 2021/123286 | | 6/2021 | |
| WO | WO 2021/138676 | | 7/2021 | |
| WO | WO 2021/155063 | | 8/2021 | |
| WO | WO 2021/168326 | | 8/2021 | |
| WO | WO 2022/038527 A1 | | 2/2022 | |
| WO | WO 2022/197589 | | 9/2022 | |
| WO | WO-2022192603 A1 * | | 9/2022 | ......... C12N 15/1065 |
| WO | WO 2023/108139 | | 6/2023 | |
| WO | WO 2023/141476 | | 7/2023 | |
| WO | WO 2023/172915 | | 9/2023 | |
| WO | WO 2023/192302 | | 10/2023 | |
| WO | WO 2023/220300 | | 11/2023 | |
| WO | WO 2024/148300 | | 7/2024 | |

OTHER PUBLICATIONS

Allawi et al., "Thermodynamics and NMR of internal G.T mismatches in DNA," Biochemistry, (1997) 36:10581-94.

Archer et al., "Selective and flexible depletion of problematic sequences from RNA-seq libraries at the cDNA stage," BMC Genomics. (2014) 15(1):401.

Baner et al., "Signal amplification of padlock probes by rolling circle replication," Nucleic Acids Res. (1998) 26(22):5073-5078.

Bibikova et al., "Quantitative gene expression profiling in formalin-fixed, paraffin-embedded tissues using universal bead arrays," Am J Pathol. Nov. 2004;165(5):1799-807.

Bolognesi et al., "Multiplex Staining by Sequential Immunostaining and Antibody Removal on Routine Tissue Sections," J. Histochem. Cytochem. (2017); 65(8): 431-444.

Capodieci et al., "Gene expression profiling in single cells within tissue," Nat Methods. (2005) 2(9): 663-5.

Chemeris et al., "Real-time hybridization chain reaction," Dokl Biochem Biophys. (2008) 419: 53-55.

Chen et al., "Efficient in situ barcode sequencing using padlock probe-based BaristaSeq," Nucleic Acids Res. (2018) 46(4): e22.

Chen et al., "High-Throughput Mapping of Long-Range Neuronal Projection Using In Situ Sequencing," Cell. (2019) 179(3):772-786. e19.

Chen et al., "Nanoscale imaging of RNA with expansion microscopy," Nat Methods. (2016) 13:679-684.

(56) References Cited

OTHER PUBLICATIONS

Chen et al., "Expansion Microscopy," Science (2015) 347(6221):543-548.

Choi et al., "Programmable in situ amplification for multiplexed imaging of mRNA expression," Nat Biotechnol. (2010) 28(11): 1208-1212.

Conze et al., "Single molecule analysis of combinatorial splicing," Nucleic Acids Res. (2010) 38(16): e163.

Dean et al., "Rapid Amplification of Plasmid And Phage DNA Using Phi29 DNA Polymerase And Multiply-Primed Rolling Circle Amplification," Genome Research (2001) 11:1095-1099.

Dirks et al., "Triggered amplification by hybridization chain reaction," Proc Natl Acad Sci USA. (2004) 101(43): 15275-15278.

Eng et al., "Transcriptome-scale super-resolved imaging in tissues by RNA seqFISH," Nature. (2019) 568(7751): 235-239.

Fang et al., "Fluoride-Cleavable Biotinylation Phosphoramidite for 5'-end-Labelling and Affinity Purification of Synthetic Oligonucleotides," Nucleic Acids Res. (2003) 31(2): 708-715.

Faruqi et al., "High-throughput genotyping of single nucleotide polymorphisms with rolling circle amplification," BMC Genomics. (2001) 2:4.

Femino et al., "Visualization of single RNA transcripts in situ," Science. (1998) 280(5363): 585-90.

Gavrilovic et al., "Automated classification of multicolored rolling circle products in dual-channel wide-field fluorescence microscopy," Cytometry A. (2011) 79(7): 518-27.

Geiss et al., "Direct multiplexed measurement of gene expression with color-coded probe pairs," Nat Biotechnol. (2008) 26(3): 317-25.

Glass et al., "SIMPLE: a sequential immunoperoxidase labeling and erasing method," J Histochem Cytochem. (2009) 57(10); 899-905.

Goh, J.J.L. et al. (Jul. 2020, e-pub. Jun. 15, 2020). "Highly Specific Multiplexed RNA Imaging in Tissues With Split-FISH," Nat Methods 17(7):689-693. doi: 10.1038/s41592-020-0858-0. Epub Jun. 15, 2020.

Goransson et al., "A single molecule array for digital targeted molecular analyses," Nucleic Acids Res. 2009 37(1):e7. doi: 10.1093/nar/gkn921.

Gunderson et al. "Decoding randomly ordered DNA arrays." Genome research 14.5 (2004): 870-877.

Gyllborg et al., "Hybridization-based in situ sequencing (HybISS) for spatially resolved transcriptomics in human and mouse brain tissue," Nucleic Acids Res. (2020) 48(19): e112.

Han et al., "Quantum-dot-tagged microbeads for multiplexed optical coding of biomolecules," Nat Biotechnol. (2001) 19(7): 631-5.

Itzkovitz et al., "Single-molecule transcript counting of stem-cell markers in the mouse intestine," Nat Cell Biol. (2011) 14(1): 106-14.

Itzkovitz et al., "Validating Transcripts with Probes and Imaging Technology," Nat Methods. (2011) 8(4 Suppl): S12-S19.

Jamur et al., "Permeabilization of cell membranes," Method Mol. Biol. (2010) 588: 63-66 (abstract only).

Kanehisa, "Use of statistical criteria for screening potential homologies in nucleic acid sequences," Nucleic Acids Res. (1984) 12:203-213.

Ke et al., "Fourth Generation of Next-Generation Sequencing Technologies: Promise and Consequences," Hum Mutat. (2016) 37(12):1363-1367.

Korostin et al., "Comparative analysis of novel MGISEQ-2000 sequencing platform vs Illumina HiSeq 2500 for whole-genome sequencing," PLoS One. (2020) 15(3): e0230301. 13 pages.

Lagunavicius et al., "Novel application of Phi29 DNA polymerase: RNA detection and analysis in vitro and in situ by target RNA-primed RCA," RNA. (2009) 15(5):765-71.

Larsson et al. "In situ detection and genotyping of individual mRNA molecules," Nat Methods. (2010) 7(5):395-397.

Lee et al. "Highly Multiplexed Subcellular RNA Sequencing In Situ", Science (2014) 343(6177): 1360-1363.

Lee et al., "Direct RNA targeted transcriptomic profiling in tissue using Hybridization-based RNA In Situ Sequencing (HybRISS)," bioRxiv. (2020) 7 pages.

Lee et al., "Fluorescent in situ sequencing (FISSEQ) of RNA for gene expression profiling in intact cells and tissues," Nat Protoc. (2015) 10(3): 442-58.

Levsky et al., "Fluorescence in situ hybridization: past, present and future," J Cell Sci. (2003) 116(Pt 14): 2833-8.

Levsky et al., "Single-cell gene expression profiling," Science. (2002) 297(5582): 836-40.

Lin et al., "Highly multiplexed imaging of single cells using a high-throughput cyclic immunofluorescence method," Nat Commun. (2015) 6:8390.

Liu et al. Barcoded oligonucleotides ligated on RNA amplified for multiplexed and parallel in situ analyses. Nucleic Acids Res. (2021) 49(10): e58, 15 pages. doi: 10.1093/nar/gkab120.

Lizardi et al., "Mutation detection and single-molecule counting using isothermal rolling-circle amplification," Nat Genet. (1998) 19(3): 225-232.

Maierhorfer et al., "Multicolor deconvolution microscopy of thick biological specimens," Am J Pathol. (2003) 162(2): 373-9.

Mcginn et al., "New technologies for DNA analysis—a review of the READNA Project," N Biotechnol. (2016) 33(3): 311-30. doi: 10.1016/j.nbt.2015.10.003.

Meade et al. "Multiplexed DNA detection using spectrally encoded porous SiO2 photonic crystal particles," Anal Chem. (2009) 81(7): 2618-25.

Mohsen et al., "The Discovery of Rolling Circle Amplification and Rolling Circle Transcription," Acc Chem Res. (2016) 49(11): 2540-2550.

Nallur et al., "Signal amplification by rolling circle amplification on DNA microarrays," Nucleic Acids Res. (2001) 29(23): e118.

Niu et al., "Fluorescence detection for DNA using hybridization chain reaction with enzyme-amplification," Chem Commun (Camb). (2010) 46(18): 308+A332-91.

Payne et al. "In situ genome sequencing resolves DNA sequence and structure in intact biological samples," Science. (2021) 371(6532): eaay3446. doi: 10.1126/science.aay3446. Epub Dec. 31, 2020.

Pirici et al., "Antibody elution method for multiple immunohistochemistry on primary antibodies raised in the same species and of the same subtype," J Histochem Cytochem. (2009) 57(6); 567-75.

Raj et al., "Imaging individual mRNA molecules using multiple singly labeled probes," Nat Methods. (2008) 5(10): 877-879.

Rouhanifard et al. "ClampFISH detects individual nucleic acid molecules using click chemistry-based amplification," Nat Biotechnol. (2018) 17 pages. doi: 10.1038/nbt.4286.

Schweitzer et al. "Immunoassays with rolling circle DNA amplification: A versatile platform for ultrasensitive antigen detection," Proc. Natl Acad. Sci. USA (2000) 97:10113-119.

Schweitzer et al., "Multiplexed protein profiling on microarrays by rolling-circle amplification," Nature Biotech. (2002) 20:359-365.

Song et al., "Hybridization chain reaction-based aptameric system for the highly selective and sensitive detection of protein," Analyst. (2012) 137(6):1396-1401.

Sun et al., "Composite organic-inorganic nanoparticles as Raman labels for tissue analysis," Nano Lett. (2007) 7(2): 351-6.

Takei et al., (Feb. 2021, e-pub Jan. 27, 2021). "Integrated Spatial Genomics Reveals Global Architecture of Single Nuclei," Nature 590(7845): 344-350, 53 pages. doi: 10.1038/s41586-020-03126-2.

Vandernoot et al., "cDNA normalization by hydroxyapatite chromatography to enrich transcriptome diversity in RNA-seq applications," Biotechniques, (2012) 53(6) 373-80.

Wählby et al., "Sequential immunofluorescence staining and image analysis for detection of large Nos. of antigens in individual cell nuclei," Cytometry. (2002) 47(1): 32-41.

Wang et al., "Three-dimensional intact-tissue sequencing of single-cell transcriptional states," Science. (2018) 361(6400): eaat5691.

Weibrecht et al., "Simultaneous visualization of both signaling cascade activity and end-point gene expression in single cells," PLoS One. (2011) 6(5): e20148.

(56) References Cited

OTHER PUBLICATIONS

Wetmur, "DNA Probes: Applications of the Principles of Nucleic Acid Hybridization," Critical Reviews in Biochemistry and Molecular Biology, (1991) 26(91); 227-259.
Wilson et al., "Encoded microcarriers for high-throughput multiplexed detection," Angew Chem Int Ed Engl. (2006) 18;45(37):6104-17.
Wu, C. et al. "RollFISh Achieves Robust Quantification of Single-Molecule RNA Biomarkers in Paraffin-Embedded Tumor Tissue Samples," Commun Biol. (2018) 1:(209):1-8. doi: 10.1038/s42003-018-0218-0.
Zhao et al., "Advances of multiplex and high throughput biomolecular detection technologies based on encoding microparticles," Sci China Chem. (2011) 54(8):1185.
Pei, D. "How Do Biomolecules Cross the Cell Membrane?" Acc Chem Res. (2022) 55(3):309-318.
U.S. Appl. No. 18/589,350, filed Feb. 27, 2024, by Patrick J. Marks et al.
Sun et al., "Integrating barcoded neuroanatomy with spatial transcriptional profiling enables identification of gene correlates of projections," Nat Neurosci. (2021) 24(6):873-885.

\* cited by examiner

SEQUENCE LISTING

```
Sequence total quantity: 3
SEQ ID NO: 1            moltype = DNA  length = 15
FEATURE                 Location/Qualifiers
source                  1..15
                        mol_type = other DNA
                        organism = synthetic construct
SEQUENCE: 1
gggaggggcg tgggg                                                            15

SEQ ID NO: 2            moltype = DNA  length = 15
FEATURE                 Location/Qualifiers
source                  1..15
                        mol_type = other DNA
                        organism = synthetic construct
SEQUENCE: 2
gcgggaggtg ggagg                                                            15

SEQ ID NO: 3            moltype = DNA  length = 16
FEATURE                 Location/Qualifiers
source                  1..16
                        mol_type = other DNA
                        organism = synthetic construct
SEQUENCE: 3
gggaggggcg tgggga                                                           16
```

COMPOSITIONS AND METHODS FOR GENE EXPRESSION LIBRARY ANALYSIS

CROSS REFERENCE TO RELATED APPLICATIONS

This application is a continuation of International Application No. PCT/US2023/021925, filed on May 11, 2023, which claims the benefit of and priority to U.S. Provisional Application No. 63/340,730, filed on May 11, 2022, the contents of each of which are incorporated herein by reference in their entirety.

REFERENCE TO AN ELECTRONIC SEQUENCE LISTING

The contents of the electronic sequence listing (202412011904SEQLIST.xml; Size: 3,461 bytes; and Date of Creation: Feb. 22, 2024) is herein incorporated by reference in its entirety.

FIELD

The present disclosure generally relates to methods and compositions for in situ detection of analytes in a sample.

BACKGROUND

Genomic, transcriptomic, and proteomic profiling of cells and tissue samples using microscopic imaging can resolve multiple analytes of interest at the same time, thereby providing valuable information regarding analyte abundance and localization in situ. Thus, in situ assays are important tools, for example, for understanding the molecular basis of cell identity and developing treatment for diseases. There is a need for new and improved methods for in situ assays. Provided herein are methods and compositions that address such and other needs.

SUMMARY

Plex-scalability of in situ detection methods can be limited by optical crowding. For example, signals associated with large size features (e.g., rolling circle amplification (RCA) products, nucleic acid probes, or nucleic acid complexes) and/or high intensity may overlap with and/or mask other signals, especially when the signals arise from features that are in close proximity, whereas signals associated with small size features and/or weak intensity may not reach a detection threshold. In either case, the quality of signal detection and decoding of, e.g., identifier sequences associated with target analytes in multiplexed assays can be compromised. In addition, certain existing methods require complex pools of oligonucleotide probes, adding to the cost and time for detection and decoding.

The present disclosure relates in some aspects to methods and compositions for base-by-base sequencing in situ in a cell or tissue sample. In some embodiments, a sequencing primer hybridizes to a priming site 3' to an identifier sequence (e.g., a barcode sequence) in the sample such that the sequencing primer can be extended by a polymerase in a base-by-base fashion using a sequence of the identifier sequence as a template. The cell or tissue sample can be contacted with nucleotides in a cyclic series of nucleotide incorporation or nucleotide binding steps and signals indicative of the incorporation or binding events can be detected in each cycle to generate a signal code sequence comprising a series of signal codes corresponding to a signal (an ON signal), an absence of signal (an OFF signal), or a combination of ON and OFF signals detected in the sequential cycles. The signal code sequences for multiple different identifier sequences can be generated at locations in the sample and used to decode the corresponding analytes.

In some embodiments, provided herein is a method of analyzing a biological sample, comprising: a) contacting the biological sample with a first probe and a second probe, wherein: the biological sample is a cell or tissue sample, the biological sample comprises a first analyte and a second analyte at a first location and a second location, respectively, in the biological sample, the first probe and the second probe directly or indirectly bind to the first analyte and the second analyte, respectively, the first probe or a product thereof comprises i) a first priming site for a first sequencing primer and ii) a first identifier sequence associated with the first analyte, and the second probe or a product thereof comprises i) a second priming site for a second sequencing primer and ii) a second identifier sequence associated with the second analyte; b) performing base-by-base sequencing, e.g., sequencing by synthesis (SBS) or sequencing by binding (SBB), of the first and second identifier sequences using the first and second sequencing primers, thereby generating a first signal code sequence and a second signal code sequence, each comprising signal codes each corresponding to a signal (an ON signal), an absence of signal (an OFF signal), or a combination thereof, detected in sequential cycles at the first location and the second location, respectively, wherein in one or more of the sequential cycles, an ON signal is detected at the first location and an OFF signal is detected at the second location; and c) detecting the first and second identifier sequences in the biological sample based at least in part on the first and a second signal code sequences.

In some embodiments, the first and second analytes are the same. In some embodiments, the first and second analytes are different. In any of the embodiments herein, the first and second identifier sequences can different. In any of the embodiments herein, the first and second identifier sequences can comprise analyte sequences or complements thereof.

In any of the embodiments herein, the first and second identifier sequences can comprise barcode sequences or complements thereof. In any of the embodiments herein, the barcode sequences can be assigned to the first and second analytes, respectively. In some embodiments, assigning the barcode sequence is based on a decision rule designed to minimize a maximum predicted density of ON signals detected in each of the one or more of the sequential cycles. In some embodiments, the decision rule for assigning the first barcode sequence to the first analyte and the second barcode sequence to the second analyte comprises assignment based on expression data for the first analyte and the second analyte. In some embodiments, assigning the first barcode sequence to the first analyte and the second barcode sequence to the second analyte comprises assignment based on expression data for the first analyte and the second analyte in clustered cell types. In some embodiments, the clustered cell types represent a distribution of cell types found in the biological sample. In some embodiments, the expression data for the first analyte and the second analyte is at least partially overlap. In some embodiments, the expression data for the first analyte and the second analyte comprises bulk gene expression data, bulk protein expression data, spatial gene expression data, spatial protein expression data, single cell gene expression data, single cell protein expression data, or any combination thereof.

In any of the embodiments herein, the method can comprise assigning a first barcode sequence to the first analyte and a second barcode sequence to the second analyte. In some embodiments, a nucleotide in the first barcode sequence detected in a particular cycle corresponds to a signal code comprising an ON signal, and the corresponding nucleotide in the second barcode sequence detected in the particular cycle corresponds to a signal code comprising an OFF signal. In some embodiments, the nucleotide in the first barcode sequence detected in the particular cycle corresponds to ON signal(s) only, and the corresponding nucleotide in the second barcode sequence detected in the particular cycle corresponds to OFF signal(s) only. In any of the embodiments herein, one or more pairs of corresponding nucleotides in the first and second barcode sequences to be detected in the same cycle can be chosen to reduce optical crowding of signals detected in the cycle.

In any of the embodiments herein, the base-by-base sequencing can be performed by contacting the biological sample with nucleotides in sequential cycles, wherein in each cycle a complex is formed, the complex comprising i) the first or second sequencing primer or an extension product thereof hybridized to the first or second priming site, respectively, ii) a polymerase, and iii) a cognate nucleotide that base pairs with a nucleotide in the first or second identifier sequence, and a signal (an ON signal) and/or an absence of signal (an OFF signal) associated with the cognate nucleotide and/or the polymerase in the complex is detected at a particular location in the biological sample, wherein the ON signal, the OFF signal, or a combination thereof corresponds to the base in the cognate nucleotide and the corresponding nucleotide in the first or second identifier sequence.

In any of the embodiments herein, 25% or more of the nucleotides in the first and/or second identifier sequences can be assigned to correspond to OFF signals. In any of the embodiments herein, the first and/or second identifier sequences can be designed such that more than 25% of the nucleotides therein correspond to OFF signals. In any of the embodiments herein, 30% or more of the nucleotides in the first and/or second identifier sequences can be assigned to correspond to OFF signals. In any of the embodiments herein, the first and/or second identifier sequences can be designed such that more than 30% of the nucleotides therein correspond to OFF signals. In any of the embodiments herein, the first and/or second identifier sequences can be designed such that more than 35% of the nucleotides therein correspond to OFF signals. In any of the embodiments herein, 40% or more of the nucleotides in the first and/or second identifier sequences can be assigned to correspond to OFF signals. In any of the embodiments herein, the first and/or second identifier sequences can be designed such that more than 45% of the nucleotides therein correspond to OFF signals. In any of the embodiments herein, 50% or more of the nucleotides in the first and/or second identifier sequences can be assigned to correspond to OFF signals. In any of the embodiments herein, the first and/or second identifier sequences can be designed such that more than 55% of the nucleotides therein correspond to OFF signals. In any of the embodiments herein, 60% or more of the nucleotides in the first and/or second identifier sequences can be assigned to correspond to OFF signals. In any of the embodiments herein, the first and/or second identifier sequences can be designed such that more than 65% of the nucleotides therein correspond to OFF signals. In any of the embodiments herein, 70% or more of the nucleotides in the first and/or second identifier sequences can be assigned to correspond to OFF signals. In any of the embodiments herein, 75% or more of the nucleotides in the first and/or second identifier sequences can be assigned to correspond to OFF signals. In any of the embodiments herein, 80% or more of the nucleotides in the first and/or second identifier sequences can be assigned to correspond to OFF signals. In any of the embodiments herein, 85% or more of the nucleotides in the first and/or second identifier sequences can be assigned to correspond to OFF signals. In any of the embodiments herein, 90% or more of the nucleotides in the first and/or second identifier sequences can be assigned to correspond to OFF signals. In any of the embodiments herein, 95% or more of the nucleotides in the first and/or second identifier sequences can be assigned to correspond to OFF signals.

In any of the embodiments herein, multiple different identifier sequences can be detected in the biological sample, and each different identifier sequence can be detected at one or more locations in the biological sample. In some embodiments, the multiple different identifier sequences are a plurality of unique identifier sequences, e.g., each uniquely corresponding to an analyte. In any of the embodiments herein, 50% or more of the different identifier sequences can each comprise 50% or more of the nucleotides in the identifier sequence that correspond to OFF signals. In any of the embodiments herein, 80% or more of the different identifier sequences can each comprise 80% or more of the nucleotides in the identifier sequence that correspond to OFF signals.

In any of the embodiments herein, the signal codes can each correspond to a signal of a first color, a signal of a second color, a signal of a third color, or an absence of signal, and wherein the first, second, and third colors are different. In any of the embodiments herein, the signal codes can each correspond to a signal of a first color, a signal of a second color, a combination of signals of the first and second colors, or absence of signal, wherein the first and second colors are different. In any of the embodiments herein, the signal codes can each correspond to a combination of a signal (an ON signal) and/or absence of signal (an OFF signal), wherein the combination of ON and/or OFF signals is detected in two or more imaging steps.

In any of the embodiments herein, the method can further comprise detecting the first and second analytes in the biological sample based on detecting the first and second identifier sequences. In any of the embodiments herein, the first identifier sequence can be a sequence or a complement thereof of the first analyte. In any of the embodiments herein, the second identifier sequence can be a sequence or a complement thereof of the second analyte. In any of the embodiments herein, the first identifier sequence can be a first barcode sequence or a complement thereof corresponding to, associated with, and/or identifying the first analyte. In any of the embodiments herein, the second identifier sequence can be a second barcode sequence or a complement thereof corresponding to, associated with, and/or identifying the second analyte.

In any of the embodiments herein, the first barcode sequence can be used to identify the first analyte. In any of the embodiments herein, the second barcode sequence can be used to identify the second analyte.

In any of the embodiments herein, the first probe can be provided in a first plurality of probes that directly or indirectly bind to the first analyte. In some embodiments, the first plurality of probes collectively comprise a first combination of barcode sequences, and the first combination of barcode sequences identifies the first analyte. In any of the embodiments herein, the second probe can be provided in a second plurality of probes that directly or indirectly bind to the second analyte. In some embodiments, the second plurality of probes collectively comprise a second combination of barcode sequences, and the second combination of barcode sequences identifies the second analyte.

In any of the embodiments herein, the first and second analytes can comprise nucleic acid sequences. In any of the embodiments herein, the first identifier sequence can comprise a sequence of the first analyte or a complement thereof, and the second identifier sequence can comprise a sequence of the second analyte or a complement thereof.

In any of the embodiments herein, the base-by-base sequencing can comprise using a polymerase that is fluorescently labeled and one or more nucleotides that are not fluorescently labeled. In any of the embodiments herein, the base-by-base sequencing can comprise using a polymerase-nucleotide conjugate comprising a fluorescently labeled polymerase linked to a nucleotide moiety that is not fluorescently labeled. In any of the embodiments herein, the base-by-base sequencing can comprise using a multivalent polymer-nucleotide conjugate comprising a polymer core, multiple nucleotide moieties, and one or more fluorescent labels.

In some embodiments, during the base-by-base sequencing, a cognate nucleotide is not incorporated by the polymerase into the first or second sequencing primer or an extension product thereof. In some embodiments, incorporation of a cognate nucleotide by the polymerase into the first or second sequencing primer or an extension product thereof is attenuated or inhibited.

In any of the embodiments herein, the base-by-base sequencing can comprise contacting the biological sample with a nucleotide mix comprising a fluorescently labeled nucleotide and a nucleotide that is not fluorescently labeled. In some embodiments, during the base-by-base sequencing, a cognate nucleotide is incorporated by a polymerase into the first or second sequencing primer or an extension product thereof, and the cognate nucleotide is or is not fluorescently labeled.

In any of the embodiments herein, the base-by-base sequencing can comprise: contacting the biological sample with a first nucleotide mix in which nucleotides comprising a first base are not detectably labeled, whereas nucleotides comprising bases other than the first base are each labeled with one or more detectably labels, and contacting the biological sample with a subsequent nucleotide mix in which nucleotides comprising a subsequent base are not detectably labeled, whereas nucleotides comprising bases other than the subsequent base are each labeled with one or more detectably labels, wherein the subsequent base is the same as the first base, optionally wherein the first and subsequent bases are A, T, C, or G.

In any of the embodiments herein, the base-by-base sequencing can comprise: contacting the biological sample with a first nucleotide mix in which nucleotides comprising a first base are not detectably labeled, whereas nucleotides comprising bases other than the first base are each labeled with one or more detectably labels, and contacting the biological sample with a subsequent nucleotide mix in which nucleotides comprising a subsequent base are not detectably labeled, whereas nucleotides comprising bases other than the subsequent base are each labeled with one or more detectably labels, wherein the subsequent base is different from the first base.

In any of the embodiments herein, the biological sample can be contacted with two or more of the following nucleotide mixes in sequential cycles in any order: nucleotide mix 1 in which nucleotides comprising G are not detectably labeled, whereas nucleotides comprising A, C, or T are detectably labeled; nucleotide mix 2 in which nucleotides comprising T are not detectably labeled, whereas nucleotides comprising A, C, or G are detectably labeled; nucleotide mix 3 in which nucleotides comprising C are not detectably labeled, whereas nucleotides comprising A, G, or T are detectably labeled; and nucleotide mix 4 in which nucleotides comprising A are not detectably labeled, whereas nucleotides comprising G, C, or T are detectably labeled.

In any of the embodiments herein, each nucleotide mix independent of one another can be contacted with the biological sample in one or more cycles, wherein the cycles are consecutive or nonconsecutive. In any of the embodiments herein, independent of one another, each nucleotide mix can comprise: detectably labeled nucleotides having fluorescent labels of three different colors, one for each of the three bases, e.g., red for A, blue for G, green for T, and no detectable label for C; detectably labeled nucleotides having fluorescent labels of two different colors, one each for two of the three bases, wherein nucleotides comprising the remaining base are labeled with both colors, e.g., red and green for A, red for G, green for T, and no detectable label for C; or detectably labeled nucleotides having fluorescent labels of the same color, wherein fluorescent labels on nucleotides comprising one of the three bases are configured to be cleaved, and nucleotides comprising another one of the three bases are configured to be labeled with the fluorescent label.

In any of the embodiments herein, the biological sample may be contacted with two or more of the following nucleotide mixes in sequential cycles in any order: nucleotide mix 1 in which nucleotides comprising G or A are not detectably labeled, whereas nucleotides comprising C or T are detectably labeled; nucleotide mix 2 in which nucleotides comprising G or T are not detectably labeled, whereas nucleotides comprising C or A are detectably labeled; nucleotide mix 3 in which nucleotides comprising G or C are not detectably labeled, whereas nucleotides comprising A or T are detectably labeled; and nucleotide mix 4 in which nucleotides comprising C or A are not detectably labeled, whereas nucleotides comprising G or T are detectably labeled; nucleotide mix 5 in which nucleotides comprising C or T are not detectably labeled, whereas nucleotides comprising G or A are detectably labeled; and nucleotide mix 6 in which nucleotides comprising A or T are not detectably labeled, whereas nucleotides comprising G or C are detectably labeled.

In any of the embodiments herein, the first priming site and the second priming site can be different. In any of the embodiments herein, the method can comprise: b1) hybridizing the first sequencing primer to the first priming site and performing base-by-base sequencing to generate an extension product of the first sequencing primer and the first signal code sequence; b2) removing, cleaving, or blocking the extension product of the first sequencing primer in b1); and b3) hybridizing the second sequencing primer to the second priming site and performing base-by-base sequencing (e.g., SBS or SBB) to generate an extension product of the second sequencing primer and the second signal code sequence.

In any of the embodiments herein, probes or products thereof for a first plurality of analytes can share a common first priming site, and probes or products thereof for a second plurality of analytes can share a common second priming site. In any of the embodiments herein, the second plurality of analytes can comprise two or more different analytes that are different from two or more different analytes of the first plurality of analytes.

In any of the embodiments herein, the biological sample can be contacted with a plurality of probes each configured to directly or indirectly bind to a different analyte, and each probe or product thereof can comprise a combination of different priming sites. In any of the embodiments herein, the first probe or product thereof can comprise a first combination of different priming sites comprising the first priming site. In any of the embodiments herein, the second probe or product thereof can comprise a second combination of different priming sites comprising the second priming site.

In any of the embodiments herein, the biological sample can be contacted with a third probe that directly or indirectly binds to a third analyte. In any of the embodiments herein, the third probe or product thereof can comprise a third combination of different priming sites comprising the first priming site, the second priming site, and/or a third priming site.

In any of the embodiments herein, any two or more of the first combination, the second combination, and the third combination can share one or more common priming sites.

In any of the embodiments herein, the method can comprise: b') contacting the biological sample with the first sequencing primer for base-by-base sequencing, thereby hybridizing the first sequencing primer to the first priming site in the first probe or product thereof and in one or more other probes or products thereof, and generating extension products of the first sequencing primer; b") removing, cleaving, or blocking the extension products of the first sequencing primer in b'); and b''') contacting the biological sample with the second sequencing primer for base-by-base sequencing, thereby hybridizing the second sequencing primer to the second priming site in the second probe or product thereof and in one or more other probes or products thereof, and generating extension products of the second sequencing primer.

In any of the embodiments herein, the base-by-base sequencing in b') can be performed by: contacting the biological sample with nucleotides in sequential cycles, detecting signals associated with nucleotide incorporation or binding for each sequential cycle, and generating signal code sequences for a first plurality of analytes.

In any of the embodiments herein, the base-by-base sequencing in b''') can be performed by: contacting the biological sample with nucleotides in sequential cycles, detecting signals associated with nucleotide incorporation or binding for each sequential cycle, and generating signal code sequences for a second plurality of analytes. In some embodiments, the first plurality of analytes and the second plurality of analytes comprise one or more common analytes. In some embodiments, the first plurality of analytes and the second plurality of analytes do not comprise a common analyte.

In any of the embodiments herein, each analyte independently can be a nucleic acid analyte or non-nucleic acid analyte. In any of the embodiments herein, each probe independently can be i) a primary probe that directly binds to its corresponding analyte, or ii) a probe that directly or indirectly binds to the primary probe. In some embodiments, the primary probe and the probe that directly or indirectly binds to the primary probe are independently selected from the group consisting of: a probe comprising a 3' or 5' overhang, optionally wherein the 3' or 5' overhang comprises one or more barcode sequences; a probe comprising a 3' overhang and a 5' overhang, optionally wherein the 3' overhang and the 5' overhang each independently comprises one or more barcode sequences; a circular probe; a circularizable probe or probe set; a probe or probe set comprising a split hybridization region configured to hybridize to a splint, optionally wherein the split hybridization region comprises one or more barcode sequences; and a combination thereof.

In any of the embodiments herein, the product of each probe can comprise a rolling circle amplification (RCA) product generated in situ in the biological sample. In any of the embodiments herein, the base-by-base sequencing can be performed in situ in the biological sample.

In some aspects, disclosed herein are methods of analyzing a biological sample, comprising: a) contacting the biological sample with a first sequencing primer and a second sequencing primer, wherein: the biological sample is a cell or tissue sample, the biological sample comprises a first nucleic acid and a second nucleic acid at a first location and a second location, respectively, in the biological sample, the first nucleic acid comprises i) a first priming site complementary to the first sequencing primer and ii) a first identifier sequence, and the second nucleic acid comprises i) a second priming site complementary to the second sequencing primer and ii) a second identifier sequence; b) performing base-by-base sequencing of the first identifier sequence using the first sequencing primer hybridized to the first priming site to generate a first signal code sequence comprising signal codes detected in sequential cycles at the first location, wherein a signal code corresponds to a signal (an ON signal), an absence of signal (an OFF signal), or a combination thereof; c) subsequently performing base-by-base sequencing of the second identifier sequence using the second sequencing primer hybridized to the second priming site to generate a second signal code sequence comprising signal codes detected in additional sequential cycles at the second location; wherein in at least one or more of the sequential cycles in b) and the additional sequential cycles in c), at one or both of the first and second locations, an OFF signal is detected; and d) detecting the first and second identifier sequences in the biological sample at the first and second locations, respectively, based at least in part on the first and a second signal code sequences.

In some aspects, disclosed herein are methods of analyzing a biological sample, comprising: a) contacting the biological sample with a first probe and a second probe, wherein: the biological sample is a cell or tissue sample, the biological sample comprises a first analyte and a second analyte at a first location and a second location, respectively, in the biological sample, the first probe and the second probe directly or indirectly bind to the first analyte and the second analyte, respectively, the first probe or a product thereof comprises i) a first priming site for a first sequencing primer and ii) a first identifier sequence associated with the first analyte, and the second probe or a product thereof comprises i) a second priming site for a second sequencing primer and ii) a second identifier sequence associated with the second analyte; b) performing base-by-base sequencing (e.g., using at least one dark base) of the first identifier sequence using the first sequencing primer to generate a first signal code sequence comprising signal codes detected in sequential cycles at the first location, wherein a signal code corresponds to a signal (an ON signal), an absence of signal (an OFF signal), or a combination thereof; c) subsequently performing base-by-base sequencing (e.g., using at least one dark base) of the second identifier sequence using the second sequencing primer to generate a second signal code sequence comprising signal codes detected in additional sequential cycles at the second location; wherein in at least one or more of the sequential cycles in b) and the additional sequential cycles in c), an OFF signal is detected; and d) detecting the first and second identifier sequences in the biological sample at the first and second locations, respectively, based at least in part on the first and a second signal code sequences. In some embodiments, in at least one or more of the sequential cycles in b) and the additional sequential cycles in c), at one or both of the first and second locations, an OFF signal is detected.

In some embodiments, in at least one or more of the sequential cycles using the first sequencing primer and the additional sequential cycles using the second sequencing primer, ON signals are not detected at both of the first and second locations in the same base-by-base sequencing cycle. In some embodiments, in at least one or more of the sequential cycles using the first sequencing primer and at least one or more of the additional sequential cycles using the second sequencing primer, ON signals are not detected at both of the first and second locations in the same base-by-base sequencing cycle. In some embodiments, in two or more of the sequential cycles using the first sequencing primer and two or more of the additional sequential cycles using the second sequencing primer, ON signals are not detected at both of the first and second locations in the same base-by-base sequencing cycle. In some embodiments, in three or more of the sequential cycles using the first sequencing primer and three or more of the additional sequential cycles using the second sequencing primer, ON signals are not detected at both of the first and second locations in the same base-by-base sequencing cycle. In cases where the first and second locations are in vicinity to each other, a method disclosed herein reduces optical crowding during base-by-base sequencing in situ in the biological sample.

In any of the embodiments herein, an OFF signal can be generated by performing the base-by-base sequencing using one, two, or three nucleotides (e.g., any one, two, or three of A, T/U, C, and G) that are not detectably labeled, whereas the other nucleotide or nucleotides are detectably labeled. A different nucleotide or different combination of nucleotides can be used in a particular cycle compared to one or more other cycles. In some embodiments, a nucleotide that is not detectably labeled can be a native nucleotide or a derivative thereof, e.g., a naturally occurring nucleotide, that does not include an exogenous label (e.g., a fluorescent dye or any other label) or chemical modification. The nucleotide or nucleotides that are detectably labeled can be covalently (e.g., via a bond or a linker) or non-covalently (e.g., via a binding pair such as a biotin or derivative or analog thereof and a streptavidin or derivative or analog thereof) conjugated to a detectable label (e.g., a fluorescent dye or any other label). In other examples, the nucleotide or nucleotides that are detectably labeled can be conjugated with a moiety (e.g., an antigen or an antigen binding molecule such as an antibody) that permits detection of the nucleotide with an agent that specifically binds to the moiety and is capable of producing a detectable signal, and the detectable signal produced by the agent can be used to detect incorporation of the nucleotide. The moiety can be conjugated with the nucleotide via a cleavable linker.

In any of the embodiments herein, an OFF signal can be generated by performing the base-by-base sequencing by omitting one, two, or three nucleotides (e.g., any one, two, or three of A, T/U, C, and G) from a nucleotide mix that is contacted with the sample in a particular sequencing cycle, whereas the nucleotide mix only contains the other nucleotide or nucleotides which are detectably labeled. A different nucleotide or different combination of nucleotides can be used (or omitted from the nucleotide mix) in a particular cycle compared to one or more other cycles.

In any of the embodiments herein, an OFF signal can be generated by performing the base-by-base sequencing by not detecting one, two, or three nucleotides (e.g., any one, two, or three of A, T/U, C, and G) that are contacted with the sample in a particular sequencing cycle, whereas only the other nucleotide or nucleotides are detected. A different nucleotide or different combination of nucleotides can be detected (or not detected) in a particular cycle compared to one or more other cycles. For example, in cases where an antigen- or antibody-labeled nucleotide is used in a sequencing cycle, not detecting the signal associated with the nucleotide can be achieved by omitting the corresponding antibody or antigen that is labeled with a detectable label from the signal detection in that sequencing cycle.

In any of the embodiments herein, a number of "ON" cycles/bits can be chosen that each codeword (e.g., corresponding to a signal code sequence) must have, and the codewords can be designed accordingly. In any of the embodiments herein, the number of "ON" cycles/bits can be between about 3 and about 8 in a codeword. In any of the embodiments herein, the number of "ON" cycles/bits can be 4, 5, 6, or 7 in a codeword. In any of the embodiments herein, constraints on the codeword can be employed to facilitate identification of a correct identifier sequence (e.g., barcode sequence, such as one corresponding to an RCP). In any of the embodiments herein, each codeword can have "ON" bits in at least X colors, where X is 3 or 4, to distinguish from background fluorescent sources which tend to remain in a single color.

In any of the embodiments herein, the first and second sequencing primers can be contacted with the sample simultaneously or sequentially in either order. In any of the embodiments herein, the first and second sequencing primers can be contacted with the sample simultaneously or sequentially in either order. In any of the embodiments herein, the first and second identifier sequences can be in a DNA (e.g., genomic DNA), RNA (e.g., mRNA), a probe that directly or indirectly binds to the DNA (e.g., genomic DNA) or RNA (e.g., mRNA), or a product such as a rolling circle amplification product of the DNA (e.g., genomic DNA), RNA (e.g., mRNA), or probe.

In any of the embodiments herein, the first and second identifier sequences may be the same. In any of the embodiments herein, the first and second identifier sequences may be different.

In any of the embodiments herein, the first and second identifier sequences may comprise barcode sequences or complements thereof assigned to the first and second analytes, respectively. In some embodiments, the first priming site and/or the first barcode sequence may be assigned to the first analyte and the second priming site and/or the second barcode sequence is assigned to the second analyte based on a decision rule designed to minimize a maximum predicted density of ON signals detected in each of the one or more of the sequential cycles. In some embodiments, the assigning may comprise assignment based on expression data for the first analyte and the second analyte. In some embodiments, the assigning may comprise assignment based on expression data for the first analyte and the second analyte in clustered cell types. In some embodiments, the clustered cell types may represent a distribution of cell types found in the biological sample. In some embodiments, the expression data of the first analyte and the second analyte may at least partially overlap. In some embodiments, the expression data for the first analyte and the second analyte comprises bulk gene expression data, bulk protein expression data, spatial gene expression data, spatial protein expression data, single cell gene expression data, single cell protein expression data, or any combination thereof.

In any of the embodiments herein, a nucleotide in the first barcode sequence or second barcode sequence detected in a particular cycle may correspond to a signal code comprising an ON signal. In any of the embodiments herein, a nucleotide in the first barcode sequence or second barcode sequence detected in a particular cycle may correspond to a signal code comprising an OFF signal. In some embodiments, the nucleotide in the first barcode sequence or second barcode sequence detected in the particular cycle corresponds to ON signal(s) only. In some embodiments, the nucleotide in the first barcode sequence or second barcode sequence detected in the particular cycle may correspond to OFF signal(s) only.

Also disclosed herein are method for decoding identifier sequences in a biological sample while minimizing optical crowding, the methods comprising: a) contacting the biological sample with a first probe and a second probe, wherein: the biological sample is a cell or tissue sample, the biological sample comprises a first analyte and a second analyte at a first location and a second location, respectively, in the biological sample, the first probe and the second probe directly or indirectly bind to the first analyte and the second analyte, respectively, the first probe or a product thereof comprises i) a first priming site for a first sequencing primer and ii) a first identifier sequence associated with the first analyte, and the second probe or a product thereof comprises i) a second priming site for a second sequencing primer and ii) a second identifier sequence associated with the second analyte; b) performing base-by-base sequencing of the first and second identifier sequences using the first and second sequencing primers, thereby generating a first signal code sequence and a second signal code sequence, each comprising signal codes corresponding to a signal (an ON signal), an absence of signal (an OFF signal), or a combination thereof, detected in sequential sequencing cycles at the first location and the second location, respectively, wherein the base-by-base sequencing comprises contacting the biological sample in each sequential cycle with a polymerase and a mixture of nucleotides comprising at least one nucleotide that is not detectably labeled; and c) detecting the first and second identifier sequences in the biological sample based at least in part on the first and a second signal code sequences.

In some embodiments, the first and second analytes may be the same or different. In some embodiments, the first and second identifier sequences are different.

In any of the embodiments herein, the first and second identifier sequences may comprise analyte sequences or complements thereof. In any of the embodiments herein, the first and second identifier sequences comprise barcode sequences or complements thereof assigned to the first and second analytes, respectively. In any of the embodiments herein, the method may comprise assigning a first barcode sequence to the first analyte and a second barcode sequence to the second analyte. In some embodiments, assigning the barcode sequence may be based on a decision rule designed to minimize a maximum predicted density of ON signals detected in each of the one or more of the sequential cycles. In some embodiments, assigning the first barcode sequence to the first analyte and the second barcode sequence to the second analyte comprises assignment may be based on expression data for the first analyte and the second analyte. In some embodiments, assigning the first barcode sequence to the first analyte and the second barcode sequence to the second analyte may comprise assignment based on expression data for the first analyte and the second analyte in clustered cell types. In some embodiments, the clustered cell types represent a distribution of cell types found in the biological sample. In some embodiments, the expression data for the first analyte and the second analyte is at least partially overlap. In some embodiments, the expression data for the first analyte and the second analyte comprises bulk gene expression data, bulk protein expression data, spatial gene expression data, spatial protein expression data, single cell gene expression data, single cell protein expression data, or any combination thereof.

In any of the embodiments herein, the mixture of nucleotides may comprise at least two nucleotides that are not detectably labeled. In some embodiments, the biological sample is contacted with two or more of the following nucleotide mixes in sequential sequencing cycles in any order: nucleotide mix 1 in which nucleotides comprising G are not detectably labeled, whereas nucleotides comprising A, C, or T are detectably labeled; nucleotide mix 2 in which nucleotides comprising T are not detectably labeled, whereas nucleotides comprising A, C, or G are detectably labeled; nucleotide mix 3 in which nucleotides comprising C are not detectably labeled, whereas nucleotides comprising A, G, or T are detectably labeled; and nucleotide mix 4 in which nucleotides comprising A are not detectably labeled, whereas nucleotides comprising G, C, or T are detectably labeled. In some embodiments, independent of one another, each nucleotide mix is contacted with the biological sample in one or more cycles, wherein the cycles are consecutive or nonconsecutive. In some embodiments, independent of one another, in each nucleotide mix, the detectably labeled nucleotides comprise: i) fluorescent labels of three different colors, one for each of the three bases; ii) fluorescent labels of two different colors, one each for two of the three bases, wherein nucleotides comprising the remaining base are labeled with both colors; or iii) fluorescent labels of the same color, wherein fluorescent labels on nucleotides comprising one of the three bases are configured to be cleaved, and nucleotides comprising another one of the three bases are configured to be labeled with the fluorescent label.

In some embodiments, the biological sample may be contacted with two or more of the following nucleotide mixes in sequential cycles in any order: nucleotide mix 1 in which nucleotides comprising G or A are not detectably labeled, whereas nucleotides comprising C or T are detectably labeled; nucleotide mix 2 in which nucleotides comprising G or T are not detectably labeled, whereas nucleotides comprising C or A are detectably labeled; nucleotide mix 3 in which nucleotides comprising G or C are not detectably labeled, whereas nucleotides comprising A or T are detectably labeled; and nucleotide mix 4 in which nucleotides comprising C or A are not detectably labeled, whereas nucleotides comprising G or T are detectably labeled; nucleotide mix 5 in which nucleotides comprising C or T are not detectably labeled, whereas nucleotides comprising G or A are detectably labeled; and nucleotide mix 6 in which nucleotides comprising A or T are not detectably labeled, whereas nucleotides comprising G or C are detectably labeled.

BRIEF DESCRIPTION OF THE DRAWINGS

The drawings illustrate certain features and advantages of this disclosure. These embodiments are not intended to limit the scope of the appended claims in any manner.

DETAILED DESCRIPTION

Figure 1:
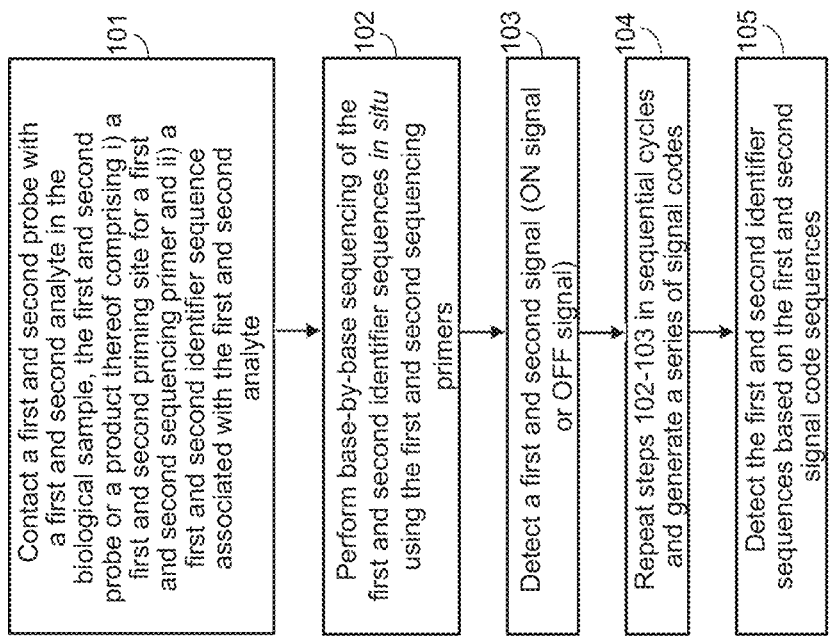
FIG. 1 shows an exemplary workflow comprising analyzing a first analyte and a second analyte in an in situ assay.

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Overview

Plex-scalability of in situ detection methods can be limited by optical crowding. For example, signals with large size and/or high intensity may overlap with and/or mask other signals, especially when the signals are in close proximity, whereas signals with small size and/or weak intensity may not reach a detection threshold. In either case, the quality of signal detection and decoding can be compromised. In addition, certain existing methods require complex pools of oligonucleotide probes, adding to the cost and time for detection and decoding.

For instance, in some aspects, single nucleotide sequencing chemistries (e.g., sequencing by synthesis (SBS), sequencing by binding (SBB), etc.) can offer fast reaction time and avoid the need for complex pools of oligonucleotide probes and sequential hybridization of the probe pools to decode, e.g., identifier sequences associated with target analytes in multiplexed assays. However, these base-by-base sequencing methods can be limited in plex-scalability for in situ analysis due to optical crowding during the signal detection and decoding steps. In particular, detecting large numbers of analytes (e.g., genes and/or transcripts thereof) in parallel in situ in a cell or tissue sample can be challenging.

Signal crowding can arise when there are a large number of signals to be detected. Using conventional base-by-base sequencing methods where each nucleotide in a sequencing cycle gives rise to an optical signal (e.g., a spot in an image acquired using fluorescent microscopy), a sample can become crowded with signal spots that are in close proximity (e.g., overlapping to some degree), thereby making resolution of individual spots difficult. Thus, spatial overlap may limit the ability to multiplex in microscopy-based nucleic acid sequencing assays. In some aspects, signal crowding may arise when one or more of the signals being detected are significantly stronger (e.g., have a significantly larger amplitude or intensity) than other signal(s). For example, in the same microscope field of view, one or more fluorescent spots may be significantly stronger than other spots, including neighboring spots. When too many signal spots are present in a sample, or when the amplitude of a signal is significantly greater than that of another signal, it can be difficult to accurately and reliably detect all of the signals in the same field of view and/or in the same detection channel (e.g., the same fluorescent channel). In some cases, signal crowding can cause weaker (e.g., lower amplitude) or overlapping signals to be masked and/or drop out, which ultimately leads to information from the analytes in the sample being lost. In such circumstances, the effective dynamic range of the detection can be reduced.

In some embodiments, provided herein are methods and compositions that can be used to prevent and/or address issues associated with optical crowding during base-by-base sequence determination in situ.

In some embodiments, provided herein is a method of analyzing a cell or tissue sample, where identifier sequences (e.g., sequences of nucleic acid analytes, or barcode sequences in analyte-targeting probes) for various analytes are sequenced in situ, thereby detecting the corresponding analytes at one or more locations in the cell or tissue sample. In some embodiments, for detecting the identifier sequences for a plurality of analytes that are sequenced in situ, the signals corresponding to at least two different identifier sequences are staggered between cycles. In some embodiments, the identifier sequences are decoded in base-by-base sequencing cycles using SBS or SBB or any other base-by-base sequencing chemistry (e.g., sequencing-by-avidity). In some embodiments, for many (e.g., most) of the base-by-base sequencing cycles, only signals associated with a limited number of analytes are detected in a particular cycle, whereas signals associated with many (e.g., most) other analytes are dark in that particular cycle. For instance, an analyte can be dark in a particular cycle when in that cycle, incorporation (e.g., in SBS) or binding (e.g., in SBB) of a cognate nucleotide that base pairs with a nucleotide in an identifier sequence for that analyte does not generate a detectable signal. In some embodiments, the cognate nucleotide comprises a base and is not detectably labeled (e.g., generating an OFF signal), whereas nucleotides comprising one or more other different bases are detectably labeled (e.g., each generating an ON signal).

In some embodiments, using a method disclosed herein, an ON signal is detected at a first location in a cell or tissue sample, and an OFF signal is detected at a second location in the cell or tissue sample. In some embodiments, the first and second locations do not overlap. In some embodiments, the first and second locations at least partially overlap. In some embodiments, the identifier sequences are such that only a subset of nucleotides in the identifier sequences to be detected in the same base-by-base sequencing cycle give rise to detectable signals, thereby limiting optical crowding of signals detected in that cycle.

Provided herein are methods involving the use of one or more polynucleotides (e.g., a circularizable probe such as a padlock probe) for analyzing one or more analytes(s) (e.g., one or more messenger RNAs) present in a cell or a biological sample, such as a tissue sample. Also provided are probes, sets of probes, compositions, kits, systems and devices for use in accordance with the provided methods. In some aspects, the provided methods and systems can be applied to sequence, detect, image, quantitate, and/or determine the presence of one or more analytes (e.g., target nucleic acid(s)) or portions thereof. In some aspects, the provided methods and systems can be applied to sequence in situ a plurality of analytes, or identifier sequences associated therewith, in parallel while simultaneously reducing optical crowding of generated signals in the sample.

In some embodiments, an exemplary workflow for analyzing a biological sample comprises contacting the biological sample with a first probe and a second probe, wherein the biological sample is a cell or tissue sample, the biological sample comprises a first analyte and a second analyte at a first location and a second location, respectively, in the biological sample, and wherein the first probe and the second probe directly or indirectly bind to the first analyte and the second analyte, respectively. In some embodiments, the first probe and the second probe undergo ligation, circularization and amplification to form a first product and a second product. In some aspects, the amplification is a rolling circle amplification and the product formed is a first rolling circle amplification product (RCP) and a second rolling circle amplification product. In some embodiments, the product of each probe is a rolling circle amplification (RCA) product generated in situ in the biological sample. In some embodiments, the first probe or product thereof comprises i) a first priming site for a first sequencing primer and ii) a first identifier sequence associated with the first analyte, and the second probe or product thereof comprises i) a second priming site for a second sequencing primer and ii) a second identifier sequence associated with the second analyte. In some embodiments, the first identifier sequence is a first barcode sequence or a complement thereof, and the second identifier sequence is a second barcode sequence or a complement thereof.

In some embodiments, an exemplary workflow for analyzing a biological sample comprises, performing base-by-base sequencing of the first and second identifier sequences using the first and second sequencing primers and a cyclic series of nucleotide incorporation or nucleotide binding steps, respectively, thereby generating a first signal code sequence and a second signal code sequence, each comprising a series of signal codes each corresponding to a signal (an ON signal), an absence of signal (an OFF signal), or a combination thereof detected in sequential cycles at the first location and the second location, respectively, wherein in one or more of the sequential cycles, an ON signal is detected at the first location and an OFF signal is detected at the second location. In some embodiments, the method comprises detecting the first and second identifier sequences in the biological sample based on the first and a second signal code sequences. In some embodiments, the method comprises detecting the amplification product or a portion thereof (e.g., RCA product) based on the first and a second signal code sequences. In some aspects, the first identifier sequence (e.g., barcode sequence) identifies the first analyte, and/or the second barcode sequence identifies the second analyte.

In some embodiments, an exemplary workflow for analyzing a biological sample comprises hybridizing the first sequencing primer to the first priming site and performing base-by-base sequencing to generate an extension product of the first sequencing primer and the first signal code sequence, removing (e.g., stripping), cleaving, or blocking (e.g., by use of a terminator nucleotide for the last cycles) the extension product of the first sequencing primer such that it is prevented from base-by-base sequencing, and hybridizing the second sequencing primer to the second priming site and performing base-by-base sequencing to generate an extension product of the second sequencing primer and the second signal code sequence. In some embodiments, the first priming site and the second priming site are different. In some embodiments, the probes or amplification products thereof for a first plurality of analytes share a common first priming site, and probes or amplification products thereof for a second plurality of analytes share a common second priming site. The second plurality of analytes may comprise two or more different analytes that are different from two or more different analytes of the first plurality of analytes.

In some embodiments, an exemplary workflow for analyzing a biological sample comprises contacting a biological sample with a plurality of probes each configured to directly or indirectly bind to a different analyte. In some embodiments, each probe, or rolling circle amplification product thereof, comprises a combination of two or more different priming sites. In some embodiments, the first probe or product thereof comprises a first combination of two or more different priming sites comprising the first priming site, and/or the second probe or product thereof comprises a second combination of two or more different priming sites comprising the second priming site. In some embodiments, the first combination of two or more different priming sites and the second combination of two or more different priming sites may share one or more common priming sites. In some embodiments, an exemplary workflow for analyzing a biological sample comprises contacting the biological sample with the first sequencing primer and performing base-by-base sequencing using a cyclic series of nucleotide incorporation or binding, respectively, thereby generating extension products of the first sequencing primer and detectable signal code sequences for a first plurality of analytes, removing, cleaving, or blocking the extension products of the first sequencing primer, and contacting the biological sample with the second sequencing primer and performing base-by-base sequencing using a cyclic series of nucleotide incorporation or binding, respectively, thereby generating extension products of the second sequencing primer and detectable signal code sequences for a second plurality of analytes that is different from the first plurality of analytes.

In some embodiments, an exemplary workflow for analyzing a biological sample comprises contacting the biological sample with a first probe and a second probe, wherein: the biological sample is a cell or tissue sample, the biological sample comprises a first analyte and a second analyte at a first location and a second location, respectively, in the biological sample, the first probe is provided in a first plurality of probes that directly or indirectly bind to the first analyte, the second probe is provided in a second plurality of probes that directly or indirectly bind to the second analyte, and wherein the first plurality of probes collectively comprise a first combination of barcode sequences and the second plurality of probes collectively comprise a second combination of barcode sequences. In some embodiments, the first and second plurality of probes comprise a first and second combination of priming sites for binding of a plurality of first and second sequencing primers. In some embodiments, the exemplary method comprises performing base-by-base sequencing of the first and second combination of barcode sequences using the plurality of first and second sequencing primers and a cyclic series of nucleotide incorporation or nucleotide binding steps, respectively, thereby generating a first signal code sequence and a second signal code sequence, each comprising a series of signal codes each corresponding to a signal (an ON signal), an absence of signal (an OFF signal), or a combination thereof detected in sequential cycles at the first location and the second location, respectively, wherein in one or more of the sequential cycles, an ON signal is detected at the first location and an OFF signal is detected at the second location. In some embodiments, the exemplary method comprises detecting the first and second combination of barcode sequences in the biological sample based on the first and second signal code sequences. In some embodiments, the first combination of barcode sequences identifies the first analytes and the second combination of barcode sequences identifies the second analytes.

II. Identifier Sequences

In some embodiments, provided herein are methods and compositions for analyzing a plurality of analytes in a sample by detecting identifier sequences for the analytes in the sample. In some embodiments, an identifier sequence is present in or derived from an analyte, e.g., a DNA or RNA analyte, in the sample. For instance, the identifier sequence can be part of the DNA or RNA analyte sequence. In some embodiments, the identifier sequence can be an analyte sequence (such as the arms of a padlock probe, or a gap filled sequence) or a complement thereof. In some embodiments, the analyte can comprise two or more different identifier sequences. In some embodiments, the analyte can comprise two or more copies of the same identifier sequence. In some embodiments, the different identifier sequences and/or copies of the same identifier sequence can be directly linked by a phosphodiester bond. In some embodiments, the different identifier sequences and/or copies of the same identifier sequence can be separated from one another by one or more nucleotide residues. In some embodiments, the different identifier sequences and/or copies of the same identifier sequence can partially overlap.

In some embodiments, an identifier sequence is present in a labeling agent, e.g., a nucleic acid probe, comprising the identifier sequence, or an antibody conjugated to a reporter oligonucleotide comprising the identifier sequence. In some embodiments, the labeling agent may include a binding moiety that directly or indirectly interacts (e.g., binds and/or reacts) with an analyte (e.g., an endogenous analyte in a sample). In some embodiments, the labeling agent can comprise a reporter oligonucleotide that is indicative of the analyte, or portion thereof, interacting with the binding moiety. For example, the reporter oligonucleotide may comprise a barcode sequence (as an identifier sequence) that permits identification of the binding moiety and the corresponding analyte. In some cases, the sample contacted by the labeling agent can be further contacted with a nucleic acid probe that hybridizes to the reporter oligonucleotide of the labeling agent. In some embodiments, the labeling agent comprises one or more barcode sequences, e.g., a barcode sequence that corresponds to the analyte binding moiety and/or the analyte. In some embodiments, a barcode sequence is associated with or otherwise identifies the analyte binding moiety. In some embodiments, by identifying an analyte binding moiety by identifying its associated barcode sequence, the analyte to which the analyte binding moiety binds can be identified. In some embodiments, a barcode sequence can be a nucleic acid sequence of a given length and/or a sequence that is associated with, corresponds to, and/or identifies the analyte binding moiety. A barcode sequence can generally include any of the variety of aspects of barcode sequences described herein, e.g., in Section II-B.

In some embodiments, an identifier sequence is present in a product of a DNA or RNA analyte in the sample. For instance, the identifier sequence can be present in a hybridization product, a ligation product, an extension product (e.g., by a DNA or RNA polymerase), a replication product, a transcription/reverse transcription product, and/or an amplification product such as a rolling circle amplification (RCA) product of a DNA or RNA analyte in the sample.

In some embodiments, an identifier sequence is present in a product of a labeling agent. In some embodiments, an identifier sequence is present in a product of a nucleic acid probe. In some embodiments, an identifier sequence is present in a product of a reporter oligonucleotide of a labeling agent. For instance, the identifier sequence can be present in a hybridization product, a ligation product, an extension product (e.g., by a DNA or RNA polymerase), a replication product, a transcription/reverse transcription product, and/or an amplification product such as a rolling circle amplification (RCA) product of a nucleic acid probe or reporter oligonucleotide in the sample.

In some embodiments, the product of a DNA or RNA analyte, a nucleic acid probe, and/or a reporter oligonucleotide in the sample can comprise two or more different identifier sequences. In some embodiments, the product can comprise two or more copies of the same identifier sequence. In some embodiments, the different identifier sequences and/or copies of the same identifier sequence can be in the same molecule or in different molecules (e.g., molecules that form a complex such as a branched structure via hybridization). In some embodiments, the different identifier sequences and/or copies of the same identifier sequence can be directly linked by a phosphodiester bond. In some embodiments, the different identifier sequences and/or copies of the same identifier sequence can be separated from one another by one or more nucleotide residues. In some embodiments, the different identifier sequences and/or copies of the same identifier sequence can partially overlap. A product can be generated in the sample (e.g., in situ), or at least a portion of a product can be generated outside the sample and then contacted with the sample. The product can be generated enzymatically and/or non-enzymatically. Exemplary products include but are not limited to RCA products, hybridization chain reaction (HCR) products, linear oligonucleotide hybridization chain reaction (LO-HCR) products, branched DNA reaction (bDNA) products, primer exchange reaction (PER) products, or products generated using any combination of these enzymatic and/or non-enzymatic reactions, e.g., as described in Section II-C.

An identifier sequence herein can be a contiguous sequence or comprise two or more sequences in the same molecule or in separate molecules. When in the same molecule, the two or more sequences can be separated by one or more nucleotide residues.

An identifier sequence herein can be of any suitable length. In some embodiments, the identifier sequence is between about 1 and about 500 nucleotides in length. In some embodiments, the identifier sequence is about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, or about 200 nucleotides in length, or of any integer (or range of integers) of nucleotides in between the indicated values.

In some embodiments, at a particular location of a cell or tissue sample, a molecule or complex comprises multiple copies of an identifier sequence that is associated with, corresponds to, and/or identifies an analyte at that particular location in the sample. In some embodiments, the multiple copies of the identifier sequence are detected using base-by-base sequencing, and the signals are used to identify the analyte. In some embodiments, the molecule or complex comprises at least 2, at least 5, at least 10, at least 15, at least 20, at least 25, or more different identifier sequences that are associated with, correspond to, and/or identify the analyte. In some embodiments, the molecule or complex comprises at least 2, at least 5, at least 10, at least 25, at least 50, at least 100, at least 250, at least 500, at least 1,000, at least 2,500, at least 5,000, or more copies of each of the one or more identifier sequences. Exemplary molecules and complexes comprising one or more different identifier sequences are described in Section II-C.

In some embodiments, a plurality of analytes are detected in the cell or tissue sample, and each analyte can be identified using an identifier sequence or a combination of identifier sequences. In some embodiments, the number of different analytes to be detected in the sample is at least 5, at least 10, at least 25, at least 50, at least 100, at least 250, at least 500, at least 1,000, at least 2,500, at least 5,000, or more. In some embodiments, the number of different identifier sequences used to identify the plurality of analytes in the sample is at least 5, at least 10, at least 25, at least 50, at least 100, at least 250, at least 500, at least 1,000, at least 2,500, at least 5,000, or more.

A. Identifier Sequences from Analytes

In some embodiments, an identifier sequence herein comprises an analyte sequence, an analyte-derived sequence, or a complement thereof. In some embodiments, the analyte comprises a nucleic acid sequence, and an identifier sequence comprises the nucleic acid sequence in the analyte or a complement of the nucleic acid sequence.

In some embodiments, the identifier sequence comprises a sequence of a viral or a cellular nucleic acid. In some embodiments, the identifier sequence comprises a sequence of a viral DNA or RNA. In some embodiments, the identifier sequence is in a virus or viral particle (e.g., in a cell or tissue sample) or from a virus or viral particle. In some embodiments, the identifier sequence comprises a sequence of a cellular DNA or RNA. In some embodiments, the cellular DNA or RNA is in a prokaryotic cell (e.g., in a tissue sample) or from a prokaryotic cell. In some embodiments, the cellular DNA or RNA is in a eukaryotic cell (e.g., in a tissue sample) or from a eukaryotic cell. In some embodiments, the identifier sequence comprises a sequence of a nucleic acid molecule in or from a nucleus, a mitochondrion, or a chloroplast. In some embodiments, the identifier sequence comprises a sequence of a genomic DNA, a cellular RNA, or a cDNA. In some embodiments, the identifier sequence comprises a sequence of a coding RNA and/or a non-coding RNA. In some embodiments, the identifier sequence comprises a sequence of a messenger RNA (mRNA), including a nascent RNA, a pre-mRNA, a primary-transcript RNA, and a processed RNA, such as a capped mRNA (e.g., with a 5' 7-methyl guanosine cap), a polyadenylated mRNA (poly-A tail at the 3' end), and a spliced mRNA in which one or more introns have been removed. In some embodiments, the identifier sequence comprises a sequence of a non-capped mRNA, a non-polyadenylated mRNA, or a non-spliced mRNA. In some embodiments, the identifier sequence comprises a sequence of a transcript of another nucleic acid molecule (e.g., DNA or RNA such as viral RNA) present in a cell or tissue sample. In some embodiments, the identifier sequence comprises a sequence of a non-coding RNA, and examples of a non-coding RNAs (ncRNA) that is not translated into a protein include transfer RNAs (tRNAs) and ribosomal RNAs (rRNAs), as well as small non-coding RNAs such as microRNA (miRNA), small interfering RNA (siRNA), Piwi-interacting RNA (piRNA), small nucleolar RNA (snoRNA), small nuclear RNA (snRNA), extracellular RNA (exRNA), small Cajal body-specific RNAs (scaRNAs), and the long ncRNAs such as Xist and HOTAIR. In some embodiments, the identifier sequence comprises a sequence of a small RNA (e.g., less than 200 nucleic acid bases in length) or a large RNA (e.g., RNA greater than 200 nucleic acid bases in length). Examples of small RNAs include 5.8S ribosomal RNA (rRNA), 5S rRNA, tRNA, miRNA, siRNA, snoRNAs, piRNA, tRNA-derived small RNA (tsRNA), and small rDNA-derived RNA (srRNA). The RNA can comprise double-stranded RNA or single-stranded RNA. The RNA can be circular RNA. The RNA can be a bacterial rRNA (e.g., 16s rRNA or 23s rRNA). In some embodiments, the identifier sequence comprises a sequence spanning an exon-exon junction, e.g., in a spliced RNA. In some embodiments, the identifier sequence comprises a sequence spanning an intron-exon or exon-intron junction, e.g., in a DNA or non-spliced RNA. In some embodiments, the identifier sequence can comprise a sequence of a reverse transcription product of any of the RNA disclosed herein. In some embodiments, the identifier sequence can comprise a cDNA of any of the RNA disclosed herein, or a complement of the cDNA.

In some embodiments, a nucleic acid analyte or a complement thereof is circularized, e.g., using template-independent ligation, and used as a template for rolling circle amplification (RCA). For instance, cDNAs produced from reverse transcription of mRNAs in a cell or tissue sample can be directly circularized using a single-stranded DNA ligase (e.g., a CircLigase™) and used as templates for RCA. In some cases, no prior knowledge of the mRNA is required and the direct-ligation approach can be used to sample the whole transcriptome in situ. The RCA products comprise complementary sequences of the cDNAs (that is, sequences of the mRNAs reverse transcribed to generate the cDNAs), which can be identifier sequences that are sequenced using a method disclosed herein in order to detect the corresponding mRNAs at locations in the cell or tissue sample.

In some embodiments, a circularizable probe or probe set is hybridized to a nucleic acid analyte (e.g., cDNA or mRNA) and ligated to form a circularized probe using the nucleic acid analyte as a template, with or without gap-filling prior to the ligation. In some embodiments, the circularizable probe or probe set comprises a 3' hybridization region and a 5' hybridization region (e.g., a 3' arm and a 5' arm) that are hybridized to the nucleic acid analyte (e.g., cDNA or mRNA). In some embodiments, upon hybridization to the nucleic acid analyte, a 3' terminal nucleotide and a 5' terminal nucleotide of the circularizable probe or probe set are configured to be ligated following gap-filling by a polymerase (e.g., an enzyme having a DNA polymerase or reverse transcriptase activity). In some embodiments, the 3'hybridization region and the 5' hybridization region of the circularizable probe or probe set are complementary to sequences in the nucleic acid analyte (e.g., cDNA or mRNA) that are not directly linked by a phosphodiester bond, and a gap of one or more nucleotides is formed between the two hybridization regions. In some embodiments, the gap is between about 1 and about 500 nucleotides in length. In some embodiments, the gap is about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, or about 200 nucleotides in length, or of any integer (or range of integers) of nucleotides in between the indicated values. In some embodiments, the gap is between about 200 and about 300, between about 300 and about 400, or between about 400 and about 500 nucleotides in length. In some embodiments, one or more gaps between 3' and 5' ends of the circularizable probe or probe set are formed upon hybridization to the nucleic acid analyte (e.g., cDNA or mRNA), for instance, two, three, or more gaps can be filled using the nucleic acid analyte as a template.

In some embodiments, the nucleic acid analyte is a DNA (e.g., cDNA) and the gap is filled by an enzyme having a DNA polymerase activity. In some embodiments, the nucleic acid analyte is an RNA (e.g., mRNA) and the gap is filled by an enzyme having a reverse transcriptase activity. In some embodiments, gap-filling by the enzyme copies a sequence of the nucleic acid analyte (e.g., cDNA or mRNA) into the circularized probe formed from the circularizable probe or probe set. In some embodiments, because the gap is flanked by known sequences, a method disclosed herein can be used to readout nucleic acid analyte sequences or complements thereof (e.g., "cellular barcodes") as identifier sequences of the nucleic acid analytes. For example, a known sequence 3' to an identifier sequence from a nucleic acid analyte can provide a priming site for binding by a sequencing primer disclosed herein, and the identifier sequence can be sequenced base-by-base.

In some embodiments, one or more barcode sequences can be built into the backbone of the circularizable probe or probe set, e.g., to differentiate among circularizable probes (e.g., padlock probes) targeting the same nucleic acid analyte or different nucleic acid analytes (e.g., cDNAs or mRNAs). In some embodiments, in addition to the identifier sequences (e.g., "cellular barcodes"), the one or more barcode sequences from the probe or probe set can also be readout using a base-by-base sequencing method disclosed herein. In some embodiments, in a circularized probe, a barcode sequence is adjacent to an identifier sequence generated using gap-filling (e.g., a sequence that is complementary to a sequence of the nucleic acid analyte), and both the barcode sequence and the identifier sequence can be sequenced in situ, for instance, by base-by-base sequencing of the corresponding sequences in an RCA product of the circularized probe. The adjacent barcode sequence and identifier sequence can be sequenced using the same sequencing primer, or using separate sequencing primers. In some embodiment, in the circularized probe, a 3' or 5' hybridization region sequence of the circularizable probe is between the adjacent barcode sequence and identifier sequence, and the 3' or 5' hybridization region sequence (a known sequence) can be used as a priming site or can be sequenced as a control.

Exemplary methods for generating circularized probes and RCA products thereof comprising identifier sequences derived from nucleic acid analytes (e.g., genomic DNA, mRNA, or cDNA) include but are not limited to those described in Chen et al., Efficient in situ barcode sequencing using padlock probe-based BaristaSeq, Nucleic Acid Research (2018) 46(4):e22; Lee et al., Fluorescent in situ sequencing (FISSEQ) of RNA for gene expression profiling in intact cells and tissues, Nature Protocols (2015) 10: 442-458; Lee et al., Highly multiplexed subcellular RNA sequencing in situ, Science (2014) 343:1360-1363; U.S. Pat. Nos. 10,138,509; 10,179,932; 10,494,662; 11,078,520; and 11,085,072, all of which are incorporated herein by reference.

B. Barcode Sequences as Identifier Sequences

In some embodiments, provided herein is a method comprising contacting a cell or tissue sample with a plurality of probes, each directly or indirectly binds to a different analyte in the sample. In some embodiments, each probe can comprise: i) a hybridization sequence (or analyte binding moiety, such as an antibody or antibody fragment) for direct or indirect binding to its corresponding analyte and ii) one or more identifier sequences that are associated with, correspond to, and/or identify the corresponding analyte. In some embodiments, the one or more identifier sequences are not derived from the corresponding analyte but are barcode sequences assigned to the corresponding analyte. In some instances, the assignment of identifier sequences to the corresponding analyte provides certain advantages over sequences of an endogenous analyte by allowing design of an identifier sequence that comprises the desired number and/or kind (e.g., A, T, C, or G) of nucleotides of which the majority (e.g., 70% or more) can be associated with an OFF signal. In some instances, using barcode sequences instead of sequences of endogenous analytes allows design of a plurality of barcode sequences which collectively reduce optical crowding of signals detected in the sequential decoding cycles (e.g., by having a sufficient number of "OFF" bases among the bases analyzed in the same cycle across the plurality of barcode sequences) and facilitate unambiguous analyte identification.

In some embodiments, in a barcode sequencing method, barcode sequences are detected for identification of other molecules including nucleic acid molecules (DNA or RNA) longer than the barcode sequences themselves, as opposed to direct sequencing of the longer nucleic acid molecules. In some embodiments, a N-mer barcode sequence comprises $4^N$ complexity given a sequencing read of N bases, and a much shorter sequencing read may be required for molecular identification compared to non-barcode sequencing methods such as direct sequencing. For example, 1024 molecular species may be identified using a 5-nucleotide barcode sequence ($4^5$=1024), whereas 8 nucleotide barcodes can be used to identify up to 65,536 molecular species, a number greater than the total number of distinct genes in the human genome. In some embodiments, the barcode sequences (e.g., contained in probes or RCA products) are detected, rather than endogenous sequences, which can be an efficient readout in terms of information per cycle of sequencing. In some embodiments, because the barcode sequences are pre-determined, they can also be designed to feature error detection and correction mechanisms, see, e.g., U.S. Pat. Pub.

20190055594 and U.S. Pat. Pub 20210164039, which are hereby incorporated by reference in their entirety.

In some aspects, an analyte can be associated with, correspond to, and/or be identified using one or more barcode sequence(s), e.g., at least two, three, four, five, six, seven, eight, nine, ten, or more different barcode sequences. Assignment of barcode sequences to analytes can be performed as described in Section III.

In some embodiments, a single barcode sequence can uniquely identify an analyte among multiple different analytes. In some embodiments, two or more different barcode sequences can be assigned to the same analyte, and any of the barcode sequences can uniquely identify an analyte among multiple different analytes. In some embodiments, a single barcode sequence is provided in a combination of barcode sequences, where the combination can uniquely identify an analyte among multiple different analytes. The combination of barcode sequences can be provided in two or more probe molecules. In some embodiments, the number of distinct barcode sequences in a population of nucleic acid probes is less than the number of distinct target analytes (e.g., nucleic acid analytes and/or protein analytes) of the nucleic acid probes, and yet the distinct target analytes may still be uniquely identified from one another, e.g., by encoding a probe with a different combination of barcode sequences. However, not all possible combinations of a given set of barcode sequences need be used. For instance, each probe may contain 1, 2, 3, 4, 5, 6, 7, 8, 9, 10, 11, 12, 13, 14, 15, etc. or more barcode sequences. In some embodiments, a population of, e.g., nucleic acid probes may each contain the same number of barcode sequences, although in other cases, there may be different numbers of barcode sequences present on the various probes.

As an illustrative example, a first probe may contain a first target-binding sequence (or first target-binding moiety), a first barcode sequence, and a second barcode sequence, while a second, different probe may contain a second target-binding sequence or target-binding moiety (that is different from the first target-binding sequence (or target binding moiety) in the first probe), the same first barcode sequence as in the first probe, but a third barcode sequence instead of the second barcode sequence. Such probes may thereby be distinguished by determining the various barcode sequence combinations present or associated with a given probe at a given location in a sample.

A barcode sequence can be attached to an analyte or to another moiety or structure in a reversible or irreversible manner. In some aspects, a barcode sequence can comprise about 4, 5, 6, 7, 8, 9, 10, 11, 12, 13, 14, 15, 16, 17, 18, 19, 20, 21, 22, 23, 24, 25, 26, 27, 28, 29, 30, or more than 30 nucleotides.

In some embodiments, a probe such as a nucleic acid probe (or a combination of nucleic acid probes configured to target the same analyte) may comprise 1, 2, 3, 4, 5, 6, 7, 8, 9, 10, 11, 12, 13, 14, 15 or more, 20 or more, 32 or more, 40 or more, or 50 or more different barcode sequences. In some embodiments, the nucleic acid probe or the combination of nucleic acid probes may comprise 1, 2, 3, 4, 5, 6, 7, 8, 9, 10, 11, 12, 13, 14, 15 or more, 20 or more, 32 or more, 40 or more, or 50 or more copies of a particular barcode sequence. The different barcode sequences or copies of the same barcode sequence may be positioned anywhere within the nucleic acid probe, or among the nucleic acid probes. If more than one barcode sequence or more than one copy is present, the barcode sequences or copies may be positioned next to each other, and/or interspersed with other sequences. In some embodiments, two or more of the barcode sequences or copies may also at least partially overlap. In some embodiments, two or more of the barcode sequences or copies in the same probe do not overlap. In some embodiments, any two or more or all of the barcode sequences or copies in the same probe can be separated from one another by at least a phosphodiester bond (e.g., they may be immediately adjacent to each other but do not overlap), such as 1, 2, 3, 4, 5, 6, 7, 8, 9, 10 or more nucleotides apart.

The barcode sequences may be of any length. In some embodiments, the barcode sequences may independently have the same or different lengths, such as at least 5, at least 6, at least 7, at least 8, at least 9, at least 10, at least 11, at least 12, at least 13, at least 14, at least 15, at least 20, at least 25, at least 30, at least 35, at least 40, at least 50 nucleotides in length. In some embodiments, an individual barcode sequence may be no more than 24, no more than 16, no more than 15, no more than 14, no more than 13, no more than 12, no more than 10, no more than 9, or no more than 8 nucleotides in length. Combinations of any of these are also possible, e.g., the barcode sequence may be between 5 and 10 nucleotides, between 8 and 15 nucleotides, etc.

In some embodiments, a barcode sequence can comprise two or more sub-barcode sequences that together function as a single barcode sequence. For example, a polynucleotide can comprise two or more polynucleotide sequences (e.g., sub-barcode sequences) that are separated by one or more non-barcode sequences. In some embodiments, a barcode sequence can also provide a platform for targeting functionalities, such as oligonucleotides, oligonucleotide-antibody conjugates, oligonucleotide-streptavidin conjugates, modified oligonucleotides, affinity purification, detectable moieties, enzymes, enzymes for detection assays or other functionalities, and/or for detection and identification of a polynucleotide comprising the barcode sequence or directly or indirectly binds to the barcode sequence.

The barcode sequence may be arbitrary or random. In certain cases, the barcode sequences are chosen so as to reduce or minimize homology with other components in a sample, e.g., such that the barcode sequences do not themselves bind to or hybridize with other nucleic acids suspected of being within the cell or other sample. In some embodiments, between a particular barcode sequence and another sequence (e.g., a cellular nucleic acid sequence in a sample or other barcode sequences in probes added to the sample), the homology may be less than 10%, less than 8%, less than 7%, less than 6%, less than 5%, less than 4%, less than 3%, less than 2%, or less than 1%. In some embodiments, the homology may be less than 20, 19, 18, 17, 16, 15, 14, 13, 12, 11, 10, 9, 8, 7, 6, 5, 4, 3, or 2 bases, and in some embodiments, the bases are consecutive bases.

In some embodiments, the nucleic acid probes disclosed herein and the barcode sequences in the probes may be made using only 2 or only 3 of the 4 bases, such as leaving out all the "G"s and/or leaving out all of the "C"s within the probe. Sequences lacking either "G"s or "C"s may form very little secondary structure, and can contribute to more uniform, faster hybridization in certain embodiments.

In some embodiments, the sets of signals detected during a cyclic in situ decoding process can be used to generate signal code sequences that correspond to the barcode sequences assigned to analytes, and the signal code sequences can be compared to code words in a codebook to identify matches. In some instances, the code words in a codebook may correspond to physical barcodes that comprise a series of ON and/or OFF bits corresponding to a series of ON and OFF signals detected in images acquired in sequential cycles during the decoding process. The presence and location of one or more target analytes may then be inferred from the detected signal code sequences and the detected locations of the corresponding ON and OFF signals for each signal code sequence at each particularly location in the series of images of the sample. In some aspects, a signal code of the signal code sequence may comprise, e.g., a signal (an ON signal), an absence of signal (an OFF signal), or a combination thereof.

A codebook comprising code words (corresponding to identifier sequences or "physical" nucleic acid barcode sequences) can be designed to meet a set of specific design criteria. For example, a codebook may be designed to ensure that it comprises a specified number (or minimum number) of unique code words/barcode sequences (e.g., corresponding to a specified number (or minimum number) of target analytes to be identified). In some instances, for example, a codebook may comprise at least 2, at least 5, at least 10, at least 20, at least 40, at least 60, at least 80, at least 100, at least 200, at least 400, at least 600, at least 800, at least 1,000, at least 2,000, at least 4,000, at least 6,000, at least 8,000, at least 10,000, at least 20,000, at least 40,000, at least 60,000, at least 80,000, at least 100,000, at least 200,000, at least 400,000, at least 600,000, at least 800,000, at least 1,000,000, at least $2\times10^6$, at least $3\times10^6$, at least $4\times10^6$, at least $5\times10^6$, at least $6\times10^6$, at least $7\times10^6$, at least $8\times10^6$, at least $9\times10^6$, at least $10^7$, at least $10^8$, at least $10^9$, or more than $10^9$ unique code words/barcode sequences. In some instances, a codebook may comprise any number of unique code words/barcode sequences within the range of values in this paragraph.

In some instances, the code words/barcode sequences in a given codebook may be designed to meet a specified pairwise edit distance (e.g., a specified minimum pairwise edit distance) so as to enable barcode error detection and correction. An "edit distance" is a numerical value that quantifies how different two strings (e.g., text strings) are from one another by counting the minimum number of editing operations required to transform one string into the other. Examples of edit distance metrics include, but are not limited to, Hamming distance, Levenshtein distance, longest common subsequence (LCS) distance, and the like. For example, the Levenshtein distance between two strings is the minimum number of single-character edits (e.g., insertions, deletions, or substitutions) required to transform one string into the other. The longest common subsequence (LCS) distance is the edit distance for which the only allowed edit operations are insertions and deletions, each of which is assigned a unit cost. The Hamming distance between two strings of equal length (e.g., substitutions are the only edit operations allowed) is the number of positions in the two strings at which the corresponding symbols are different.

Hamming distances and/or Levenshtein distances (where the error penalties assigned for differences between two strings are integer valued) allow for a natural interpretation of error correction, with minimum pairwise barcode distances of 2 k+1 allowing for correction of up to k errors. In some instances, the designed barcodes of a given codebook may be required to have a minimum pairwise edit distance (e.g., a minimum pairwise Hamming distance, a minimum pairwise Levenshtein distance, or a minimum pairwise LCS distance) such that they guarantee an error correction capability of correcting at least 1, at least 2, at least 3, at least 4, at least 5, at least 6, at least 7, at least 8, at least 9, or at least 10 barcode errors (e.g., errors arising during the decoding process).

In some instances, it is desirable to design the codebook so that optical crowding in the images used for decoding is minimized. For example, in some instances the set of code words/barcodes may be designed such that the ON signals (or combined weights) of the set of code words/barcodes are distributed more-or-less evenly over the plurality of decoding cycles. In some instances, the code words/barcodes in a codebook may be designed so that at most one bit is ON during any given decoding cycle. For example, the code words/barcodes in a codebook designed for use with a four "color" (e.g., four detection channel) decoding instrument may comprise a block of 4 bits (one for each detection channel) for each decoding cycle, where at most one bit is ON in any given cycle. The "color" described herein may include any color used in fluorescence microscopy, as well as a dark or OFF state (e.g., no detectable signal).

In some embodiments, the nucleotides within the barcode sequences corresponding to code words can be chosen to reduce optical crowding of signals detected in the cycles. For example, in a plurality of barcode sequences, the corresponding nucleotides that are to be detected in the same base-by-base sequencing cycle can be chosen to reduce optical crowding of signals detected in the cycle, and the plurality of barcode sequences can be designed such that optical crowding in multiple (e.g., a majority of) cycles is limited. In some embodiments, for every cycle in which a signal code (e.g., a signal of a first color, a signal of a second color, a signal of a third color, or an absence of signal) representing a nucleotide in a first barcode sequence is an ON signal, a signal code representing a corresponding nucleotide in a second barcode sequence is an OFF signal. In some embodiments, a dark or OFF state can be included in one or more code words/barcode sequences, and the nucleotide mixes for cyclic base-by-base sequencing are used to detect the dark or OFF state. In some embodiments, assignment of barcode sequences to each of a plurality of analytes is performed using any suitable schemes (e.g., as described in Section III.A).

C. Molecules or Complexes Comprising Identifier Sequences

Identifier sequences, including those from analytes and barcode sequences assigned to analytes, can be present in a variety of molecules or complexes thereof and detected using base-by-base sequencing in situ. Exemplary molecules and complexes are described herein.

(i) Labeling Agents

In the methods and systems described herein, one or more labeling agents capable of binding to or otherwise coupling to one or more features may be used to characterize analytes, cells and/or cell features. In some instances, cell features include cell surface features. Analytes may include, but are not limited to, a protein, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof. In some embodiments, the method comprises one or more post-fixing (also referred to as post-fixation) steps after contacting the sample with one or more labeling agents.

In some embodiments, a labeling agent comprises an analyte binding moiety capable of binding to an analyte (e.g., a biological analyte, e.g., a macromolecular constituent). A binding moiety may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The binding moiety can be directly or indirectly attached to a reporter oligonucleotide that is indicative of the analyte or feature to which the binding moiety binds. For example, the reporter oligonucleotide may comprise a barcode sequence that permits identification of the binding moiety and the corresponding analyte. For example, a labeling agent that is specific to one type of analyte or cell feature may have coupled thereto a first reporter oligonucleotide, while a labeling agent that is specific to a different analyte or cell feature may have a different reporter oligonucleotide coupled thereto. For a description of exemplary labeling agents, reporter oligonucleotides, and methods of use, see, e.g., U.S. Pat. No. 10,550,429; U.S. Pat. Pub. 20190177800; and U.S. Pat. Pub. 20190367969, which are each incorporated by reference herein in their entirety.

In some embodiments, an analyte binding moiety comprises one or more nucleic acid moieties. The one or more nucleic acid moieties can specifically bind to a target analyte, e.g., a target nucleic acid via nucleic acid hybridization. In some embodiments, an analyte binding moiety comprises one or more antibodies or epitope-binding fragments thereof. The antibodies or epitope-binding fragments including the analyte binding moiety can specifically bind to a target analyte. In some embodiments, the analyte is a protein (e.g., a protein on a surface of the biological sample (e.g., a cell) or an intracellular protein).

In some embodiments, a plurality of analyte labeling agents comprising a plurality of analyte binding moieties bind a plurality of analytes present in a biological sample. In some embodiments, the plurality of analytes includes a single species of analyte (e.g., a single species of polynucleotide or polypeptide). In some embodiments in which the plurality of analytes includes a single species of analyte, the analyte binding moieties of the plurality of analyte labeling agents are the same. In some embodiments in which the plurality of analytes includes a single species of analyte, the analyte binding moieties of the plurality of analyte labeling agents are different (e.g., members of the plurality of analyte labeling agents can have two or more species of analyte binding moieties, wherein each of the two or more species of analyte binding moieties binds a single species of analyte, e.g., at different binding sites). In some embodiments, the plurality of analytes includes multiple different species of analyte (e.g., multiple different species of polynucleotides or polypeptides).

In other instances, e.g., to facilitate sample multiplexing, different subsets of labeling agents that are specific to a particular analyte or cell feature may be used. For example, a first subset of labeling agents comprise binding moieties (e.g., a nucleic acid or an antibody or lipophilic moiety) coupled to a first reporter oligonucleotide, and a second subset of labeling agents comprise binding moieties coupled to a second reporter oligonucleotide which is different from the first reporter oligonucleotide.

In some aspects, these reporter oligonucleotides may comprise nucleic acid barcode sequences that permit identification of the binding moiety which the reporter oligonucleotide is coupled to. The selection of oligonucleotides as the reporter may provide advantages of being able to generate significant diversity in terms of sequence, while also being attachable to most biomolecules, e.g., nucleic acids and antibodies, etc., as well as being detectable, e.g., using the in situ detection techniques described herein.

Attachment (coupling) of the reporter oligonucleotides to the binding moieties may be achieved through any of a variety of direct or indirect, covalent or non-covalent associations or attachments. For example, oligonucleotides may be covalently attached to a portion of a binding moiety (such a protein, e.g., an antibody or antibody fragment) using chemical conjugation techniques (e.g., Lightning-Link® antibody labeling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31(2):708-715, which is entirely incorporated herein by reference for all purposes. Likewise, protein and peptide biotinylation techniques can be used. See, e.g., U.S. Pat. No. 6,265,552, which is entirely incorporated herein by reference for all purposes. Furthermore, click reaction chemistry may be used to couple reporter oligonucleotides to binding moieties. Commercially available kits, such as those from Thunderlink and Abcam, may be used to couple reporter oligonucleotides to binding moieties as appropriate. In another example, a binding moiety is indirectly (e.g., via hybridization) coupled to a reporter oligonucleotide comprising a barcode sequence that identifies the binding moiety. For instance, the binding moiety may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the binding moiety to the reporter oligonucleotide. In some embodiments, the reporter oligonucleotides are releasable from the binding moiety, such as upon application of a stimulus. For example, the reporter oligonucleotide may be attached to the binding moiety through a labile bond (e.g., chemically labile, photolabile, thermally labile, etc.).

In some embodiments, multiple different species of analytes (e.g., polynucleotides or polypeptides) from the biological sample can be subsequently associated with the one or more physical properties of the biological sample. For example, the multiple different species of analytes can be associated with locations of the analytes in the biological sample. Such information (e.g., proteomic information when the analyte binding moiety(ies) recognizes a polypeptide(s)) can be used in association with other spatial information (e.g., genetic information from the biological sample, such as DNA sequence information, transcriptome information (e.g., sequences of transcripts), or both). For example, a cell surface protein of a cell can be associated with one or more physical properties of the cell (e.g., a shape, size, activity, or a type of the cell). The one or more physical properties can be characterized by imaging the cell. The cell can be bound by an analyte labeling agent comprising an analyte binding moiety that binds to the cell surface protein and an analyte binding moiety barcode that identifies that analyte binding moiety. Results of protein analysis in a sample (e.g., a tissue sample or a cell) can be associated with DNA and/or RNA analysis in the sample.

(ii) Nucleic Acid Molecules and Complexes

In some aspects, binding of the one or more nucleic acid molecules (e.g., probes) to analytes in the biological sample may be direct or indirect. In some embodiments, the one or more nucleic acid molecules comprise a primary probe that binds directly to its corresponding analyte. In other embodiments, the one or more nucleic acid molecules comprise one or more probes that directly or indirectly bind to the primary probe. Identifier sequences can be present in nucleic acid molecules and complexes comprising one or more nucleic acid analytes and/or one or more nucleic acid probes that directly or indirectly bind to the nucleic acid analyte(s). The one or more identifier sequences in the nucleic acid molecules and complexes can be located downstream (5') of one or more priming sites for binding of one or more sequencing primers. The one or more identifier sequences can be associated with the analyte to which the primary probe is bound, and sequencing of the identifier sequences can enable identification of the analyte.

For instance, single molecule fluorescent in situ hybridization (smFISH) can be used to determine expression levels by detecting cellular nucleic acid analytes such as mRNAs. In smFISH, a set of typically 30-50 oligonucleotides, each about 20 nucleotides in length, can be hybridized to a complementary mRNA target. Individual transcripts are then visualized as diffraction-limited spots using wide-field epifluorescence microscopy, and quantified. In some embodiments, smFISH probes may carry, instead of a directly conjugated fluorescent label, a 10-30 nucleotide long overhang sequence, which is not hybridized to the mRNA target, and that can be detected by hybridization thereto of detectably (e.g., fluorescently) labeled probes. The overhang sequences in the smFISH probes may comprise one or more identifier sequences, e.g., barcode sequences. Thus, the smFISH probes and the mRNA target can form a nucleic acid complex comprising multiple barcode sequences that can be sequenced in situ base-by-base using a method disclosed herein.

Disclosed herein in some aspects are probes (e.g., first and/or second nucleic acid probes) that are introduced into a cell or used to otherwise contact a biological sample such as a tissue sample. The probes may comprise any of a variety of entities that can hybridize to a nucleic acid, typically by Watson-Crick base pairing, such as DNA, RNA, LNA, PNA, etc. The probes typically contain a targeting sequence or hybridization region that is able to directly or indirectly bind to at least a portion of a nucleic acid (e.g., target nucleic acid or a probe). For example, probes described herein may be able to bind to a specific target nucleic acid (e.g., an mRNA, or other nucleic acids as discussed herein). In some embodiments, the probes comprise one or more priming sites for binding of sequencing primers and one or more downstream identifier sequences that can be sequenced using the sequencing primers.

Any of the probes described herein can be linear probes. In some embodiments, a linear probe can be one that comprises an analyte-binding sequence (sometimes also referred to as a target recognition sequence). In some embodiments, the linear probe may comprise a sequence that does not hybridize to a target nucleic acid or target probe, such as a 5' overhang and/or a 3' overhang. In some embodiments, the sequence (e.g., the 5' overhang, 3' overhang) is non-hybridizing to the target nucleic acid or target probe but may hybridize to one another and/or one or more other probes to form hybridization complexes, e.g., those in hybridization chain reaction (HCR), branched DNA reaction, or the like. A hybridization complex can comprise one or more priming sites for binding of sequencing primers and one or more downstream identifier sequences that can be sequenced using the sequencing primers.

The analyte-binding sequence of a probe may be positioned anywhere within the probe. For instance, the analyte-binding sequence of a probe that binds to an analyte can be 5' or 3' to an identifier sequence (e.g., barcode sequence) in the probe. In some embodiments, the analyte-binding sequence of a probe can be 5' or 3' to a priming site or portion thereof in the probe. In some embodiments, the analyte-binding sequence may comprise a sequence that is substantially complementary to a portion of an analyte. In some embodiments, the portions may be at least 50%, at least 60%, at least 70%, at least 75%, at least 80%, at least 85%, at least 90%, at least 92%, at least 94%, at least 95%, at least 96%, at least 97%, at least 98%, at least 99%, or 100% complementary. The analyte-binding sequence of a probe may be determined with reference to a target analyte (e.g., a cellular RNA) that is present or suspected of being present in a sample. In some embodiments, more than one analyte-binding sequence can be used to identify a particular analyte comprising or associated with a target nucleic acid. The more than one analyte-binding sequence can be in the same probe or in different probes. For instance, multiple probes can be used, sequentially and/or simultaneously, that can bind to (e.g., hybridize to) different regions of the same target analyte or to different target analytes. In some embodiments, a first probe is provided in a first plurality of probes that directly or indirectly bind to a first analyte. In some embodiments, a second probe is provided in a second plurality of probes that directly or indirectly bind to a second analyte. The first and second analytes can be the same or different, and the first plurality of probes can be contacted with the sample, followed by detection of signals associated with the first plurality of probes, and contacting the sample with the second plurality of probes and detecting signals associated therewith.

In some embodiments, an identifier sequence (e.g., barcode sequence) can be on a single overhang of a probe provided herein (e.g., on an overhang of an L-shaped nucleic acid probe, or on one overhang of a U-shaped probe). In other embodiments, barcode sequences can be positioned on two overhang regions of the probe (e.g., both 5' and 3' overhangs of a U-shaped probe). In some embodiments, a barcode sequence of an individual probe is associated with the analyte and uniquely identifies the analyte. In other embodiments, a combination of the barcode sequences of multiple probes that hybridize to the same target analyte uniquely identify the target analyte. For example, the first probe is provided in a first plurality of probes that directly or indirectly bind to the first analyte. In some aspects, the first plurality of probes collectively comprise a first combination of barcode sequences and the first combination of barcode sequences identifies the first analyte. In some embodiments, the second probe is provided in a second plurality of probes that directly or indirectly bind to the second analyte. In some aspects, the second plurality of probes collectively comprise a second combination of barcode sequences and the second combination of barcode sequences identifies the second analyte. In some embodiments, dividing the barcode sequences that identify a target analyte among multiple probes (e.g., a plurality of primary probes that) can decrease the length requirements for the probes (e.g., first probes).

In some embodiments, an identifier sequence (e.g., barcode sequence) can be in a primary probe, e.g., a primary probe that directly hybridizes to a cellular nucleic acid molecule such as an mRNA, or in a product (e.g., an RCA product) of the primary probe. In some embodiments, the primary probe can comprise a 3' or 5' overhang upon hybridization to the cellular nucleic acid molecule. In some embodiments, the 3' or 5' overhang comprises one or more barcode sequences. In some embodiments, the primary probe can comprise a 3' overhang and a 5' overhang upon hybridization to the cellular nucleic acid molecule. In some embodiments, the 3' overhang and the 5' overhang each independently comprises one or more barcode sequences. In some embodiments, the primary probe can be a circular primary probe. In some embodiments, the circular primary probe comprises one or more barcode sequences outside the analyte-binding sequence of the probe. In some embodiments, the primary probe can be a circularizable primary probe or probe set. In some embodiments, the circularizable primary probe or probe set comprises one or more barcode sequences outside the analyte-binding sequence of the probe or probe set. In some embodiments, the primary probe can comprise a split hybridization region configured to hybridize to a splint. In some embodiments, the split hybridization region comprises one or more barcode sequences. In some embodiments, the primary probe comprises one or more barcode sequences outside the analyte-binding sequence and the split hybridization region of the primary probe.

In some embodiments, an identifier sequence (e.g., barcode sequence) can be in a probe that indirectly binds to a cellular nucleic acid molecule such as an mRNA, or in a product (e.g., an RCA product) of the probe. In some embodiments, the probe can be an intermediate probe that bridges the binding of a probe (e.g., a primary probe) or product thereof and another probe or product thereof. In some embodiments, the probe can be a detection probe that hybridizes to a primary probe or intermediate probe or product thereof but does not directly or indirectly bind to any other probe. The detection probe can further comprise a priming site for sequencing the identifier sequence in the detection probe using a method disclosed herein.

In some embodiments, the intermediate or detection probe can comprise a 3' or 5' overhang upon hybridization to another probe. In some embodiments, the 3' or 5' overhang comprises one or more barcode sequences. In some embodiments, the intermediate or detection probe can comprise a 3' overhang and a 5' overhang upon hybridization to another probe. In some embodiments, the 3' overhang and the 5' overhang each independently comprises one or more barcode sequences. In some embodiments, the intermediate or detection probe can be a circular probe. In some embodiments, the circular probe comprises one or more barcode sequences outside the target-binding sequence of the probe. In some embodiments, the intermediate or detection probe can be a circularizable probe or probe set. In some embodiments, the circularizable probe or probe set comprises one or more barcode sequences outside the target-binding sequence of the probe or probe set. In some embodiments, the intermediate or detection probe can comprise a split hybridization region configured to hybridize to a splint. In some embodiments, the split hybridization region can comprise a priming site and the splint or a portion thereof can be used a sequencing primer to sequence the identifier sequence in the intermediate or detection probe using a method disclosed herein. Exemplary probes comprising split hybridization regions include but are not limited to those described in US 2022/0049302, incorporated herein by reference in its entirety. In some embodiments, the split hybridization region comprises one or more barcode sequences. In some embodiments, the intermediate or detection probe comprises one or more barcode sequences outside the target-binding sequence and the split hybridization region of the probe.

In some embodiments, an identifier sequence (e.g., barcode sequence) can be in a rolling circle amplification (RCA) product molecule, a complex comprising an initiator and an amplifier for hybridization chain reaction (HCR), a complex comprising an initiator and an amplifier for linear oligonucleotide hybridization chain reaction (LO-HCR), a primer exchange reaction (PER) product molecule, a complex comprising a pre-amplifier and an amplifier for branched DNA (bDNA), or a complex comprising any two or more of the aforementioned molecules and complexes. For example, a bDNA complex or an HCR complex can be assembled on an RCA product. See, e.g., US 2021/0198727, incorporated herein by reference in its entirety. A priming site can be provided 3' of each identifier sequence in the molecule or complex for sequencing the identifier sequence in situ using SBS, SBB, or any other base-by-base sequencing method.

In some embodiments, a molecule or complex comprising identifier sequences (e.g., barcode sequences) and priming sites for sequencing the identifier sequences can be generated using targeted assembly of branched structures (e.g., bDNA or branched assay using locked nucleic acid (LNA)), programmed in situ growth of concatemers by enzymatic rolling circle amplification (RCA) (e.g., as described in US 2019/0055594 incorporated herein by reference), HCR or the like, assembly of topologically catenated DNA structures using serial rounds of chemical ligation (clampFISH), hairpin-mediated concatemerization (e.g., as described in US 2020/0362398 incorporated herein by reference), e.g., primer exchange reactions such as signal amplification by exchange reaction (SABER) or SABER with DNA-Exchange (Exchange-SABER). In some embodiments, a non-enzymatic method may be used.

Figure 2:
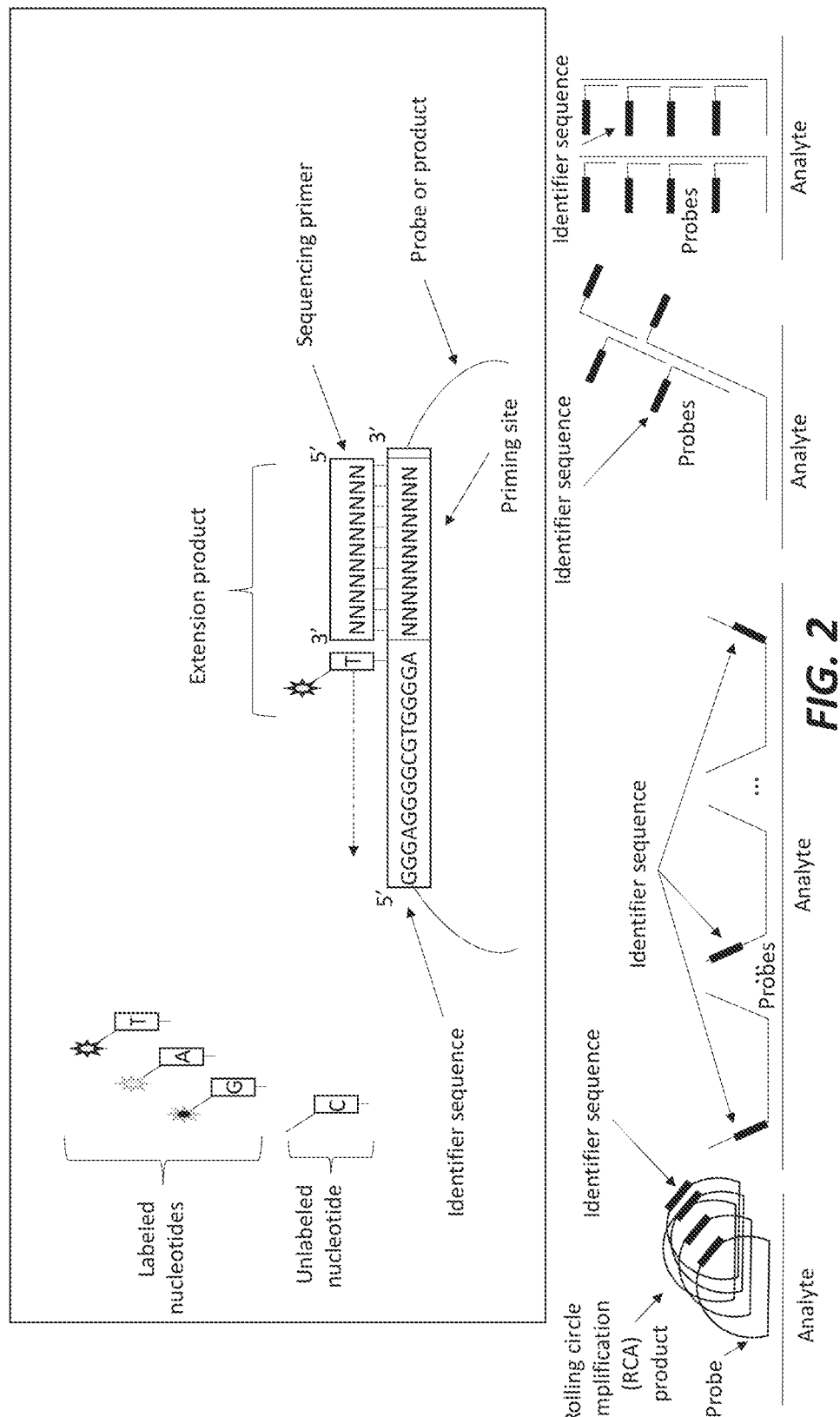
FIG. 2 depicts exemplary molecules and complexes comprising a priming site and a downstream identifier sequence (e.g., barcode sequence GGGAGGGGCGTGGGGA (SEQ ID NO: 3)) that can be analyzed using base-by-base sequencing (e.g., SBS or SBB) in situ. A rolling circle amplification product, probes tiled on an analyte, a hybridization chain reaction complex, and a branched structure are shown as examples (bottom panel, from left to right). Each molecule or complex can comprise multiple copies of the identifier sequence and a 3' priming site for sequencing primer binding.

In some embodiments, a complex comprising identifier sequences (e.g., barcode sequences) and priming sites comprises an amplifier hybridized directly or indirectly (via one or more oligonucleotides) to a sequence of a nucleic acid analyte, a probe directly or indirectly targeting the nucleic acid analyte, or a product of the nucleic acid analyte or probe, e.g., as shown in FIG. 2. In some embodiments, the assembly includes one or more amplifiers each including an amplifier repeating sequence. In some aspects, the one or more amplifiers is labeled. In some aspects, the one or more amplifiers is not labeled. For exemplary complexes, see e.g., US 2020/0399689 and US 2022/0064697, which are fully incorporated by reference herein.

In some embodiments, a complex comprising identifier sequences (e.g., barcode sequences) and priming sites comprises an HCR complex, e.g., as shown in FIG. 2. HCR is an enzyme-free nucleic acid amplification based on a triggered chain of hybridization of nucleic acid molecules starting from HCR monomers, which hybridize to one another to form a nicked nucleic acid polymer. This polymer is the product of the HCR reaction which is ultimately detected in order to indicate the presence of the target analyte. HCR is described in detail in Dirks and Pierce, 2004, PNAS, 101 (43), 15275-15278 and in U.S. Pat. Nos. 7,632,641 and 7,721,721 (see also US 2006/00234261; Chemeris et al, 2008 Doklady Biochemistry and Biophysics, 419, 53-55; Niu et al, 2010, 46, 3089-3091; Choi et al, 2010, Nat. Biotechnol. 28(11), 1208-1212; and Song et al, 2012, Analyst, 137, 1396-1401). HCR monomers typically comprise a hairpin, or other metastable nucleic acid structure. In the simplest form of HCR, two different types of stable hairpin monomer, referred to here as first and second HCR monomers, undergo a chain reaction of hybridization events to form a long nicked double-stranded DNA molecule when an "initiator" nucleic acid molecule is introduced. The HCR monomers have a hairpin structure comprising a double stranded stem region, a loop region connecting the two strands of the stem region, and a single stranded region at one end of the double stranded stem region. The single stranded region which is exposed (and which is thus available for hybridization to another molecule, e.g. initiator or other HCR monomer) when the monomers are in the hairpin structure may be known as the "toehold region" (or "input domain"). The first HCR monomers each further comprise a sequence which is complementary to a sequence in the exposed toehold region of the second HCR monomers. This sequence of complementarity in the first HCR monomers may be known as the "interacting region" (or "output domain"). Similarly, the second HCR monomers each comprise an interacting region (output domain), e.g. a sequence which is complementary to the exposed toehold region (input domain) of the first HCR monomers. In the absence of the HCR initiator, these interacting regions are protected by the secondary structure (e.g. they are not exposed), and thus the hairpin monomers are stable or kinetically trapped (also referred to as "metastable"), and remain as monomers (e.g. preventing the system from rapidly equilibrating), because the first and second sets of HCR monomers cannot hybridize to each other. However, once the initiator is introduced, it is able to hybridize to the exposed toehold region of a first HCR monomer, and invade it, causing it to open up. This exposes the interacting region of the first HCR monomer (e.g. the sequence of complementarity to the toehold region of the second HCR monomers), allowing it to hybridize to and invade a second HCR monomer at the toehold region. This hybridization and invasion in turn opens up the second HCR monomer, exposing its interacting region (which is complementary to the toehold region of the first HCR monomers), and allowing it to hybridize to and invade another first HCR monomer. The reaction continues in this manner until all of the HCR monomers are exhausted (e.g. all of the HCR monomers are incorporated into a polymeric chain). Ultimately, this chain reaction leads to the formation of a nicked chain of alternating units of the first and second monomer species. The presence of the HCR initiator is thus required in order to trigger the HCR reaction by hybridization to and invasion of a first HCR monomer. The first and second HCR monomers are designed to hybridize to one another are thus may be defined as cognate to one another. They are also cognate to a given HCR initiator sequence. HCR monomers which interact with one another (hybridize) may be described as a set of HCR monomers or an HCR monomer, or hairpin, system.

An HCR reaction could be carried out with more than two species or types of HCR monomers. For example, a system involving three HCR monomers could be used. In such a system, each first HCR monomer may comprise an interacting region which binds to the toehold region of a second HCR monomer; each second HCR may comprise an interacting region which binds to the toehold region of a third HCR monomer; and each third HCR monomer may comprise an interacting region which binds to the toehold region of a first HCR monomer. The HCR polymerization reaction would then proceed as described above, except that the resulting product would be a polymer having a repeating unit of first, second and third monomers consecutively. Corresponding systems with larger numbers of sets of HCR monomers can be used.

In some embodiments, the HCR product (e.g., a nicked chain of alternating units of monomer species) can comprise multiple overhangs that each comprises one or more identifier sequences (e.g., barcode sequences) and priming sites for sequencing the identifier sequences in situ. Thus, HCR as used herein does not require the use of detectably labeled HCR monomers; rather, one or more HCR monomer may comprise one or more identifier sequences (e.g., barcode sequences), and detection of the HCR product comprises sequencing the identifier sequences in situ.

In some embodiments, similar to HCR reactions that use hairpin monomers, linear oligo hybridization chain reaction (LO-HCR) can also be used for generating a complex comprising identifier sequences (e.g., barcode sequences) and priming sites for sequencing the identifier sequences. In some embodiments, provided herein is a method of detecting an analyte in a sample comprising: (i) performing a linear oligo hybridization chain reaction (LO-HCR), wherein an initiator is contacted with a plurality of LO-HCR monomers of at least a first and a second species to generate a polymeric LO-HCR product hybridized to a target nucleic acid molecule, wherein the first species comprises a first hybridization region complementary to the initiator and a second hybridization region complementary to the second species, wherein the first species and the second species are linear, single-stranded nucleic acid molecules; wherein the initiator is provided in one or more parts, and hybridizes directly or indirectly to or is comprised in the target nucleic acid molecule; and (ii) detecting the polymeric product, thereby detecting the analyte. In some embodiments, the first species and/or the second species may not comprise a hairpin structure. In some embodiments, the plurality of LO-HCR monomers may not comprise a metastable secondary structure. In some embodiments, the LO-HCR polymer may not comprise a branched structure. In some embodiments, performing the linear oligo hybridization chain reaction comprises contacting the target nucleic acid molecule with the initiator to provide the initiator hybridized to the target nucleic acid molecule. Exemplary methods and compositions for LO-HCR are described in US 2021/0198723, incorporated herein by reference in its entirety.

In some embodiments, the polymeric product in LO-HCR can comprise multiple overhangs that each comprises one or more identifier sequences (e.g., barcode sequences) and priming sites for sequencing the identifier sequences in situ. Thus, LO-HCR as used herein does not require the use of detectably labeled LO-HCR monomers; rather, one or more LO-HCR monomer may comprise one or more identifier sequences (e.g., barcode sequences), and detection of the LO-HCR product comprises sequencing the identifier sequences in situ.

In some embodiments, a molecule (e.g., a concatemer molecule) comprising identifier sequences (e.g., barcode sequences) and priming sites is generated by a primer exchange reaction (PER). In various embodiments, a primer with domain on its 3' end binds to a catalytic hairpin, and is extended with a new domain by a strand displacing polymerase. In various embodiments, the strand displacing polymerase is a Bst polymerase. In various embodiments, the catalytic hairpin includes a stopper which releases the strand displacing polymerase. In various embodiments, branch migration displaces the extended primer, which can then dissociate. In various embodiments, the primer undergoes repeated cycles to form a concatemer molecule, see e.g., US 2019/0106733, which is incorporated herein by reference, for exemplary molecules and PER reaction components. In various embodiments, the concatemer molecule comprises multiple copies of one or more identifier sequences (e.g., barcode sequences) and priming sites for sequencing the identifier sequences. Thus, instead of hybridizing a plurality of labeled oligonucleotide probes to concatemer molecule, the concatemer molecule can be detected by sequencing the identifier sequences in situ.

(iii) Rolling Circle Amplification (RCA) Products

In some embodiments, a molecule (e.g., a concatemer molecule) comprising identifier sequences (e.g., barcode sequences) and priming sites is generated by RCA of a circular nucleic acid molecule, e.g., as shown in FIG. 2. As described in Section II-A, a nucleic acid analyte (e.g., cDNA) can be circularized to generate the circular nucleic acid molecule and the RCA product comprises identifier sequences derived from the nucleic acid analyte. In some embodiments, any suitable circularizable probe or probe set disclosed herein can be circularized, e.g., using a nucleic acid analyte or a probe as a template, with or without gap-filling prior to the circularization. The RCA product may comprise barcode sequences or complements thereof that can be sequenced in situ.

In some aspects, the probes disclosed herein (e.g., primary probes, intermediate probes, detection probes, etc.) are ligated to form a circular construct (e.g., circular probe). In some embodiments, the circular construct is formed using template primer extension followed by ligation. In some embodiments, a ligated probe is generated using the analyte as template. In some embodiments, the circular construct is formed by providing an insert between ends to be ligated. In some embodiments, the circular construct is formed using a combination of any one of the foregoing. In some embodiments, the ligation is a DNA templated ligation. In some embodiments, the ligation is an RNA templated ligation. In some embodiments, a splint is provided as a template for ligation.

The nature of the ligation reaction depends on the structural components of the probes used. In some embodiments, the 3' end and a 5' end of the circularizable probe or probe set can be ligated using the analyte (e.g., RNA) as a template. In some embodiments, the 3' end and the 5' end are ligated without gap filling prior to ligation. In some embodiments, the ligation of the 3' end and the 5' end is preceded by gap filling. The gap may be 1, 2, 3, 4, 5, or more nucleotides. In some embodiments, ligation may comprise enzymatic ligation, chemical ligation, template dependent ligation, and/or template independent ligation. In any one of the embodiments herein, the ligation can comprise using a ligase having an RNA-templated DNA ligase activity and/or an RNA-templated RNA ligase activity. In some embodiments, the enzymatic ligation involves use of a ligase (e.g., an RNA ligase, a DNA ligase). Ligases comprise ATP-dependent double-strand polynucleotide ligases, NAD-i-dependent double-strand DNA or RNA ligases and single-strand polynucleotide ligases, for example any one of the ligases described in EC 6.5.1.1 (ATP-dependent ligases), EC 6.5.1.2 (NAD+-dependent ligases), EC 6.5.1.3 (RNA ligases). Specific examples of ligases comprise bacterial ligases such as E. coli DNA ligase, Tth DNA ligase, *Thermococcus* sp. (strain 9° N) DNA ligase (9° N™ DNA ligase, New England Biolabs), Taq DNA ligase, Ampligase™ (Epicentre Biotechnologies) and phage ligases such as T3 DNA ligase, T4 DNA ligase and T7 DNA ligase and mutants thereof. In any one of the embodiments herein, the ligation can comprise using a ligase selected from the group consisting of a *Chlorella* virus DNA ligase (PBCV DNA ligase), a T4 RNA ligase, a T4 DNA ligase, and a single-stranded DNA (ssDNA) ligase. In any one of the embodiments herein, the ligation can comprise using a PBCV-1 DNA ligase or variant or derivative thereof and/or a T4 RNA ligase 2 (T4 Rnl2) or variant or derivative thereof. In some embodiments, the ligase is a T4 RNA ligase. In some embodiments, the ligase comprises a splintR ligase. In some embodiments, the ligase is a single stranded DNA ligase. In some embodiments, the ligase is a T4 DNA ligase. In some embodiments, the ligase is a ligase that has an DNA-splinted DNA ligase activity. In some embodiments, the ligase is a ligase that has an RNA-splinted DNA ligase activity.

In some aspects, a high fidelity ligase, such as a thermostable DNA ligase (e.g., a Taq DNA ligase), is used. Thermostable DNA ligases are active at elevated temperatures, allowing further discrimination by incubating the ligation at a temperature near the melting temperature of the DNA strands. High-fidelity ligation can be achieved through a combination of the intrinsic selectivity of the ligase active site and balanced conditions to reduce the incidence of annealed mismatched dsDNA.

In some embodiments, a removing step is performed to remove molecules that are not specifically hybridized. In some embodiments, the removing step is performed to remove unligated probes. In some embodiments, the removing step is performed after ligation and prior to amplification. Washing steps can be performed at any point during the process to remove non-specifically bound probes, probes that have not ligated, etc. In some embodiments, the circularized probe remains specifically hybridized to the analyte after the removing step.

In some instances, a primer oligonucleotide is added for amplification. In some instances, the primer oligonucleotide is added with the circularizable probe or probe set. In some instances, the primer oligonucleotide is added before or after the circularizable probe or probe set is contacted with the sample. In some instances, the primer oligonucleotide for amplification of the circularized nucleic acid molecule may comprise a sequence complementary to a nucleic acid (e.g., a cDNA or mRNA), as well as a sequence complementary to the circularizable probe that hybridizes to the nucleic acid. In some embodiments, a washing step is performed to remove any unbound probes, primers, etc. In some embodiments, the wash is a stringency wash.

A primer oligonucleotide for amplification of the circularized nucleic acid molecule can comprise a single-stranded nucleic acid sequence having a 3' end that can be used as a substrate for a nucleic acid polymerase in a nucleic acid extension reaction. The primer oligonucleotide can comprise both RNA nucleotides and DNA nucleotides (e.g., in a random or designed pattern). The primer oligonucleotide can also comprise other natural or synthetic nucleotides described herein that can have additional functionality. The primer oligonucleotide can be about 6 bases to about 100 bases, such as about 25 bases.

In some instances, upon addition of a DNA polymerase in the presence of appropriate dNTP precursors and other cofactors, the amplification primer is elongated by replication of multiple copies of the template. The amplification step can utilize isothermal amplification or non-isothermal amplification. In some embodiments, after the formation of the hybridization complex and any subsequent circularization (such as ligation of, e.g., a padlock probe) the circularized nucleic acid molecule is rolling-circle amplified to generate a RCA product (e.g., amplicon) containing multiple copies of the sequence of the circularized nucleic acid molecule. See, e.g., Baner et al, Nucleic Acids Research, 26:5073-5078, 1998; Lizardi et al, Nature Genetics 19:226, 1998; Mohsen et al., Acc Chem Res. 2016 Nov. 15; 49(11): 2540-2550; Schweitzer et al. Proc. Natl Acad. Sci. USA 97:10113-119, 2000; Faruqi et al, BMC Genomics 2:4, 2000; Nallur et al, Nucl. Acids Res. 29:e118, 2001; Dean et al. Genome Res. 11:1095-1099, 2001; Schweitzer et al, Nature Biotech. 20:359-365, 2002; U.S. Pat. Nos. 6,054,274, 6,291,187, 6,323,009, 6,344,329 and 6,368,801, all of which are incorporated herein by reference.

In some embodiments, rolling circle amplification products are generated using a polymerase selected from the group consisting of Phi29 DNA polymerase, Phi29-like DNA polymerase, M2 DNA polymerase, B103 DNA polymerase, GA-1 DNA polymerase, phi-PRD1 polymerase, Vent DNA polymerase, Deep Vent DNA polymerase, Vent (exo-) DNA polymerase, KlenTaq DNA polymerase, DNA polymerase I, Klenow fragment of DNA polymerase I, DNA polymerase III, T3 DNA polymerase, T4 DNA polymerase, T5 DNA polymerase, T7 DNA polymerase, Bst polymerase, rBST DNA polymerase, N29 DNA polymerase, TopoTaq DNA polymerase, T7 RNA polymerase, SP6 RNA polymerase, T3 RNA polymerase, and a variant or derivative thereof. In some embodiments, the polymerase is Phi29 DNA polymerase.

In some embodiments, the polymerase comprises a modified recombinant Phi29-type polymerase. In some embodiments, the polymerase comprises a modified recombinant Phi29, B103, GA-1, PZA, Phi15, BS32, M2Y, Nf, G1, Cp-1, PRD1, PZE, SF5, Cp-5, Cp-7, PR4, PR5, PR722, or L17 polymerase. In some embodiments, the polymerase comprises a modified recombinant DNA polymerase having at least one amino acid substitution or combination of substitutions as compared to a wildtype Phi29 polymerase. Exemplary polymerases are described in U.S. Pat. Nos. 8,257,954; 8,133,672; 8,343,746; 8,658,365; 8,921,086; and 9,279,155, all of which are herein incorporated by reference. In some embodiments, the polymerase is not directly or indirectly immobilized to a substrate, such as a bead or planar substrate (e.g., glass slide), prior to contacting a sample, although the sample may be immobilized on a substrate.

In some embodiments, the amplification is performed at a temperature between or between about 20° C. and about 60° C. In some embodiments, the amplification is performed at a temperature between or between about 30° C. and about 40° C. In some aspects, the amplification is performed at a temperature between at or about 25° C. and at or about 50° C., such as at or about 25° C., 27° C., 29° C., 31° C., 33° C., 35° C., 37° C., 39° C., 41° C., 43° C., 45° C., 47° C., or 49° C.

In any one of the embodiments herein, the RCA products can be generated in situ in the biological sample. In any one of the embodiments herein, the product can be generated using a linear RCA, a branched RCA, a dendritic RCA, or any combination thereof.

In some embodiments, the RCA product comprises multiple copies of one or more identifier sequences or complementary sequences thereof. In some embodiments, the RCA product comprises multiple copies of one of more priming sites or complementary sequences thereof. In some aspects, the one or more identifier sequences or complementary sequences thereof are located downstream of the one or more priming sequences or complementary sequences thereof.

In some aspects, during the amplification step, modified nucleotides can be added to the reaction to incorporate the modified nucleotides in the amplification product (e.g., nanoball). Exemplary of the modified nucleotides comprise amine-modified nucleotides. In some aspects of the methods, for example, for anchoring or cross-linking of the generated amplification product (e.g., nanoball) to a scaffold, to cellular structures and/or to other amplification products (e.g., other nanoballs). In some aspects, the amplification products comprises a modified nucleotide, such as an amine-modified nucleotide. In some embodiments, the amine-modified nucleotide reacts with an acrylic acid N-hydroxysuccinimide moiety. Examples of other amine-modified nucleotides comprise, but are not limited to, a 5-Aminoallyl-dUTP moiety modification, a 5-Propargylamino-dCTP moiety modification, a $N^6$-6-Aminohexyl-dATP moiety modification, or a 7-Deaza-7-Propargylamino-dATP moiety modification. In some embodiments, the modified nucleotides comprises base modifications, such as azide and/or alkyne base modifications, dibenzylcyclooctyl (DBCO) modifications, vinyl modifications, trans-Cyclooctene (TCO), and so on.

In some embodiments, the primer extension reaction mixture can comprise a deoxynucleoside triphosphate (dNTP) or derivative, variant, or analogue thereof. In some embodiments, the primer extension reaction mixture can comprise a catalytic cofactor of the polymerase. In any of the preceding embodiments, the primer extension reaction mixture can comprise a catalytic di-cation, such as $Mg^{2+}$ and/or $Mn^{2+}$.

In some aspects, the amplification product (e.g., RCA product) can be anchored to a polymer matrix. The amplification products may be immobilized within the matrix generally at the location of the nucleic acid being amplified, thereby creating a localized colony of amplicons. The amplification products may be immobilized within the matrix by steric factors. The amplification products may also be immobilized within the matrix by covalent or noncovalent bonding. In this manner, the amplification products may be considered to be attached to the matrix. By being immobilized to the matrix, such as by covalent bonding or cross-linking, the size and spatial relationship of the original amplicons is maintained. By being immobilized to the matrix, such as by covalent bonding or cross-linking, the amplification products are resistant to movement or unraveling under mechanical stress.

In some aspects, the amplification products (e.g., RCA products) are copolymerized and/or covalently attached to the surrounding matrix thereby preserving their spatial relationship and any information inherent thereto. In some embodiments, the RCA products are generated from DNA or RNA within a cell embedded in the matrix. In some embodiments, the RCA products can also be functionalized to form covalent attachment to the matrix preserving their spatial information within the cell thereby providing a subcellular localization distribution pattern. In some embodiments, the provided methods involve embedding RCA products in the presence of hydrogel subunits to form one or more hydrogel-embedded amplification products. In some embodiments, the hydrogel-tissue chemistry described comprises covalently attaching nucleic acids to in situ synthesized hydrogel for tissue clearing, enzyme diffusion, and multiple-cycle sequencing or probe hybridization while an existing hydrogel-tissue chemistry method cannot. In some embodiments, to enable amplification product embedding in the tissue-hydrogel setting, amine-modified nucleotides are comprised in the amplification step (e.g., RCA), functionalized with an acrylamide moiety using acrylic acid N-hydroxysuccinimide esters, and copolymerized with acrylamide monomers to form a hydrogel.

III. In Situ Sequencing of Identifier Sequences

In some embodiments, provided herein is a method of analyzing a cell or tissue sample, comprising contacting the sample with a probe that directly or indirectly binds to an analyte at a location in the sample, wherein the probe or a product (e.g., an amplification product such as an RCA product) thereof comprises a priming site and an identifier sequence present in, associated with, corresponds to, and/or identifies the analyte. In some embodiments, the method further comprises contacting the sample with a sequencing primer configured to hybridize to the priming site and be bound by a polymerase and a nucleotide for base-by-base sequencing of the identifier sequence or a portion thereof in the probe or product thereof.

In some embodiments, the method comprises contacting the biological sample with nucleotides in sequential cycles (e.g., a nucleotide mix comprising nucleotides comprising different bases for each cycle), wherein a complex is formed in each cycle and the complex comprises: i) the sequencing primer or an extension product thereof hybridized to the probe or product thereof, ii) a polymerase, and iii) a cognate nucleotide that base pairs with a nucleotide in the identifier sequence. In some embodiments, in each cycle, the method comprises detecting a signal (an ON signal) and/or an absence of signal (an OFF signal) associated with the cognate nucleotide and/or the polymerase is detected at the location, wherein the ON signal, the OFF signal, or a combination thereof corresponds to the base in the cognate nucleotide and the corresponding nucleotide in the identifier sequence. In some embodiments, the method comprises generating a signal code sequence comprising signal codes corresponding to the ON signals, the OFF signals, or combinations thereof in the sequential cycles at the location, thereby detecting the identifier sequence at the location in the biological sample. Since the identifier sequence can be present in, be associated with, correspond to, and/or identify the analyte, detection of the identifier sequence at the location can be used to identify the analyte at the location. For instance, in cases where the identifier sequence uniquely identifies the analyte from among a plurality of analytes, detection of the identifier sequence at the location identifies the analyte at the location. In some embodiments, a combination of identifier sequences in the analyte and/or in the probe or product thereof identifies the analyte, and each identifier sequence can be sequenced in order to decode the combination and identify the analyte.

The present disclosure provides methods for detecting a plurality of analytes in situ in a cell sample or a tissue sample. Provided herein are probes (e.g., first and second probes) designed to reduce optical crowding of signals in the biological sample. In some embodiments, a first and second probe is contacted with a first and second analyte (e.g., nucleic acid molecules such as mRNA) in the biological sample (FIG. 1 (101)). In some embodiments, the first and second probes directly or indirectly bind to a first and second analyte at a first and second location, respectively, in the sample. In some aspects, the first and second probes are primary probes that directly bind to their corresponding analytes at locations in the sample. In some aspects, the first and second probes directly or indirectly bind to a first and second primary probe in the sample. In some embodiments, the first and second probe may be circularizable probes or probe sets. In some embodiments, the first and second probes may be linear probes or probe sets. In some embodiments, the first and second probes are amplified in situ to generate first and second products (e.g., first and second rolling circle amplification (RCA products)) of the first and second probes. In some embodiments, the first and second probes, or products thereof, each comprise i) a priming site for a sequencing primer and ii) an identifier sequence associated with the corresponding analyte in the sample. For instance, the first probe or product thereof may comprise i) a first priming site for a first sequencing primer and ii) a first identifier sequence associated with the first analyte, e.g., at a first location in the sample. The priming site for a sequencing primer is a site for initiation of a sequencing reaction, such as a sequencing by synthesis (SBS) or a sequencing by binding (SBB) reaction. In some embodiments, the first and second identifier sequence is associated with the first and second analyte in the sample. Decoding of the first and second identifier sequence can enable identification of the first and second analytes in the sample and their respective location(s). In some embodiments, the identifier sequence is a barcode sequence that is associated with the analyte or corresponds to the identity of the analyte, and decoding the barcode sequence enables identification of the analyte, in addition to revealing the spatial location of the analyte in the biological sample.

In some embodiments, the method comprises performing SBS or SBB of the first and second identifier sequences (FIG. 1 (102)). In some embodiments, the SBS or SBB reactions are performed using the first and second sequencing primers. The first and second sequencing primers bind to the first and second priming sites, respectively, on the first and second probes or products thereof. In some embodiments, the method includes performing a cyclic series of nucleotide incorporation steps, e.g., incorporation of A, T, C, or G in SBS. In some embodiments, the method includes performing a cyclic series of nucleotide binding steps, e.g., binding of A, T, C, or G in SBB.

In some embodiments, the method comprises detecting a signal such as an ON signal or an absence of a signal such as an OFF signal during the sequencing steps (FIG. 1 (103)). In some embodiments, the method comprises detecting the first and second ON signal and/or OFF signal at a first and second location in the sample. In some embodiments, the signals detected in a particular cycle correspond to a signal code for the cycle. In some embodiments, a signal code corresponds to a signal of a first color, a signal of a second color, a signal of a third color, or absence of signal. In some aspects, the first, second, and third colors are different. In some aspects, the first, second, and third colors are the same. In some aspects, the SBS or SBB reactions are repeated in one or more sequential cycles to generate a series of signal codes, each signal code corresponding to a signal (ON signal) or an absence of a signal (OFF signal), or a combination of ON signals and/or OFF signals (FIG. 1 (104)).

In some embodiments, the series of signal codes are detected at different locations (e.g., first and second location) in the sample. In some embodiments, a nucleotide in the first barcode sequence detected in a particular cycle corresponds to a signal code comprising an ON signal, and the corresponding nucleotide in the second barcode sequence detected in the particular cycle corresponds to a signal code comprising an OFF signal. In some embodiments, one or more pairs of corresponding nucleotides in the first and second barcode sequences to be detected in the same cycle are chosen to reduce optical crowding of signals detected in the cycle.

In some aspects, each series of signal codes comprises a signal code sequence. For instance, the series of signal codes detected in sequential cycles at the first location comprises a first signal code sequence. The series of signal codes detected in sequential cycles at the second location comprises a second signal code sequence. In some aspects, the first and second signal code sequences are used to decode the identifier sequences on the first and second probe or products thereof. In some embodiments, the method comprises detecting the first and second identifier sequences based on the first and second signal code sequences (FIG. 1 (105)). In some aspects, the identifier sequence on a probe or product thereof is a barcode sequence. In some aspects, the barcode sequence on the probe or product thereof is assigned to the analyte bound to the probe. In some aspects, detection of the barcode sequences in situ by SBS or SBB enables identification of the analytes in parallel while simultaneously reducing optical crowding of signals during multiple cycles of decoding.

FIG. 2 depicts an exemplary illustration of a sequencing by synthesis reaction of an identifier sequence on a probe or product thereof (e.g., an RCA product). Exemplary hybridization complexes comprising identifier sequences are also shown.

The probe or product can comprise i) a priming site for a sequencing primer and ii) an identifier sequence. In some embodiments, the priming site is a site for hybridization of a sequencing primer for initiation of sequencing. In some embodiments, the identifier sequence is a barcode sequence. In some embodiments, the identifier sequence or the barcode sequence is associated with the corresponding analyte in the sample. Decoding of the identifier sequence or barcode sequence on the probe or product thereof can enable identification of the analyte bound to the probe. In some embodiments, an SBS reaction is performed by contacting the biological sample with a nucleotide mixture in sequential cycles (FIG. 2). In some embodiments, in each cycle a complex is formed, comprising i) a sequencing primer or an extension product thereof hybridized to the priming site, ii) a polymerase, and iii) a cognate nucleotide that base pairs with a nucleotide in the identifier sequence. In some aspects, the sequencing primer binds to the priming site on the probe or product thereof and generates an extension product as the sequencing reaction progresses. In some embodiments, the sequencing reaction includes performing a cyclic series of nucleotide incorporation steps. Cognate nucleotides A, T, C, or G bind to their corresponding nucleotides in the identifier sequences and are incorporated into the sequencing primer or the extension product. In some embodiments, the cognate nucleotides are incorporated by the polymerase into the sequencing primer or the extension product. In some embodiments, the nucleotide mixture contacted to the biological sample comprises a mixture of fluorescently labeled and unlabeled nucleotides. In some aspects, the nucleotide mixture comprises three nucleotides that are fluorescently labeled and one nucleotide is not fluorescently labeled. In some aspects, the nucleotide mixture comprises two nucleotides that are fluorescently labeled and two nucleotides that are not fluorescently labeled. For instance, as shown in FIG. 2, nucleotides T, A, and G are labeled with fluorescent moieties while nucleotide C is unlabeled. In some embodiments, a signal (an ON signal) and/or an absence of signal (an OFF signal) associated with the cognate nucleotide is detected at a particular location in the biological sample. In some embodiments, the ON signal, the OFF signal, or a combination thereof corresponds to the base in the cognate nucleotide and the corresponding nucleotide in the identifier sequence. For instance, an ON signal may be detected as a result of incorporation of labeled nucleotides T, A, or G while an OFF signal may be detected as a result of incorporation of the unlabeled nucleotide C, to the sequencing primer or extension product. In some aspects, the identifier sequences are detected based on the signal code sequences generated by SBS. In some aspects, detection of the identifier sequence as shown in FIG. 2 enables identification of analytes while simultaneously reducing optical crowding of signals.

A. Dark Bases and Nucleotide Mixes

In some embodiments, provided herein is a method comprising determining the sequence of an identifier sequence in situ in a cell or tissue sample, where the identifier sequence comprises bases that do not give rise to a detectable signal in the corresponding base-by-base sequencing cycles, e.g., these bases are "dark." In any particular identifier sequence, the dark bases can be the same (e.g., all G) or different (a first dark base being G and a second dark base being C). In any particular identifier sequence, any two or more dark bases can be consecutive (the nucleotide residues are directly linked by a phosphodiester bond) or non-consecutive (e.g., the nucleotide residues are separated by one or more nucleotide residues, at least one of which comprises a non-dark base).

In some embodiments, a plurality of different identifier sequences are sequenced in situ in the cell or tissue sample, using a base-by-base sequencing method, e.g., SBS or SBB, and each of the plurality of different identifier sequences comprise multiple dark bases such that optical crowding in many (e.g., most) of the base-by-base sequencing cycles is limited in order to facilitate accurate and efficient signal detection and decoding.

In some embodiments, provided herein is a method of analyzing a biological sample, comprising: a) contacting the biological sample with a first probe and a second probe, wherein: the biological sample is a cell or tissue sample, the biological sample comprises a first analyte and a second analyte at a first location and a second location, respectively, in the biological sample, the first probe and the second probe directly or indirectly bind to the first analyte and the second analyte, respectively, the first probe or a product thereof comprises i) a first priming site for a first sequencing primer and ii) a first identifier sequence associated with the first analyte, and the second probe or a product thereof comprises i) a second priming site for a second sequencing primer and ii) a second identifier sequence associated with the second analyte; b) performing base-by-base sequencing of the first and second identifier sequences using the first and second sequencing primers, thereby generating a first signal code sequence and a second signal code sequence, each comprising signal codes each corresponding to a signal (an ON signal), an absence of signal (an OFF signal), or a combination thereof detected in sequential cycles at the first location and the second location, respectively, wherein in one or more of the sequential cycles, an ON signal is detected at the first location and an OFF signal is detected at the second location; and c) detecting the first and second identifier sequences in the biological sample based on the first and a second signal code sequences.

In some embodiments, the first and second identifier sequences are different and are associated with different first and second analytes, respectively. In some embodiments, the first and second identifier sequences are different and are associated with the same analyte. In some embodiments, the first and second identifier sequences can comprise barcode sequences or complements thereof. In some embodiments, a first barcode sequence and a second barcode sequence can be assigned to the first and second analytes, respectively.

In some embodiments, assignment of code words (corresponding to physical barcode or identifier sequences) to each of a plurality of analytes is performed using any suitable scheme that minimizes optical crowding in the fluorescence images used to decode the identifier sequences. Methods for designing codebooks and assigning code words to analytes to minimize optical crowding are described in U.S. 63/317, 842, entitled "in situ Code Design Methods for Minimizing Optical Crowding" and filed Mar. 8, 2022, and International Patent Application No. PCT/US2023/063866, entitled "in situ Code Design Methods for Minimizing Optical Crowding" and filed Mar. 7, 2023, the contents of which are incorporated herein by reference in their entirety. In some aspects, the assignment of identifier sequences (corresponding to code words) to each of a plurality of analytes is optimized for each of the analytes. In some embodiments, for example, assignment of identifier sequences to each of a plurality of analytes is performed based on expression data for the plurality of analytes. For example, the expression data may comprise whole-transcriptome, single cell reference gene expression data, that has been clustered according to cell type. In some embodiments, code words/identifier sequences comprising the largest number of OFF bits can be assigned to analytes (e.g., genes) sequentially, going in descending order of the number of OFF bits in the code word and the analyte's (e.g., gene's) highest expression level over all cell types. In some embodiments, specifying a code word (corresponding to an identifier sequence) for a gene comprises computing a metric (e.g., worst-case density or maximum predicted density) that would be achieved by assigning any of the still-available code words to the current gene. Then, the code word that yields the lowest worst-case density is assigned to the particular analyte. In some cases, the worst-case density is the expression density of the (cell type, code bit) pair that has the highest total expression density of genes that are ON in that code bit.

In some instances, the code words (corresponding to identifier sequences) may be assigned to a plurality of analytes according to a decision rule (e.g., a minimax decision rule) designed to minimize a maximum predicted density of ON signals across the series of images acquired across one or more detection channels (e.g., 1, 2, 3, 4, or more than 4 detection channels) during a plurality of sequencing cycles. For example, in some instances, the code words of the code book may be assigned to a plurality of analytes (e.g., at least 5, at least 10, at least 20, at least 40, at least 60, at least 80, at least 100, at least 200, at least 400, at least 600, at least 800, at least 1,000, at least 2,000, at least 4,000, at least 6,000, at least 8,000, at least 10,000, at least 20,000, at least 40,000, at least 60,000, at least 80,000, at least 100,000, at least 200,000, at least 400,000, at least 600,000, at least 800,000, at least 1,000,000, at least $2\times10^6$, at least $3\times10^6$, at least $4\times10^6$, at least $5\times10^6$, at least $6\times10^6$, at least $7\times10^6$, at least $8\times10^6$, at least $9\times10^6$, at least $10^7$, at least $10^8$, at least $10^9$, or more than $10^9$ analytes) according to a minimax decision rule that minimizes the maximum predicted density of ON signals (corresponding to ON bits of target analyte-associated code words) detected per image (e.g., where a different image of the biological sample is acquired or received for each of one, two, three, four, or more than four detection channels in each sequencing cycle) for the series of images acquired during a plurality of sequencing cycles (e.g., for 2, 3, 4, 5, 6, 7, 8, 9, 10, 11, 12, 13, 14, 15, 16, 17, 18, 19, 20, or more than 20 sequencing cycles) used for sequencing a plurality of analytes.

In some instances, the code words in a code book may be assigned to a plurality of analytes according to a decision rule that ensures that ON bits are distributed more-or-less evenly across the plurality of sequencing cycles and detection channels used for sequencing. For example, in some instances, the code words of the code book may be assigned to a plurality of analytes (e.g., at least 5, at least 10, at least 20, at least 40, at least 60, at least 80, at least 100, at least 200, at least 400, at least 600, at least 800, at least 1,000, at least 2,000, at least 4,000, at least 6,000, at least 8,000, at least 10,000, at least 20,000, at least 40,000, at least 60,000, at least 80,000, at least 100,000, at least 200,000, at least 400,000, at least 600,000, at least 800,000, at least 1,000, 000, at least $2\times10^6$, at least $3\times10^6$, at least $4\times10^6$, at least $5\times10^6$, at least $6\times10^6$, at least $7\times10^6$, at least $8\times10^6$, at least $9\times10^6$, at least $10^7$, at least $10^8$, at least $10^9$, or more than $10^9$ analytes) according to a decision rule that ensures that a total number of ON signals detected in a given image for a given sequencing cycle is within ±5%, ±10%, ±15%, ±20%, or ±25% of a mean number of ON signals detected per image (e.g., where a different image of the biological sample is acquired or received for each of one, two, three, four, or more than four detection channels in each sequencing cycle) for the series of images acquired during a plurality of sequencing cycles (e.g., for 2, 3, 4, 5, 6, 7, 8, 9, 10, 11, 12, 13, 14, 15, 16, 17, 18, 19, 20, or more than 20 sequencing cycles) used for sequencing a plurality of analytes.

In some instances, the code words in a code book may be assigned to a plurality of analytes according to a decision rule that ensures that the number of target analytes that are visible in a given image (e.g., the number of target analytes for which the corresponding code word has an ON bit in a given image) are distributed more-or-less evenly across the plurality of sequencing cycles and detection channels used for sequencing. For example, in some instances, the code words of the code book may be assigned to a plurality of analytes (e.g., at least 5, at least 10, at least 20, at least 40, at least 60, at least 80, at least 100, at least 200, at least 400, at least 600, at least 800, at least 1,000, at least 2,000, at least 4,000, at least 6,000, at least 8,000, at least 10,000, at least 20,000, at least 40,000, at least 60,000, at least 80,000, at least 100,000, at least 200,000, at least 400,000, at least 600,000, at least 800,000, at least 1,000,000, at least $2\times10^6$, at least $3\times10^6$, at least $4\times10^6$, at least $5\times10^6$, at least $6\times10^6$, at least $7\times10^6$, at least $8\times10^6$, at least $9\times10^6$, at least $10^7$, at least $10^8$, at least $10^9$, or more than $10^9$ analytes) to ensure that the number of target analytes that are visible (e.g., that have a corresponding code word that has an ON bit) in a given image for a given sequencing cycle is within ±5%, ±10%, ±15%, ±20%, or ±25% of a mean number of target analytes that are detected per image (e.g., where a different image of the biological sample is acquired or received for each of one, two, three, four, or more than four detection channels in each cycle) for the series of images acquired during a plurality of sequencing cycles (e.g., for 2, 3, 4, 5, 6, 7, 8, 9, 10, 11, 12, 13, 14, 15, 16, 17, 18, 19, 20, or more than 20 cycles) used for sequencing a plurality of analytes.

In some instances, code words may be assigned to analytes using a minimax decision rule (e.g., designed to minimize a maximum predicted density of ON signals across the series of images), a mean ON signal decision rule (e.g., designed to ensure that a total number of ON signals detected in a given image for a given sequencing cycle is within ±5%, ±10%, ±15%, ±20%, or ±25% of a mean number of ON signals detected per image), a mean target number decision rule (e.g., designed to ensure that the number of target analytes that are visible (e.g., that have a corresponding code word that has an ON bit) in a given image for a given sequencing cycle is within ±5%, ±10%, ±15%, ±20%, or ±25% of a mean number of target analytes that are detected per image), or any combination thereof.

In some instances, the decision rule (or decision process) may be implemented in an iterative manner. For example, in some instances, the one or more code words may be rank-ordered according to code word weight (e.g., the total number of ON bits in a given code word), the one or more analytes may be rank-ordered according to a predicted density, and the one or more rank-ordered code words may be assigned to the one or more rank-ordered analytes using an iterative process repeated for each of the one or more analytes in decreasing order of maximum predicted density, the iterative process comprising: computing a predicted density of ON signals for every combination of remaining, unassigned code words and the analyte across the series of images; selecting a code word from the remaining, unassigned code words that minimizes the predicted density of ON signals across the series of images; and assigning the selected code word to the analyte. In some instances, the iterative process may further comprise reviewing previous assignments of code words to analytes, and changing the code word selected for the current analyte to minimize the predicted density of ON signals across the series of images for analytes to which code words have been previously assigned.

In some aspects, optimized assignment of code words to analytes is an approach in which code words are assigned to corresponding analytes according to a decision rule based on prior knowledge of an abundance or distribution of target analytes in a given biological sample, e.g., expression data for the analytes, to reduce the weight of code words corresponding to highly expressed analytes. In some instances, code words may be assigned to corresponding analytes according to a decision rule based on, e.g., single cell expression data for the target analytes in clustered cell types, to reduce the weight of code words corresponding to highly expressed target analytes, where the clustered cell types represent a distribution of cell types found in the biological sample. In some instances, the expression data for the one or more target analytes comprises bulk gene expression data, bulk protein expression data, spatial gene expression data, spatial protein expression data, single cell gene expression data, single cell protein expression data, or any combination thereof.

Assume, for example, that single cell expression data (e.g., single cell gene expression data or single cell protein expression data) is available for the biological sample of interest (e.g., a tissue sample of interest) where the expression data has been clustered according to cell type clusters, each with an average gene or protein expression profile, and where the clustered cell types represent a distribution of cell types found in the biological sample. In some instances, the clustered single cell expression data may provide the best prior information for the expression profiles likely to be observed in the in situ experiment, where the density of labeled features is likely to mimic the expression profiles.

Given a codebook, and an assignment of analytes (e.g., gene transcripts) to code words in the codebook, the single cell type expression data can be used to determine the expected density of labeled spots that will be observed for each cell type in each sequencing cycle and detection channel of the sequencing process.

In some aspects, the code word for each gene transcript is designed to explicitly avoid this situation and reduce the incidence of over-crowded cycles, by distributing the number (or density) of ON features over a plurality of sequencing cycles and detection channels and including the absence of signal (an OFF signal) as described herein. As indicated above, in some instances the code words may be selected/assigned according to a decision rule (e.g., a minimax decision rule) that minimizes the maximum predicted density of ON signals in the images acquired during a cyclic sequencing process. In some instances, code words may be selected/assigned according to a decision rule (e.g., a mean ON signal decision rule) that ensures that a total number of ON signals detected in an image for a given sequencing cycle is within ±5%, ±10%, ±15%, ±20%, or ±25% of a mean number of ON signals detected per image. In some instances, the code words may be selected/assigned according to a decision rule (e.g., a mean target number decision rule) that ensures that the number of target analytes that are visible (e.g., that have a corresponding code word that has an ON bit) in a given image for a given sequencing cycle is within ±5%, ±10%, ±15%, ±20%, or ±25% of a mean number of target analytes that are detected per image. In any of these instances, the decision rule may further comprise assignment based on expression data.

In some instances, for example, the code words may be rank-ordered according to code word weight, the analytes may be rank-ordered according to a maximum expression level across clustered cell types, and the rank-ordered code words may be assigned to the rank-ordered analytes using an iterative process repeated for each of the analytes in decreasing order of maximum expression level, the iterative process comprising: computing a predicted density of ON signals for every combination of remaining, unassigned code words and the analyte across the series of images; selecting a code word from the remaining, unassigned code words that minimizes the predicted density of ON signals across the series of images; and assigning the selected code word to the analyte. In some instances, the iterative process may further comprise reviewing previous assignments of code words to analytes, and changing the code word selected for the current analyte to minimize the predicted density of ON signals across the series of images for analytes to which code words have been previously assigned.

In some instances, for example, the code words may be rank ordered according to code word weight (i.e., the total number of ON bits in a given code word), and the analytes to be detected may be rank ordered according to their corresponding single cell expression data or predicted density in the sample. In some instances, the lowest ranked code word may then be assigned to the highest ranked analyte. In some instances, an algorithm may be developed to assign code words to, e.g., gene transcripts, where the assignment algorithm is optimized to minimize optical crowding and distribute the total number or density of ON bits over the plurality of sequencing cycles and detection channels.

In some embodiments, a nucleotide in the first identifier sequence (e.g., barcode sequence) detected in a particular cycle corresponds to a signal code comprising an ON signal, and the corresponding nucleotide in the second identifier sequence (e.g., barcode sequence) detected in the particular cycle corresponds to a signal code comprising an OFF signal. In some embodiments, one or more pairs of corresponding nucleotides in the first and second barcode sequences to be detected in the same cycle can be chosen to reduce optical crowding of signals detected in the cycle.

In some embodiments, the first and/or second identifier sequences such as barcode sequences (or their corresponding code words) can be designed such that about or at least 30% of the nucleotides therein correspond to OFF signals, e.g., they are dark bases. In some embodiments, about 30%, 40%, 50%, 60%, 70%, 80%, 90%, 95%, or more of the nucleotides in the first and/or second identifier sequences (e.g., barcode sequences) are dark bases.

In some aspects, the signals detected in each cycle of base-by-base sequencing correspond to a block of bits (e.g., a signal code) in a code word corresponding to an identifier sequence (e.g., the first and/or second identifier sequences). The identifier sequences (e.g., barcode sequences) may be assigned based on the code word designs and the base-dye labeling scheme in use (where the latter may be the same for each decoding (imaging) cycle, or may be different for different decoding cycles (e.g., a different dark base (corresponding to an OFF signal) may be used in each cycle). For example, the signals detected in each cycle of base-by-base sequencing may correspond to 3 bits in a code word (corresponding to an identifier sequence), or a portion thereof, where each group of 3 bits can be mapped to a particular nucleotide. Barcode sequences can be derived from the codeword designs, and the base/dye assignment scheme in use can be the same in each cycle, or the assignment of dark base can be adjusted in each cycle. Table 1 provides an example of groups of 3 bits in the code words (corresponding to identifier sequences) that can be mapped to a nucleotide using the exemplary pattern provided:

TABLE 1

| Nucleotide | 3 bit block | Dye/Signal |
| --- | --- | --- |
| A | 001 | Blue dye |
| C | 010 | Green dye |
| G | 100 | Red dye |
| T | 000 | No dye (dark) |

In some instances, the identifiers are made of 3-bit blocks drawn from the four options. The design of a codebook may comprise generating candidate code words (e.g., identifier sequences) with the appropriate number of ON bits (e.g., 4, 5, or 6), then successively identifying new valid code words that are also sufficiently spaced from the existing code words being generated in the codebook. As long as code words have the correct valid blocks of 3 bits, and have the correct number of ON bits (corresponding to a dye/signal), the ON bits can appear anywhere in the identifier. In some aspects, a plurality of "ON" cycles/bits are determined that each code word must have the code words can be designed accordingly. For example, each code word uses 3, 4, 5, 6, 7, or 8 "ON" cycles/bit. In some examples, each code word uses 5 "ON" cycles/bit. In some instances, there may be certain constraints on the code word that make it easier to identify a "real" feature, for example, by requiring that each code word have "ON" bits that light up in at least certain number of colors. For example, each code word may be required to have "ON" bits that light up in at least 2, 3 or 4 colors. In some cases, this allows the signals to be distinguishable from background fluorescent sources which will tend to stay in a single color. In some instances, the barcode sequences are derived from the code word assignment schemes (e.g., optimizing code word assignments), and the base and corresponding dye assignment scheme is used to designate a nucleotide as "dark". In some cases, a nucleotide can be designated as dark for a given cycle or the dark nucleotide can be moved around.

In some instances, the code words are made of 3-bit blocks drawn from four options for dye labeling (e.g., as shown in Table 1), where each bit in the block corresponds to a different detection (color) channel. The design of a codebook may comprise generating candidate code words (e.g., identifier sequences) with the appropriate number of ON bits (e.g., 2, 3, 4, 5 or 6), then successively identifying new valid code words that are also sufficiently spaced (e.g., according to an edit distances, such as a Hamming distance) from the existing code words being generated in the codebook. As long as code words have the correct number of 3 bit blocks (or code word bits), and have the correct number of ON code word bits (corresponding to detection of an ON signal in a given sequencing cycle), the ON bits can appear anywhere within the code word. In some aspects, a plurality of ON code word bits may be specified such that each code word must have the specified number of ON code word bits (corresponding to the number of sequencing cycles in which an ON signal is detected), and the code words can be designed accordingly. For example, in some instances each code word may use 1, 2, 3, 4, 5, 6, 7, or 8 ON bits. In some examples, each code word uses 5 ON bits. In some instances, there may be certain constraints on the code word design that make it easier to identify a "real" image feature, for example, by requiring that each code word comprise ON bits that light up in at least a certain number of colors. For example, each code word may be required to have ON bits that light up in at least 2, 3 or 4 colors. In some cases, this allows the signals to be distinguishable from background fluorescent sources which will tend to stay in a single color.

In some instances, identifier sequences such as barcode sequences are derived from the code word assignment schemes (e.g., by optimizing code word assignments to minimize optical crowding), and the base and corresponding dye labeling scheme may be used to designate a given nucleotide as "dark". In some cases, a nucleotide can be designated as dark for a given sequencing cycle or the designated dark nucleotide may be different for different cycles.

In some embodiments, multiple different identifier sequences (or barcode sequences) can be detected in the biological sample, and each different identifier sequence can be detected at one or more locations in the biological sample. In some embodiments, 30% or more of the different identifier sequences can each comprise at least 25%, 30%, 40%, 50%, 60%, 70%, 80%, 90%, 95%, or more nucleotides that are dark bases. In some embodiments, 40% or more of the different identifier sequences can each comprise at least 25%, 30%, 40%, 50%, 60%, 70%, 80%, 90%, 95%, or more nucleotides that are dark bases. In some embodiments, 50% or more of the different identifier sequences can each comprise at least 25%, 30%, 40%, 50%, 60%, 70%, 80%, 90%, 95%, or more nucleotides that are dark bases. In some embodiments, 60% or more of the different identifier sequences can each comprise at least 25%, 30%, 40%, 50%, 60%, 70%, 80%, 90%, 95%, or more nucleotides that are dark bases. In some embodiments, 70% or more of the different identifier sequences can each comprise at least 25%, 30%, 40%, 50%, 60%, 70%, 80%, 90%, 95%, or more nucleotides that are dark bases. In some embodiments, 80% or more of the different identifier sequences can each comprise at least 25%, 30%, 40%, 50%, 60%, 70%, 80%, 90%, 95%, or more nucleotides that are dark bases. In some embodiments, 90% or more of the different identifier sequences can each comprise at least 25%, 30%, 40%, 50%, 60%, 70%, 80%, 90%, 95%, or more nucleotides that are dark bases. In some embodiments, 95% or more of the different identifier sequences can each comprise at least 25%, 30%, 40%, 50%, 60%, 70%, 80%, 90%, 95%, or more nucleotides that are dark bases.

In some embodiments, the signal codes can each correspond to a signal of a first color, a signal of a second color, a signal of a third color, or absence of signal (e.g., corresponding to a dark base), wherein the first, second, and third colors are different. The dark base can be any one or two of A, T, C, and G. The dark base in an identifier sequence can be "detected" by using a nucleotide mix where the cognate nucleotide comprising a base complementary to the dark base is not detectably labeled. In some embodiments, the biological sample is contacted with a first nucleotide mix in which nucleotides comprising a first base are not detectably labeled, whereas nucleotides comprising bases other than the first base are each labeled with one or more detectably labels, and contacting the biological sample with a subsequent nucleotide mix in which nucleotides comprising a subsequent base are not detectably labeled, whereas nucleotides comprising bases other than the subsequent base are each labeled with one or more detectably labels.

In some embodiments, the same nucleotide mix can be used in multiple sequencing cycles, e.g., the subsequent base can be the same as the first base. Any two or more of the multiple sequencing cycles can be consecutive or non-consecutive. For instance, the two or more cycles can be separated by one or more cycles which may or may not use the same nucleotide mix as in the two or more cycles.

In some cases, for example, G in the identifier sequences (e.g., barcode sequences) can be designated as the dark base, and a nucleotide mix comprising unlabeled C nucleotides can be used in two or more or all of the sequencing cycles, whereas nucleotides comprising A, T, or G in the nucleotide mix are detectably labeled. In some aspects, the nucleotide assigned as the dark base can be alternated in different cycles. In some cases, the assignment of different nucleotides as the dark base can avoid long homopolymer runs of the same base in the identifier sequences. For example, G in the identifier sequence can be designated as the dark base in cycles 1, 5, 9; T in the identifier sequence can be designated as the dark base in cycles 2, 6, 10; C in the identifier sequence can be designated as the dark base in cycles 3, 7, 11; and A in the identifier sequence can be designated as the dark base in cycles 4, 8, 12. In some aspects, two nucleotides assigned as the dark base can be alternated in different cycles. In some embodiments, by assigning different dark bases in different cycles (e.g., the dark base can be G in cycles 1, 5, 9, T in 2, 6, 10, C in 3, 7, 11, A in 4, 8, 12), long homopolymer runs of the same base in the barcode sequence can be avoided.

In some cases, the nucleotide mix comprises unlabeled C nucleotides and A, T, and G nucleotides that are labeled with fluorophores of three different colors, e.g., red for T, blue for A, and green for G, such that A, T, and C in an identifier sequence are associated with red, blue, and green signals (all ON signals), respectively, whereas the dark base G in the identifier sequence is associated with an OFF signal. Two exemplary identifier (e.g., barcode) sequences, GGGAGGGGCGTGGGG (SEQ ID NO: 1) and GCGG-GAGGTGGGAGG (SEQ ID NO: 2), are shown in Table 2B below, and signals detected using the three-color chemistry are indicated (dark is indicated by "-").

TABLE 2B

| Cycle No. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Barcode 1 | G | G | G | A | G | G | G | G | C | G | T | G | G | G | G |
| Barcode 1 Signals | — | — | — | Red | — | — | — | — | Green | — | Blue | — | — | — | — |
| Barcode 2 | G | C | G | G | G | A | G | G | T | G | G | G | A | G | G |
| Barcode 2 Signals | — | Green | — | — | — | Red | — | — | Blue | — | — | — | Red | — | — |

In some cases, the nucleotide mix comprises unlabeled C nucleotides and A, T, and G nucleotides that are labeled with fluorophores of two different colors, e.g., red for T, red and green for A (e.g., each nucleotide comprising A is labeled with a red fluorophore and a green fluorophore), and green for G, such that A, T, and C in an identifier sequence are associated with red, red and green, and green signals (all ON signals), respectively, whereas the dark base G in the identifier sequence is associated with an OFF signal. Table 2A below shows signals detected using the two-color chemistry to sequence the two exemplary barcode sequences.

TABLE 2A

| Cycle No. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Barcode 1 | G | G | G | A | G | G | G | G | C | G | T | G | G | G | G |
| Barcode 1 Signals | — | — | — | Red | — | — | — | — | Green | — | Red + Green | — | — | — | — |
| Barcode 2 | G | C | G | G | G | A | G | G | T | G | G | G | A | G | G |
| Barcode 2 Signals | — | Green | — | — | — | Red | — | — | Red + Green | — | — | — | Red | — | — |

In some cases, the nucleotide mix comprises unlabeled C nucleotides and A, T, and G nucleotides that are labeled with fluorophores of one color. For example, each sequencing cycle can include two chemistry steps and two imaging steps. The first chemistry step exposes the sample to a mixture of nucleotides that have fluorescently labeled A and T nucleotides, where C and G nucleotides in the mixture are not fluorescently labeled, but C nucleotides comprise a functional group or moiety for attaching a fluorescent label thereto. During the first imaging step, the signals or absence thereof at multiple locations in the sample are detected (Image 1). The second chemistry step removes the fluorescent label from A nucleotides that have incorporated and adds a fluorescent label to C nucleotides that have incorporated. In both chemistry steps, the G nucleotide is unlabeled. The signals or absence thereof at multiple locations in the sample are again detected (Image 2). The combination of Image 1 and Image 2 are processed to identify which bases are incorporated at each location. For instance, the signal code in a sequencing cycle (Image 1/Image 2) can be ON/OFF for T, OFF/ON for G, ON/ON for A, and OFF/OFF for C in the identifier sequences (e.g., barcode sequences). In some embodiments, the nucleotide in a first barcode sequence detected in the particular cycle corresponds to ON signal(s) (e.g., ON/OFF for T, OFF/ON for G, ON/ON for A), and the corresponding nucleotide in the second barcode sequence detected in the particular cycle corresponds to OFF signal(s) only (e.g., OFF/OFF for C).

In some embodiments, different nucleotide mixes can be used in multiple sequencing cycles. For instance, a first nucleotide mix can comprise nucleotides comprising a first base which are not detectably labeled, whereas nucleotides comprising bases other than the first base in the first nucleotide mix are each labeled with one or more detectably labels (e.g., one, two, or three different colors), and a subsequent nucleotide mix can comprise nucleotides comprising a subsequent base which are not detectably labeled, whereas nucleotides comprising bases other than the subsequent base in the second nucleotide mix are each labeled with one or more detectably labels (e.g., one, two, or three different colors), and the subsequent base is different from the first base.

In some embodiments, provided herein is a method of analyzing a biological sample, comprising: a) contacting the biological sample with a probe that directly or indirectly binds to an analyte at a location in the biological sample, wherein the probe or a product thereof comprises a priming site and a barcode sequence, and a sequencing primer is hybridized to the priming site; b) contacting the biological sample with a first nucleotide mix comprising nucleotides comprising different bases, wherein: in the first nucleotide mix, nucleotides comprising a first base are not detectably labeled, and nucleotides comprising one or more other bases are detectably labeled, and a complex is formed, the complex comprising i) the sequencing primer hybridized to the probe or product thereof, ii) a polymerase, and iii) a cognate nucleotide that base pairs with a first nucleotide in the barcode sequence, and a signal (an ON signal) and/or an absence of signal (an OFF signal) associated with the cognate nucleotide is detected at the location, wherein the ON signal, the OFF signal, or a combination thereof corresponds to the base in the cognate nucleotide and the first nucleotide in the barcode sequence; c) contacting the biological sample with a subsequent nucleotide mix comprising nucleotides comprising different bases, wherein: in the second nucleotide mix, nucleotides comprising a subsequent base are not detectably labeled, and nucleotides comprising one or more other bases are detectably labeled, the second base is different from the first base, a complex is formed, the complex comprising i) an extension product of the sequencing primer hybridized to the probe or product thereof, ii) a polymerase, and iii) a cognate nucleotide that base pairs with a subsequent nucleotide in the barcode sequence, and a signal (an ON signal) and/or an absence of signal (an OFF signal) associated with the cognate nucleotide is detected at the location, wherein the ON signal, the OFF signal, or a combination thereof corresponds to the base in the cognate nucleotide and the subsequent nucleotide in the barcode sequence; and d) generating a signal code sequence comprising signal codes corresponding to the ON signals, the OFF signals, or combinations thereof in step b) and step c) at the location, thereby detecting the barcode sequence at the location in the biological sample.

In some embodiments, the biological sample can be contacted with two or more of the following nucleotide mixes in sequential cycles in any order: nucleotide mix 1 in which nucleotides comprising G are not detectably labeled, whereas nucleotides comprising A, C, or T are detectably labeled (e.g., using a one-, two-, or three-color chemistry); nucleotide mix 2 in which nucleotides comprising T are not detectably labeled, whereas nucleotides comprising A, C, or G are detectably labeled (e.g., using a one-, two-, or three-color chemistry); nucleotide mix 3 in which nucleotides comprising C are not detectably labeled, whereas nucleotides comprising A, G, or T are detectably labeled (e.g., using a one-, two-, or three-color chemistry); and nucleotide mix 4 in which nucleotides comprising A are not detectably labeled, whereas nucleotides comprising G, C, or T are detectably labeled (e.g., using a one-, two-, or three-color chemistry).

In some embodiments, any of the nucleotide mixes (e.g., nucleotide mix 1 to nucleotide mix 4) can be used in two or more consecutive base-by-base sequencing cycles, preceded by and/or followed by a cycle using a different nucleotide mix. An exemplary order can be nucleotide mix 4-nucleotide mix 2-nucleotide mix 2-nucleotide mix 1-nucleotide mix 1-nucleotide mix 1-nucleotide mix 3.

B. Multiple Sequencing Primers for Different Identifier Sequences

In some embodiments, provided herein is a method comprising determining the sequences of a plurality of different identifier sequences (e.g., barcode sequences) in situ in a cell or tissue sample, where a first subset of the different identifier sequences are sequenced using a first sequencing primer and a second subset of the different identifier sequences are sequenced using a second sequencing primer. In some aspects, the identifier sequences sequenced using the different sequence primers may comprises bases that do not give rise to a detectable signal in the corresponding base-by-base sequencing cycles, e.g., these bases are "dark" as described in Section III.A. In some embodiments, the first and second sequencing primers are different, e.g., they bind to different priming sites, and when the first subset of the different identifier sequences are sequenced using the first sequencing primer, signals associated with the second subset of the different identifier sequences are not detected. Likewise, when the second subset of the different identifier sequences are sequenced using the second sequencing primer, signals associated with the first subset of the different identifier sequences are not detected. As such, optical crowding of signals can be ameliorated by using multiple sequencing primers across different identifier sequences, and separately detecting signals using each sequencing primer.

In some embodiments, provided herein is a method of analyzing a biological sample, comprising: a) contacting the biological sample with a plurality of probes that each directly or indirectly binds to an analyte at a location in the biological sample, wherein a first probe or a product thereof comprises a first priming site and a first barcode sequence, a second probe or a product thereof comprises a second priming site and a second barcode sequence, and the first priming site and the second priming site are different; b) hybridizing a first sequencing primer to the first priming site; c) contacting the biological sample with nucleotides in sequential cycles, wherein in each cycle: a complex is formed at a first location, the complex comprising i) the first sequencing primer or an extension product thereof hybridized to the first probe or product thereof, ii) a polymerase, and iii) a cognate nucleotide that base pairs with a nucleotide in the first barcode sequence, and a signal (an ON signal) and/or an absence of signal (an OFF signal) associated with the cognate nucleotide is detected at the first location, wherein the ON signal, the OFF signal, or a combination thereof corresponds to the base in the cognate nucleotide and the corresponding nucleotide in the first barcode sequence; d) removing or blocking the first sequencing primer or extension product thereof; e) hybridizing a second sequencing primer to the second priming site; f) contacting the biological sample with nucleotides in sequential cycles, wherein in each cycle: a complex is formed at a second location, the complex comprising i) the second sequencing primer or an extension product thereof hybridized to the second probe or product thereof, ii) a polymerase, and iii) a cognate nucleotide that base pairs with a nucleotide in the second barcode sequence, and a signal (an ON signal) and/or an absence of signal (an OFF signal) associated with the cognate nucleotide is detected at the second location, wherein the ON signal, the OFF signal, or a combination thereof corresponds to the base in the cognate nucleotide and the corresponding nucleotide in the second barcode sequence; g) generating a first signal code sequence comprising signal codes corresponding to the signals in the sequential cycles at the first location, and a second signal code sequence comprising signal codes corresponding to the signals in the sequential cycles at the second location, thereby detecting the first barcode sequence at the first location and the second barcode sequence at the second location in the biological sample.

In some embodiments, the first probe and the second probe directly or indirectly bind to the same analyte. In some embodiments, the first probe and the second probe directly or indirectly bind to different analytes. In some embodiments, the first barcode sequence and the second barcode sequence are of the same sequence but the 3' priming sites are different. As such, the same barcode sequence can be sequenced using different sequencing primers. In some embodiments, the first barcode sequence and the second barcode sequence are different, and are sequenced using different sequencing primers. The first and second barcode sequences can be associated with, correspond to, and/or identify the same analyte or different analytes. In some instances, a plurality of different probes comprises the same first priming site (e.g., primer binding sequence) but each of the different probes of the plurality comprises a different barcode sequence. In some instances, a first plurality of different probes comprises the same first priming site (e.g., primer binding sequence) but each of the different probes in the first plurality comprise different barcode sequences, and a second plurality of different probes comprises the same second priming site (e.g., primer binding sequence) but each of the different probes in the second plurality comprise different barcode sequences.

Figure 3:
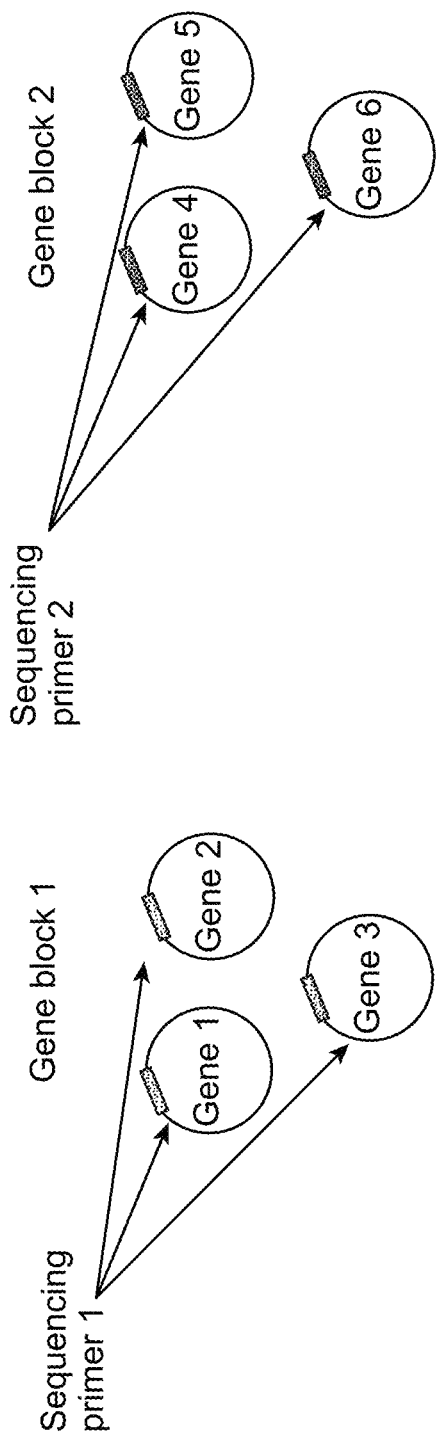
FIG. 3 depicts a method of detecting multiple analytes (e.g., genes) in situ by sequentially decoding blocks (e.g., subsets) of analytes. Probes for a given block of different genes comprise a common priming site.

In some embodiments, the method can comprise hybridizing the first sequencing primer to the first priming site and performing base-by-base sequencing (e.g., SBS or SBB) to generate an extension product of the first sequencing primer. As shown in FIG. 3, the first sequencing primer can be hybridized to first priming sites in molecules or complexes (e.g., probes or products thereof) comprising a first set ("block") of identifier sequences—e.g., barcode sequences for Genes 1 to 3 (Gene Block 1 in the figure)—and used to sequence the first set of identifier sequences, without detecting signals associated with bases in a second set ("block") of identifier sequences—e.g., barcode sequences for Genes 4 to 6 (Gene Block 2 in the figure). In some embodiments, the extension product of the first sequencing primer is prevented from generating signals for base-by-base sequencing, such as SBS and SBB. In some embodiments, the method comprises removing, cleaving, or blocking the extension product of the first sequencing primer. In some embodiments, the method further comprises hybridizing the second sequencing primer to the second priming site and performing base-by-base sequencing (e.g., SBS or SBB) to generate an extension product of the second sequencing primer. As shown in FIG. 3, the second sequencing primer can be hybridized to second priming sites in molecules or complexes (e.g., probes or products thereof) comprising the second set of identifier sequences (e.g., barcode sequences in Gene Block 2) and used to sequence the second set of identifier sequences, without detecting signals associated with bases in the first set of identifier sequences (e.g., barcode sequences in Gene Block 1). In some embodiments, the extension product of the second sequencing primer is prevented from generating signals for base-by-base sequencing, such as SBS and SBB. In some embodiments, the method comprises removing, cleaving, or blocking the extension product of the second sequencing primer.

In some embodiments, the method further comprises hybridizing a third sequencing primer to a third priming site and performing base-by-base sequencing (e.g., SBS or SBB) to generate an extension product of the third sequencing primer. In some embodiments, the third sequencing primer is different in sequence from the first and second sequencing primers. The third sequencing primer can be hybridized to third priming sites in molecules or complexes (e.g., probes or products thereof) comprising a third set of identifier sequences and used to sequence the third set of identifier sequences, without detecting signals associated with bases in the first or second sets of identifier sequences. For instance, the third sequencing primer can be used to sequence barcode sequences for genes that are different from Genes 1 to 6 shown in FIG. 3.

In some embodiments, probes or products thereof for a first plurality of analytes can share a common first priming site, and probes or products thereof for a second plurality of analytes can share a common second priming site. In some embodiments, the second plurality of analytes can comprise two or more different analytes that are different from two or more different analytes of the first plurality of analytes. For instance, as shown in FIG. 3, probes or products thereof for Gene Block 1 (comprising Genes 1 to 3) share a common first priming site ("Sequencing Primer 1" binding site), and probes or products thereof for Gene Block 2 (comprising Genes 4 to 6) share a common second priming site ("Sequencing Primer 2" binding site), and at least one, two, or all genes in Gene Block 1 are different from those in Gene Block 2.

In some embodiments, a first sequencing primer (e.g., "Sequencing Primer 1" in FIG. 3) and a second sequencing primer (e.g., "Sequencing Primer 2" in FIG. 3) can be pre-mixed or separately but simultaneously contacted with the biological sample, followed by multiple cycles of decoding. In some embodiments, one of the sequencing primers can be selectively blocked from generating signals in base-by-base sequencing, while sequencing from the other sequencing primer is performed. Once sequencing from one of the sequencing primers is completed, the blocked sequencing primer can be unblocked and used to sequence the identifier sequence(s).

In some embodiments, a plurality of identifier sequences comprise multiple subsets, and each subset can be sequenced in separate series of sequencing cycles using a different sequencing primer/priming site, thereby reducing optical crowding compared to methods where all of the plurality of identifier sequences are sequenced in the same series of sequencing cycles.

In some instances, the barcode sequences corresponding to two analytes (e.g., genes) can be sequenced using two different sequencing primers and the barcode sequences can be shared between the two genes. In some cases, the barcode sequences can be reused for different analytes.

C. Combinations of Sequencing Primers for the Same Identifier Sequence

Figure 4:
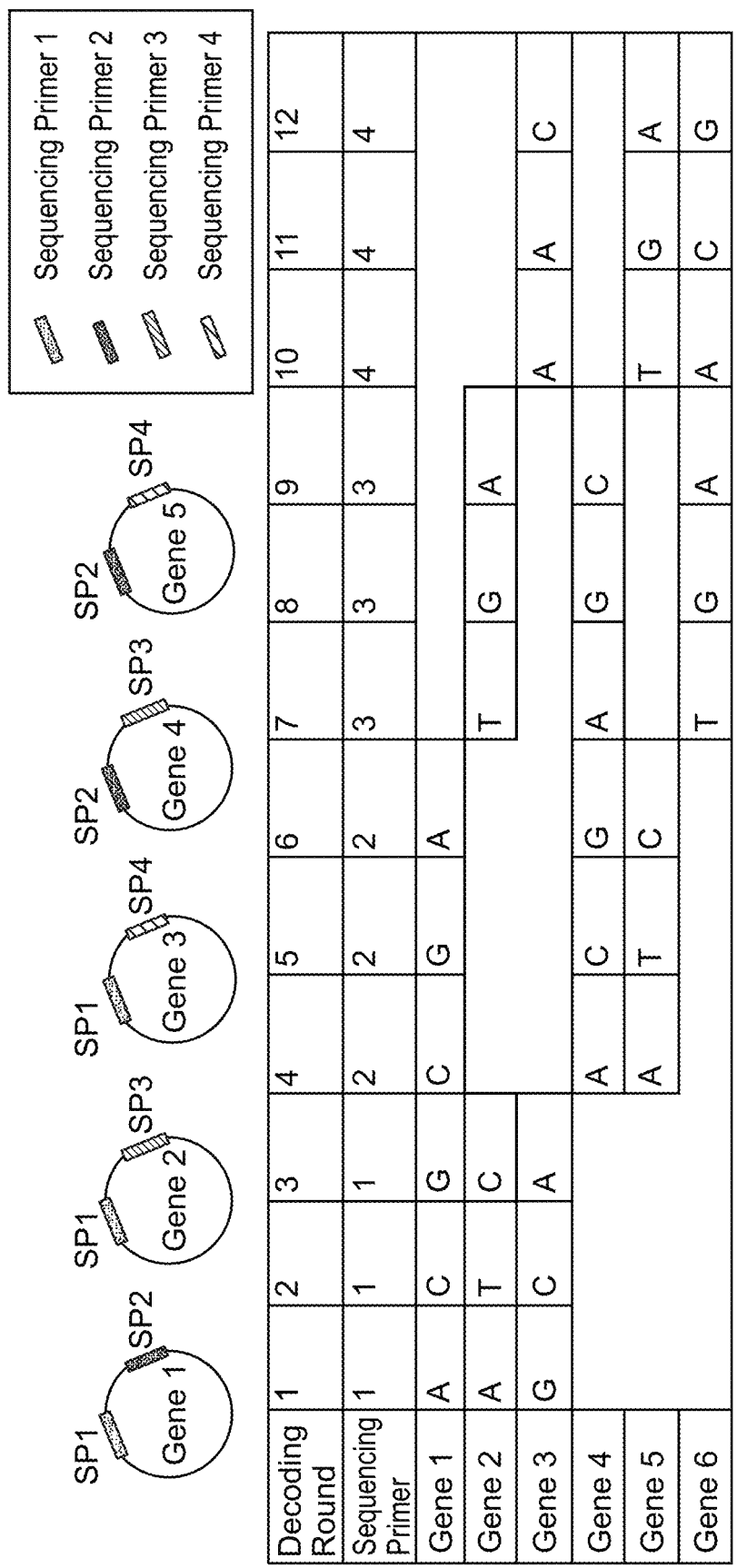
FIG. 4 depicts a method of detecting multiple analytes (e.g., genes) in parallel. Each probe for a particular gene can comprise two or more different priming sites, and probes for any two different genes can share one or more common priming sites.

In some embodiments, the same identifier sequence can be sequenced using two or more different sequencing primers. For instance, a molecule or complex can comprise two different priming sites, e.g., as shown in FIG. 4, each of the molecules or complexes for Genes 1 to 5 can comprise two different priming sites for sequencing the identifier sequence corresponding to the analyte (e.g., a transcript of the corresponding gene). The molecule or complex can be any of those disclosed herein, e.g., an RCA product or probe complex as shown in FIG. 2. In each molecule or complex, both of the two different priming sites can be 3' of the identifier sequence (e.g., barcode sequence), and one of the priming sites can be 3' or 5' of the other priming site. In some embodiments, the different priming sites can partially overlap. In some embodiments, in each molecule or complex, one of the priming sites can be 3' of one copy of the identifier sequence, and another priming site can be 3' of another copy of the identifier sequence. In some aspects, the identifier sequences sequenced using the different priming sites may comprises bases that do not give rise to a detectable signal in the corresponding base-by-base sequencing cycles, e.g., these bases are "dark" as described in Section III.A.

In some embodiments, the biological sample can be contacted with a plurality of probes each configured to directly or indirectly bind to a different analyte, and each probe or product thereof can comprise a combination of different priming sites. In some embodiments, the combination comprises two, three, four, five, or more different priming sites. By way of example, FIG. 4 shows the probe or product thereof for each gene comprises two different priming sites, e.g., "Sequencing Primer 1" binding site and "Sequencing Primer 2" binding site for Gene 1, and "Sequencing Primer 1" binding site and "Sequencing Primer 3" binding site for Gene 2, etc.

In some embodiments, the first probe or product thereof can comprise a first combination of different priming sites comprising the first priming site. For instance, the barcode sequence for Gene 1 can be sequenced using "Sequencing Primer 1" and "Sequencing Primer 2" as shown in FIG. 4. In some embodiments, the second probe or product thereof can comprise a second combination of different priming sites comprising the second priming site. For instance, the barcode sequence for Gene 2 can be sequenced using "Sequencing Primer 1" and "Sequencing Primer 3" as shown in FIG. 4. In some embodiments, the biological sample can be contacted with a third probe that directly or indirectly binds to a third analyte. In some embodiments, the third probe or product thereof can comprise a third combination of different priming sites comprising the first priming site, the second priming site, and/or a third priming site. In some embodiments, any two or more of the first combination, the second combination, and the third combination can share one or more common priming sites. For instance, the barcode sequence for Gene 3 can be sequenced using "Sequencing Primer 1" (shared with Gene 1 and Gene 2) and "Sequencing Primer 4" (not shared with Gene 1 and Gene 2).

In some embodiments, the method can comprise contacting the biological sample with the first sequencing primer for base-by-base sequencing, thereby hybridizing the first sequencing primer to the first priming site in the first probe or product thereof and in one or more other probes or products thereof, and generating extension products of the first sequencing primer. For instance, as shown in FIG. 4, "Sequencing Primer 1" can be hybridized to the priming sites in the probes or products thereof for Genes 1 to 3, and the identifier sequences (e.g., barcode sequences) for Genes 1 to 3 are sequenced. In some embodiments, the method can further comprise removing, cleaving, or blocking the extension products of the first sequencing primer such that they are prevented from generating signals for base-by-base sequencing, e.g., using SBS or SBB. In some embodiments, the method can further comprise contacting the biological sample with the second sequencing primer for base-by-base sequencing, thereby hybridizing the second sequencing primer to the second priming site in the second probe or product thereof and in one or more other probes or products thereof, and generating extension products of the second sequencing primer. For instance, as shown in FIG. 4, "Sequencing Primer 2" can be hybridized to the priming sites in the probes or products thereof for Genes 1, 4, and 5, and the identifier sequences (e.g., barcode sequences) for these genes are sequenced. Likewise, "Sequencing Primer 3" can be hybridized to the priming sites in the probes or products thereof for Genes 2, 4, and 6, and the identifier sequences (e.g., barcode sequences) for these genes are sequenced.

In some embodiments, the method can comprise contacting the biological sample with the first sequencing primer and the second sequencing primer, thereby hybridizing both sequencing primers to the corresponding priming sites in the first probe or product thereof, in the second probe or product thereof, and optionally in one or more other probes or products thereof, and generating extension products of the first sequencing primer and extension products of the second sequencing primer. In some embodiments, the first and second sequencing primers can be pre-mixed or separately but simultaneously contacted with the biological sample, followed by multiple cycles of decoding. In some embodiments, the extension products of the first sequencing primer and of the second sequencing primer can be removed (e.g., stripped), cleaved, or blocked, or otherwise prevented from generating signals for base-by-base sequencing, followed by hybridization of a different mix of sequencing primers (e.g., a third sequencing primer and a fourth sequencing primer).

For instance, as shown in FIG. 4, "Sequencing Primer 1" and "Sequencing Primer 2" can be hybridized to the priming sites in the probes or products thereof, "Sequencing Primer 1" for Genes 1 to 3, and "Sequencing Primer 2" for Genes 1, 4, and 5. For the identifier sequence (e.g., barcode sequence) for Gene 1 where sequencing from both sequencing primers can take place, the signals can be distinguished, e.g., "ACG" from "Sequencing Primer 1" and "CGA" from "Sequencing Primer 2." This can be achieved, for example, where the identifier sequence comprises multiple subsequences separated by a priming site, e.g., 3'-"Sequencing Primer 1" binding site-"ACG"-"Sequencing Primer 2" binding site-"CGA"-5'.

In some embodiments, multiple cycles of nucleotide incorporation or binding can be performed. In some embodiments, the method comprises contacting the biological sample with nucleotides in sequential cycles, detecting signals associated with nucleotide incorporation or binding for each sequential cycle, and generating signal code sequences for the plurality of analytes, e.g., a first plurality of analytes and a second plurality of analytes. In some embodiments, the first plurality of analytes and the second plurality of analytes comprise one or more common analytes. In some embodiments, the first plurality of analytes and the second plurality of analytes do not comprise a common analyte.

In some embodiments, using combinations of sequencing primers for the same identifier sequence allows different parts of the identifier sequence to be sequenced in separate series of sequencing cycles using a different sequencing primer or a different combination of sequencing primers, and helps reducing optical crowding compared to methods where all of the plurality of identifier sequences are sequenced in the same series of sequencing cycles. In some embodiments, the method is not constrained by block diagonal codes. For example, using combinations of sequencing primers may allow increased complexity for the identifier sequences.

In some embodiments, any identifier sequence or a portion thereof disclosed herein can be sequenced multiple times using the same sequencing primer or one or more different sequencing primers, using the same nucleotide mix or one or more different nucleotide mixes, and/or using the same polymerase or one or more different polymerases (e.g., including the same polymerase having different labels or modifications).

In some embodiments, after an identifier sequence or a portion thereof is sequenced, e.g., in Round N, the extension product (or a portion thereof) of the Round 1 sequencing primer can be removed from the template strand to allow hybridization of a sequencing primer for Round (N+1). In some embodiments, the Round (N+1) sequencing primer and the Round N sequencing primer are identical in sequence, such that the identifier sequence or portion thereof can be sequenced again. In some embodiments, in Round (N+1) the identifier sequence or portion thereof is sequenced using the same nucleotide mix as in Round N. In some embodiments, in Round (N+1) and Round N the identifier sequence or portion thereof is sequenced using different nucleotide mixes, e.g., as described in Section III-A. In some embodiments, the Round (N+1) sequencing primer and the Round N sequencing primer are different in sequence, and the nucleotide mixes in Round (N+1) and Round N can be the same or different. In some embodiments, both the Round (N+1) priming site and the Round N priming site are 3' of the identifier sequence, and the Round (N+1) priming site can be 3' or 5' of the Round N priming site. In some embodiments, the Round (N+1) priming site and the Round N priming site can partially overlap.

IV. Detection and Analysis

Generally in sequencing-by-synthesis methods, a first population of detectably labeled nucleotides (e.g., dNTPs) are introduced to contact a template nucleotide hybridized to a sequencing primer, and a first detectably labeled nucleotide (e.g., A, T, C, or G nucleotide) is incorporated by a polymerase to extend the sequencing primer in the 5' to 3' direction using a complementary nucleotide (a first nucleotide residue) in the template nucleotide as template. A signal from the first detectably labeled nucleotide can then be detected. The first population of nucleotides may be continuously introduced, but in order for a second detectably labeled nucleotide to incorporate into the extended sequencing primer, nucleotides in the first population of nucleotides that have not incorporated into a sequencing primer are generally removed (e.g., by washing), and a second population of detectably labeled nucleotides are introduced into the reaction. Then, a second detectably labeled nucleotide (e.g., A, T, C, or G nucleotide) is incorporated by the same or a different polymerase to extend the already extended sequencing primer in the 5' to 3' direction using a complementary nucleotide (a second nucleotide residue) in the template nucleotide as template. Thus, in some embodiments, cycles of introducing and removing detectably labeled nucleotides are performed.

In some instances, cycles of introducing and removing detectably labeled nucleotides in a temporally sequential manner for in situ analysis of an analyte in a biological sample, e.g., a target nucleic acid in a cell in an intact tissue is performed. In some aspects, provided herein is a method for detecting the detectably labeled nucleotides, thereby generating a signal signature associated with the labeled oligonucleotides. In some instances, the signal signature corresponds to an analyte of the plurality of analytes. In some instances, the methods described herein are based, in part, on the development of a multiplexed biological assay and readout, in which a sample is first contacted with a plurality of nucleic acid probes allowing the probes to directly or indirectly bind target analytes, which may then be optically detected (e.g., by sequencing) in a temporally-sequential manner. In some aspects, because the nucleic acid probes are exogenously added and its sequence can be controlled and designed, this allows the use of identifier sequences that are optimized for each analyte (for example compared to directly sequencing an endogenous molecule). In some aspects, provided herein is a method involving a multiplexed biological assay and sequencing readout including optically detecting labeled oligonucleotides in a temporally sequential manner. In some instances, as the positions of the analytes, probes, and/or products thereof can be maintained in a sample through the plurality of cycles of sequencing, the fluorescent spot corresponding to an analyte, probe, or product thereof remains in place during multiple rounds and can be aligned to read out a string of signals associated with each target analyte. The string of observed signals (e.g., ON or OFF signals in each round) at a location can be compared to a code book comprising identifier sequences assigned to a plurality of analytes.

In some embodiments, a method disclosed herein comprises using one or more nucleotides or analogs thereof, including a native nucleotide or a nucleotide analog or modified nucleotide (e.g., labeled with one or more detectable labels). In some embodiments, a nucleotide analog comprises a nitrogenous base, five-carbon sugar, and phosphate group, wherein any component of the nucleotide may be modified and/or replaced. In some embodiments, a method disclosed herein may comprise using one or more non-incorporable nucleotides. Non-incorporable nucleotides may be modified to become incorporable at any point during the sequencing method.

Nucleotide analogs include, but are not limited to, alpha-phosphate modified nucleotides, alpha-beta nucleotide analogs, beta-phosphate modified nucleotides, beta-gamma nucleotide analogs, gamma-phosphate modified nucleotides, caged nucleotides, or ddNTPs. Examples of nucleotide analogs are described in U.S. Pat. No. 8,071,755, which is incorporated by reference herein in its entirety.

In some embodiments, a method disclosed herein may comprise using terminators that reversibly prevent nucleotide incorporation at the 3'-end of the primer. One type of reversible terminator is a 3'-O-blocked reversible terminator. Here the terminator moiety is linked to the oxygen atom of the 3'-OH end of the 5-carbon sugar of a nucleotide. For example, U.S. Pat. Nos. 7,544,794 and 8,034,923 (the disclosures of these patents are incorporated by reference) describe reversible terminator dNTPs having the 3'-OH group replaced by a 3'-ONH$_2$ group. Another type of reversible terminator is a 3'-unblocked reversible terminator, wherein the terminator moiety is linked to the nitrogenous base of a nucleotide. For example, U.S. Pat. No. 8,808,989 (the disclosure of which is incorporated by reference) discloses particular examples of base-modified reversible terminator nucleotides that may be used in connection with the methods described herein. Other reversible terminators that similarly can be used in connection with the methods described herein include those described in U.S. Pat. Nos. 7,956,171, 8,071,755, and 9,399,798, herein incorporated by reference.

In some embodiments, a method disclosed herein may comprise using nucleotide analogs having terminator moieties that irreversibly prevent nucleotide incorporation at the 3'-end of the primer. Irreversible nucleotide analogs include 2', 3'-dideoxynucleotides, ddNTPs (ddGTP, ddATP, ddTTP, ddCTP). Dideoxynucleotides lack the 3'-OH group of dNTPs that is essential for polymerase-mediated synthesis.

In some embodiments, a method disclosed herein may comprise using non-incorporable nucleotides comprising a blocking moiety that inhibits or prevents the nucleotide from forming a covalent linkage to a second nucleotide (3'-OH of a primer) during the incorporation step of a nucleic acid polymerization reaction. The blocking moiety can be removed from the nucleotide, allowing for nucleotide incorporation.

In some embodiments, a method disclosed herein may comprise using 1, 2, 3, 4 or more nucleotide analogs present in the SBS reaction. In some embodiments, a nucleotide analog is replaced, diluted, or sequestered during an incorporation step. In some embodiments, a nucleotide analog is replaced with a native nucleotide. In some embodiments, a nucleotide analog is modified during an incorporation step. The modified nucleotide analog can be similar to or the same as a native nucleotide.

In some embodiments, a method disclosed herein may comprise using a nucleotide analog having a different binding affinity for a polymerase than a native nucleotide. In some embodiments, a nucleotide analog has a different interaction with a next base than a native nucleotide. Nucleotide analogs and/or non-incorporable nucleotides may base-pair with a complementary base of a template nucleic acid.

In some embodiments, one or more nucleotides can be labeled with distinguishing and/or detectable tags or labels. The tags may be distinguishable by means of their differences in fluorescence, Raman spectrum, charge, mass, refractive index, luminescence, length, or any other measurable property. The tag may be attached to one or more different positions on the nucleotide, so long as the fidelity of binding to the polymerase-nucleic acid complex is sufficiently maintained to enable identification of the complementary base on the template nucleic acid correctly. In some embodiments, the tag is attached to the nucleobase of the nucleotide. Alternatively, a tag is attached to the gamma phosphate position of the nucleotide.

Detectable labels can be suitable for small scale detection and/or suitable for high-throughput screening. As such, suitable detectable labels include, but are not limited to, radioisotopes, fluorophores, chemiluminescent compounds, bioluminescent compounds, and dyes. The detectable label can be qualitatively detected (e.g., optically or spectrally), or it can be quantified. Qualitative detection generally includes a detection method in which the existence or presence of the detectable label is confirmed, whereas quantifiable detection generally includes a detection method having a quantifiable (e.g., numerically reportable) value such as an intensity, duration, polarization, and/or other properties. In some embodiments, the detectable label is bound to another moiety, for example, a nucleotide or nucleotide analog, and can include a fluorescent, a colorimetric, or a chemiluminescent label.

In some embodiments, a detectable label can be attached to another moiety, for example, a nucleotide or nucleotide analog. In some embodiments, the detectable label is a fluorophore. For example, the fluorophore can be from a group that includes: 7-AAD (7-Aminoactinomycin D), Acridine Orange (+DNA), Acridine Orange (+RNA), Alexa Fluor® 350, Alexa Fluor® 430, Alexa Fluor® 488, Alexa Fluor® 532, Alexa Fluor® 546, Alexa Fluor® 555, Alexa Fluor® 568, Alexa Fluor® 594, Alexa Fluor® 633, Alexa Fluor® 647, Alexa Fluor® 660, Alexa Fluor® 680, Alexa Fluor® 700, Alexa Fluor® 750, Allophycocyanin (APC), AMCA/AMCA-X, 7-Aminoactinomycin D (7-AAD), 7-Amino-4-methylcoumarin, 6-Aminoquinoline, Aniline Blue, ANS, APC-Cy7, ATTO-TAG™ CBQCA, ATTO-TAG™ FQ, Auramine O-Feulgen, BCECF (high pH), BFP (Blue Fluorescent Protein), BFP/GFP FRET, BOBO™-1/BO-PRO™-1, BOBO™-3/BO-PRO™-3, BODIPY® FL, BODIPY® TMR, BODIPY® TR-X, BODIPY® 530/550, BODIPY® 558/568, BODIPY® 564/570, BODIPY® 581/591, BODIPY® 630/650-X, BODIPY® 650-665-X, BTC, Calcein, Calcein Blue, Calcium Crimson™, Calcium Green-1™ Calcium Orange™, Calcofluor® White, 5-Carboxyfluoroscein (5-FAM), 5-Carboxynaphthofluoroscein, 6-Carboxyrhodamine 6G, 5-Carboxytetramethylrhodamine (5-TAMRA), Carboxy-X-rhodamine (5-ROX), Cascade Blue®, Cascade Yellow™, CCF2 (GeneBLAzer™), CFP (Cyan Fluorescent Protein), CFP/YFP FRET, Chromomycin A3, Cl-NERF (low pH), CPM, 6-CR 6G, CTC Formazan, Cy2®, Cy3®, Cy3.5®, Cy5®, Cy5.5®, Cy7®, Cychrome (PE-Cy5), Dansylamine, Dansyl cadaverine, Dansylchloride, DAPI, Dapoxyl, DCFH, DHR, DiA (4-Di-16-ASP), DiD (DilC18(5)), DIDS, Dil (DilC18(3)), DiO (DiOC18 (3)), DiR (DilC18(7)), Di-4 ANEPPS, Di-8 ANEPPS, DM-NERF (4.5-6.5 pH), DsRed (Red Fluorescent Protein), EBFP, ECFP, EGFP, ELF@-97 alcohol, Eosin, Erythrosin, Ethidium bromide, Ethidium homodimer-1 (EthD-1), Europium (III) Chloride, 5-FAM (5-Carboxyfluorescein), Fast Blue, Fluorescein-dT phosphoramidite, FITC, Fluo-3, Fluo-4, FluorX®, Fluoro-Gold™ (high pH), Fluoro-Gold™ (low pH), Fluoro-Jade, FM® 1-43, Fura-2 (high calcium), Fura-2/BCECF, Fura Red™ (high calcium), Fura Red™/Fluo-3, GeneBLAzer™ (CCF2), GFP Red Shifted (rsGFP), GFP Wild Type, GFP/BFP FRET, GFP/DsRed FRET, Hoechst 33342 & 33258, 7-Hydroxy-4-methylcoumarin (pH 9), 1,5 IAEDANS, Indo-1 (high calcium), Indo-1 (low calcium), Indodicarbocyanine, Indotricarbocyanine, JC-1, 6-JOE, JOJO™-1/JO-PRO™-1, LDS 751 (+DNA), LDS 751 (+RNA), LOLO™-1/LO-PRO™-1, Lucifer Yellow, LysoSensor™ Blue (pH 5), LysoSensor™ Green (pH 5), LysoSensor™ Yellow/Blue (pH 4.2), LysoTracker® Green, LysoTracker® Red, LysoTracker® Yellow, Mag-Fura-2, Mag-Indo-1, Magnesium Green™, Marina Blue@, 4-Methylumbelliferone, Mithramycin, MitoTracker® Green, MitoTracker® Orange, MitoTracker® Red, NBD (amine), Nile Red, Oregon Green® 488, Oregon Green® 500, Oregon Green® 514, Pacific Blue, PBFI, PE (R-phycoerythrin), PE-Cy5, PE-Cy7, PE-Texas Red, PerCP (Peridinin chlorphyll protein), PerCP-Cy5.5 (TruRed), PharRed (APC-Cy7), C-phycocyanin, R-phycocyanin, R-phycoerythrin (PE), PI (Propidium Iodide), PKH26, PKH67, POPO™-1/PO-PRO™-1, POPO™-3/PO-PRO™-3, Propidium Iodide (PI), PyMPO, Pyrene, Pyronin Y, Quantam Red (PE-Cy5), Quinacrine Mustard, R670 (PE-Cy5), Red 613 (PE-Texas Red), Red Fluorescent Protein (DsRed), Resorufin, RH 414, Rhod-2, Rhodamine B, Rhodamine Green™, Rhodamine Red™, Rhodamine Phalloidin, Rhodamine 110, Rhodamine 123, 5-ROX (carboxy-X-rhodamine), S65A, S65C, S65L, S65T, SBFI, SITS, SNAFL®-1 (high pH), SNAFL®-2, SNARF®-1 (high pH), SNARF®-1 (low pH), Sodium Green™, SpectrumAqua®, SpectrumGreen® #1, SpectrumGreen® #2, SpectrumOrange®, SpectrumRed®, SYTO® 11, SYTO® 13, SYTO® 17, SYTO® 45, SYTOX® Blue, SYTOX® Green, SYTOX® Orange, 5-TAMRA (5-Carboxytetramethylrhodamine), Tetramethylrhodamine (TRITC), Texas Red®/Texas Red®-X, Texas Red®-X (NHS Ester), Thiadicarbocyanine, Thiazole Orange, TOTO®-1/TO-PRO®-1, TOTO®-3/TO-PRO®-3, TO-PRO®-5, Tri-color (PE-Cy5), TRITC (Tetramethylrhodamine), TruRed (PerCP-Cy5.5), WW 781, X-Rhodamine (XRITC), Y66F, Y66H, Y66W, YFP (Yellow Fluorescent Protein), YOYO®-1/YO-PRO®-1, YOYO®-3/YO-PRO®-3, 6-FAM (Fluorescein), 6-FAM (NHS Ester), 6-FAM (Azide), HEX, TAMRA (NHS Ester), Yakima Yellow, MAX, TET, TEX615, ATTO 488, ATTO 532, ATTO 542, ATTO 550, ATTO 565, ATTO Rho101, ATTO 590, ATTO 633, ATTO 647N, TYE 563, TYE 665, TYE 705, 5' IRDye® 700, 5' IRDye® 800, 5' IRDye® 800CW (NHS Ester), WellRED D4 Dye, WellRED D3 Dye, WellRED D2 Dye, Lightcycler® 640 (NHS Ester), and Dy 750 (NHS Ester).

The detectable label can be directly detectable by itself (e.g., radioisotope labels or fluorescent labels) or, in the case of an enzymatic label, can be indirectly detectable, e.g., by catalyzing chemical alterations of a substrate compound or composition, which substrate compound or composition is directly detectable. The label can emit a signal or alter a signal delivered to the label so that the presence or absence of the label can be detected. In some cases, coupling may be via a linker, which may be cleavable, such as photocleavable (e.g., cleavable under ultra-violet light), chemically-cleavable (e.g., via a reducing agent, such as dithiothreitol (DTT), tris(2-carboxyethyl)phosphine (TCEP)) or enzymatically cleavable (e.g., via an esterase, lipase, peptidase, or protease).

In addition to the sequencing-by-synthesis approaches described herein, in some instances, nucleic acid sequencing may be performed using alternative sequencing biochemistries. Examples include, but are not limited to, the "sequencing-by-binding" (SBB) approach described in WO 2017/117235, U.S. Pat. Nos. 9,951,385 and 10,655,176, and the "sequencing-by-avidity" (SBA) approach described in U.S. Pat. Nos. 10,768,173 and 10,982,280, all of which are incorporated herein by reference. The sequencing chemistry described in US 2020/0370113, entitled "Polymerase-nucleotide conjugates for sequencing by trapping" and incorporated herein by reference, may also be used.

In some embodiments, an SBB approach herein is based on performing repetitive cycles of detecting a stabilized complex that forms at each position along the template (e.g., a ternary complex that includes the primed template (tethered to a sample support structure), a polymerase, and a cognate nucleotide for the position), under conditions that prevent covalent incorporation of the cognate nucleotide into the primer, and then extending the primer to allow detection of the next position along the template (see, e.g., U.S. Pat. Nos. 9,951,385 and 10,655,176). In the sequencing-by-binding approach, detection of the nucleotide at each position of the template occurs prior to extension of the primer to the next position. Generally, the methodology is used to distinguish the four different nucleotide types that can be present at positions along a nucleic acid template by uniquely labelling each type of ternary complex (i.e., different types of ternary complexes differing in the type of nucleotide it contains) or by separately delivering the reagents needed to form each type of ternary complex. In some instances, the labeling may comprise fluorescence labeling of, e.g., the cognate nucleotide or the polymerase that participates in the ternary complex.

In some instances, for example, the method for sequencing a nucleic acid molecule using a sequencing-by-binding approach may include the steps of (a) forming a mixture under ternary complex stabilizing conditions, where the mixture includes a primed template nucleic acid, a polymerase and nucleotide cognates of first, second and third base types in the template; (b) examining the mixture to determine whether a ternary complex has formed; (c) identifying the next correct nucleotide for the primed template nucleic acid molecule, where the next correct nucleotide is identified as a cognate of the first, second or third base type if a ternary complex is detected in step (b), and where the next correct nucleotide is imputed to be a nucleotide cognate of a fourth base type based on the absence of formation of a ternary complex in step (b); (d) adding a next correct nucleotide to the primer of the primed template nucleic acid after step (b), thereby producing an extended primer; and (e) repeating steps (a) through (d) for the primed template nucleic acid that comprises the extended primer. In some instances, the mixture formed in step (a) may comprise a nucleotide cognate of a first base type in the template. In some instances, the mixture formed in step (a) may comprise nucleotide cognates of a first and second base types in the template.

The "sequencing-by-avidity" (or SBA) approach relies on the increased avidity (or "functional affinity") derived from forming a complex comprising a plurality of individual non-covalent binding interactions (see, e.g., U.S. Pat. Nos. 10,768,173 and 10,982,280). The sequencing-by-avidity approach is based on the detection of a multivalent binding complex formed between a fluorescently-labeled polymer-nucleotide conjugate, a polymerase, and a plurality of primed target nucleic acid molecules tethered to a sample support structure, which allows the detection/base calling step to be separated from the nucleotide incorporation step. Fluorescence imaging is used to detect the bound complex and thereby determine the identity of the N+1 nucleotide in the target nucleic acid sequence (where the primer extension strand is N nucleotides in length).

In some instances, for example, nucleic acid sequencing using a sequencing-by-avidity approach may comprise the steps of: (a) providing a composition comprising: (i) two or more copies of a target nucleic acid sequence; (ii) two or more primer nucleic acid molecules that are complementary to one or more regions of the target nucleic acid sequence; and (iii) two or more polymerase molecules; (b) contacting the composition with a polymer-nucleotide conjugate under conditions sufficient to allow a multivalent binding complex to be formed between the polymer-nucleotide conjugate and the two or more copies of the target nucleic acid sequence in the composition of (a), where the polymer-nucleotide conjugate comprises two or more nucleotide moieties; and (c) detecting the multivalent binding complex (e.g., by fluorescence imaging), thereby determining the identity of a nucleotide in the target nucleic acid sequence. Following the imaging step, the multivalent binding complex is disrupted and washed away, the correct nucleotide (e.g., a blocked nucleotide) is incorporated into the primer extension strand (e.g., following de-blocking of the previously incorporated nucleotide), and the cycle is repeated.

Any suitable enzyme having a polymerase activity can be used in the sequencing reactions described herein, and exemplary polymerases include, but are not limited to, bacterial DNA polymerases, eukaryotic DNA polymerases, archaeal DNA polymerases, viral DNA polymerases and phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases α, β, γ, δ, ε, η, ζ, λ, σ, μ, and κ, as well as the Rev1 polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cp1 DNA polymerase, Cp7 DNA polymerase, T7 DNA polymerase, and T4 polymerase. Other DNA polymerases include thermostable and/or thermophilic DNA polymerases such as DNA polymerases isolated from *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavusu* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus* gorgonarius (Tgo) DNA polymerase, *Thermococcus* acidophilium DNA polymerase; *Sulfolobus acidocaldarius* DNA polymerase; *Thermococcus* sp. go N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; Aeropyrum pernix DNA polymerase; and the heterodimeric DNA polymerase DP1/DP2. Engineered and modified polymerases also are useful in connection with the disclosed techniques. For example, modified versions of the extremely thermophilic marine archaea *Thermococcus* species 9° N (e.g., Therminator DNA polymerase from New England BioLabs Inc.; Ipswich, Mass.) can be used. Still other useful DNA polymerases, including the 3PDX polymerase are disclosed in U.S. Pat. No. 8,703,461, the disclosure of which is incorporated by reference in its entirety. Additional examples include viral RNA polymerases such as T7 RNA polymerase, T3 polymerase, SP6 polymerase, and K11 polymerase; Eukaryotic RNA polymerases such as RNA polymerase I, RNA polymerase II, RNA polymerase III, RNA polymerase IV, and RNA polymerase V, Archaea RNA polymerase, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and Telomerase reverse transcriptase that maintains the telomeres of eukaryotic chromosomes.

Fluorescence detection in tissue samples can often be hindered by the presence of strong background fluorescence. "Autofluorescence" is the general term used to distinguish background fluorescence (that can arise from a variety of sources, including aldehyde fixation, extracellular matrix components, red blood cells, lipofuscin, and the like) from the desired immunofluorescence from the fluorescently labeled antibodies or probes. Tissue autofluorescence can lead to difficulties in distinguishing the signals due to fluorescent antibodies or probes from the general background. In some embodiments, a method disclosed herein utilizes one or more agents to reduce tissue autofluorescence, for example, Autofluorescence Eliminator (Sigma/EMD Millipore), TrueBlack Lipofuscin Autofluorescence Quencher (Biotium), MaxBlock Autofluorescence Reducing Reagent Kit (MaxVision Biosciences), and/or a very intense black dye (e.g., Sudan Black, or comparable dark chromophore).

Examples of fluorescent labels and nucleotides and/or polynucleotides conjugated to such fluorescent labels comprise those described in, for example, Hoagland, Handbook of Fluorescent Probes and Research Chemicals, Ninth Edition (Molecular Probes, Inc., Eugene, 2002); Keller and Manak, DNA Probes, 2nd Edition (Stockton Press, New York, 1993); Eckstein, editor, Oligonucleotides and Analogues: A Practical Approach (IRL Press, Oxford, 1991); and Wetmur, Critical Reviews in Biochemistry and Molecular Biology, 26:227-259 (1991). In some embodiments, exemplary techniques and methods methodologies applicable to the provided embodiments comprise those described in, for example, U.S. Pat. Nos. 4,757,141, 5,151,507 and 5,091,519. In some embodiments, one or more fluorescent dyes are used as labels for labeled target sequences, for example, as described in U.S. Pat. No. 5,188,934 (4,7-dichlorofluorescein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); U.S. Pat. No. 5,066,580 (xanthine dyes); and U.S. Pat.

No. 5,688,648 (energy transfer dyes). Labelling can also be carried out with quantum dots, as described in U.S. Pat. Nos. 6,322,901, 6,576,291, 6,423,551, 6,251,303, 6,319,426, 6,426,513, 6,444,143, 5,990,479, 6,207,392, US 2002/0045045 and US 2003/0017264.

As used herein, the term "fluorescent label" comprises a signaling moiety that conveys information through the fluorescent absorption and/or emission properties of one or more molecules. Exemplary fluorescent properties comprise fluorescence intensity, fluorescence lifetime, emission spectrum characteristics and energy transfer.

In some aspects, the detection (comprising imaging) is carried out using any of a number of different types of microscopy, e.g., confocal microscopy, two-photon microscopy, light-field microscopy, intact tissue expansion microscopy, and/or CLARITY™-optimized light sheet microscopy (COLM).

In some embodiments, fluorescence microscopy is used for detection and imaging of the sample. In some aspects, a fluorescence microscope is an optical microscope that uses fluorescence and phosphorescence instead of, or in addition to, reflection and absorption to study properties of organic or inorganic substances. In fluorescence microscopy, a sample is illuminated with light of a wavelength which excites fluorescence in the sample. The fluoresced light, which is usually at a longer wavelength than the illumination, is then imaged through a microscope objective. Two filters may be used in this technique; an illumination (or excitation) filter which ensures the illumination is near monochromatic and at the correct wavelength, and a second emission (or barrier) filter which ensures none of the excitation light source reaches the detector. Alternatively, these functions may both be accomplished by a single dichroic filter. The "fluorescence microscope" comprises any microscope that uses fluorescence to generate an image, whether it is a more simple set up like an epifluorescence microscope, or a more complicated design such as a confocal microscope, which uses optical sectioning to get better resolution of the fluorescent image.

In some embodiments, confocal microscopy is used for detection and imaging of the sample. Confocal microscopy uses point illumination and a pinhole in an optically conjugate plane in front of the detector to eliminate out-of-focus signal. As only light produced by fluorescence very close to the focal plane can be detected, the image's optical resolution, particularly in the sample depth direction, is much better than that of wide-field microscopes. However, as much of the light from sample fluorescence is blocked at the pinhole, this increased resolution is at the cost of decreased signal intensity—so long exposures are often required. As only one point in the sample is illuminated at a time, 2D or 3D imaging requires scanning over a regular raster (i.e., a rectangular pattern of parallel scanning lines) in the specimen. The achievable thickness of the focal plane is defined mostly by the wavelength of the used light divided by the numerical aperture of the objective lens, but also by the optical properties of the specimen. The thin optical sectioning possible makes these types of microscopes particularly good at 3D imaging and surface profiling of samples. CLARITY™-optimized light sheet microscopy (COLM) provides an alternative microscopy for fast 3D imaging of large clarified samples. COLM interrogates large immunostained tissues, permits increased speed of acquisition and results in a higher quality of generated data.

Other types of microscopy that can be employed comprise bright field microscopy, oblique illumination microscopy, dark field microscopy, phase contrast, differential interference contrast (DIC) microscopy, interference reflection microscopy (also known as reflected interference contrast, or RIC), single plane illumination microscopy (SPIM), super-resolution microscopy, laser microscopy, electron microscopy (EM), Transmission electron microscopy (TEM), Scanning electron microscopy (SEM), reflection electron microscopy (REM), Scanning transmission electron microscopy (STEM) and low-voltage electron microscopy (LVEM), scanning probe microscopy (SPM), atomic force microscopy (ATM), ballistic electron emission microscopy (BEEM), chemical force microscopy (CFM), conductive atomic force microscopy (C-AFM), electrochemical scanning tunneling microscope (ECSTM), electrostatic force microscopy (EFM), fluidic force microscope (FluidFM), force modulation microscopy (FMM), feature-oriented scanning probe microscopy (FOSPM), kelvin probe force microscopy (KPFM), magnetic force microscopy (MFM), magnetic resonance force microscopy (MRFM), near-field scanning optical microscopy (NSOM) (or SNOM, scanning near-field optical microscopy, SNOM, Piezoresponse Force Microscopy (PFM), PSTM, photon scanning tunneling microscopy (PSTM), PTMS, photothermal microspectroscopy/microscopy (PTMS), SCM, scanning capacitance microscopy (SCM), SECM, scanning electrochemical microscopy (SECM), SGM, scanning gate microscopy (SGM), SHPM, scanning Hall probe microscopy (SHPM), SICM, scanning ion-conductance microscopy (SICM), SPSM spin polarized scanning tunneling microscopy (SPSM), SSRM, scanning spreading resistance microscopy (SSRM), SThM, scanning thermal microscopy (SThM), STM, scanning tunneling microscopy (STM), STP, scanning tunneling potentiometry (STP), SVM, scanning voltage microscopy (SVM), and synchrotron x-ray scanning tunneling microscopy (SXSTM), and intact tissue expansion microscopy (exM).

In some embodiments, a method herein comprises subjecting the sample to expansion microscopy methods and techniques. Expansion allows individual targets (e.g., mRNA or RNA transcripts) which are densely packed within a cell, to be resolved spatially in a high-throughput manner. Expansion microscopy techniques are known in the art and can be performed as described in US 2016/0116384 and Chen et al., Science, 347, 543 (2015), each of which are incorporated herein by reference in their entirety. In some embodiments, the method does not comprise subjecting the sample to expansion microscopy. In some embodiments, the method does not comprise dissociating a cell from the sample such as a tissue or the cellular microenvironment. In some embodiments, the method does not comprise lysing the sample or cells therein. In some embodiments, the method does not comprise embedding the sample or molecules from the sample in an exogenous matrix.

V. Samples and Sample Processing

Methods and compositions disclosed herein may be used for analyzing a biological sample, which may be obtained from a subject using any of a variety of techniques including, but not limited to, biopsy, surgery, and laser capture microscopy (LCM), and generally includes cells and/or other biological material from the subject. A biological sample can also be obtained from a eukaryote, such as a tissue sample, a patient derived organoid (PDO) or patient derived xenograft (PDX). A biological sample from an organism may comprise one or more other organisms or components therefrom. For example, a mammalian tissue section may comprise a prion, a viroid, a virus, a bacterium, a fungus, or components from other organisms, in addition to mammalian cells and non-cellular tissue components.

Subjects from which biological samples can be obtained can be healthy or asymptomatic individuals, individuals that have or are suspected of having a disease (e.g., a patient with a disease such as cancer) or a pre-disposition to a disease, and/or individuals in need of therapy or suspected of needing therapy.

In some embodiments, the biological sample corresponds to cells (e.g., derived from a cell culture, a tissue sample, or cells deposited on a surface). In a cell sample with a plurality of cells, individual cells can be naturally unaggregated. For example, the cells can be derived from a suspension of cells (e.g., a body fluid such as blood) and/or disassociated or disaggregated cells from a tissue or tissue section. The number of cells in the biological sample can vary. Some biological samples comprise large numbers of cells, e.g., blood samples, while other biological samples comprise smaller or only a small number of cells or may only be suspected of containing cells, e.g., plasma, serum, urine, saliva, synovial fluids, amniotic fluid, lachrymal fluid, lymphatic fluid, liquor, cerebrospinal fluid and the like.

In some embodiments, a cell-containing biological sample can comprise a body fluid or a cell-containing sample derived from the body fluid, e.g., whole blood, samples derived from blood such as plasma or serum, buffy coat, urine, sputum, lachrymal fluid, lymphatic fluid, sweat, liquor, cerebrospinal fluid, ascites, milk, stool, bronchial lavage, saliva, amniotic fluid, nasal secretions, vaginal secretions, semen/seminal fluid, wound secretions, cell culture and swab samples, or any cell-containing sample derived from the aforementioned samples. In some embodiments, a cell-containing biological sample can be a body fluid, a body secretion or body excretion, e.g., lymphatic fluid, blood, buffy coat, plasma or serum. In some embodiments, a cell-containing biological sample can be a circulating body fluid such as blood or lymphatic fluid, e.g., peripheral blood obtained from a mammal such as human.

The biological sample can include any number of macromolecules, for example, cellular macromolecules and organelles (e.g., mitochondria and nuclei). The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions. In some embodiments, the biological sample may comprise cells which are deposited on a surface. In some embodiments, the biological sample may comprises transcripts of antigen receptor molecules.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells. Biological samples can also include fetal cells and immune cells.

Biological samples can include analytes (e.g., protein, RNA, and/or DNA) embedded in a 3D matrix. In some embodiments, amplicons (e.g., rolling circle amplification products) derived from or associated with analytes (e.g., protein, RNA, and/or DNA) can be embedded in a 3D matrix. In some embodiments, a 3D matrix may comprise a network of natural molecules and/or synthetic molecules that are chemically and/or enzymatically linked, e.g., by crosslinking. In some embodiments, a 3D matrix may comprise a synthetic polymer. In some embodiments, a 3D matrix comprises a hydrogel.

In some embodiments, a substrate herein can be any support that is insoluble in aqueous liquid and which allows for positioning of biological samples, analytes, features, and/or reagents (e.g., probes) on the support. In some embodiments, a biological sample can be attached to a substrate. Attachment of the biological sample can be irreversible or reversible, depending upon the nature of the sample and subsequent steps in the analytical method. In certain embodiments, the sample can be attached to the substrate reversibly by applying a suitable polymer coating to the substrate, and contacting the sample to the polymer coating. The sample can then be detached from the substrate, e.g., using an organic solvent that at least partially dissolves the polymer coating. Hydrogels are examples of polymers that are suitable for this purpose.

In some embodiments, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

A variety of steps can be performed to prepare or process a biological sample for and/or during an assay. Except where indicated otherwise, the preparative or processing steps described below can generally be combined in any manner and in any order to appropriately prepare or process a particular sample for and/or analysis.

(i) Tissue Sectioning

A biological sample can be harvested from a subject (e.g., via surgical biopsy, whole subject sectioning) or grown in vitro on a growth substrate or culture dish as a population of cells, and prepared for analysis as a tissue slice or tissue section. Grown samples may be sufficiently thin for analysis without further processing steps. Alternatively, grown samples, and samples obtained via biopsy or sectioning, can be prepared as thin tissue sections using a mechanical cutting apparatus such as a vibrating blade microtome. As another alternative, in some embodiments, a thin tissue section can be prepared by applying a touch imprint of a biological sample to a suitable substrate material.

The thickness of the tissue section can be a fraction of (e.g., less than 0.9, 0.8, 0.7, 0.6, 0.5, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 µm thick.

More generally, the thickness of a tissue section typically depends on the method used to prepare the section and the physical characteristics of the tissue, and therefore sections having a wide variety of different thicknesses can be prepared and used. For example, the thickness of the tissue section can be at least 0.1, 0.2, 0.3, 0.4, 0.5, 0.7, 1.0, 1.5, 2, 3, 4, 5, 6, 7, 8, 9, 10, 12, 13, 14, 15, 20, 30, 40, or 50 µm. Thicker sections can also be used if desired or convenient, e.g., at least 70, 80, 90, or 100 µm or more. Typically, the thickness of a tissue section is between 1-100 µm, 1-50 µm, 1-30 µm, 1-25 µm, 1-20 µm, 1-15 µm, 1-10 µm, 2-8 µm, 3-7 µm, or 4-6 µm, but as mentioned above, sections with thicknesses larger or smaller than these ranges can also be analysed.

Multiple sections can also be obtained from a single biological sample. For example, multiple tissue sections can be obtained from a surgical biopsy sample by performing serial sectioning of the biopsy sample using a sectioning blade. Spatial information among the serial sections can be preserved in this manner, and the sections can be analysed successively to obtain three-dimensional information about the biological sample.

(ii) Freezing

In some embodiments, the biological sample (e.g., a tissue section as described above) can be prepared by deep freezing at a temperature suitable to maintain or preserve the integrity (e.g., the physical characteristics) of the tissue structure. The frozen tissue sample can be sectioned, e.g., thinly sliced, onto a substrate surface using any number of suitable methods. For example, a tissue sample can be prepared using a chilled microtome (e.g., a cryostat) set at a temperature suitable to maintain both the structural integrity of the tissue sample and the chemical properties of the nucleic acids in the sample. Such a temperature can be, e.g., less than −15° C., less than −20° C., or less than −25° C.

(iii) Fixation and Postfixation

In some embodiments, the biological sample can be prepared using formalin-fixation and paraffin-embedding (FFPE), which are established methods. In some embodiments, cell suspensions and other non-tissue samples can be prepared using formalin-fixation and paraffin-embedding. Following fixation of the sample and embedding in a paraffin or resin block, the sample can be sectioned as described above. Prior to analysis, the paraffin-embedding material can be removed from the tissue section (e.g., deparaffinization) by incubating the tissue section in an appropriate solvent (e.g., xylene) followed by a rinse (e.g., 99.5% ethanol for 2 minutes, 96% ethanol for 2 minutes, and 70% ethanol for 2 minutes).

As an alternative to formalin fixation described above, a biological sample can be fixed in any of a variety of other fixatives to preserve the biological structure of the sample prior to analysis. For example, a sample can be fixed via immersion in ethanol, methanol, acetone, paraformaldehyde (PFA)-Triton X100™, and combinations thereof.

In some embodiments, acetone fixation is used with fresh frozen samples, which can include, but are not limited to, cortex tissue, mouse olfactory bulb, human brain tumor, human post-mortem brain, and breast cancer samples. When acetone fixation is performed, pre-permeabilization steps (described below) may not be performed. Alternatively, acetone fixation can be performed in conjunction with permeabilization steps.

In some embodiments, the methods provided herein comprises one or more post-fixing (also referred to as postfixation) steps. In some embodiments, one or more post-fixing step is performed after contacting a sample with a polynucleotide disclosed herein, e.g., one or more probes such as a circular or padlock probe. In some embodiments, one or more post-fixing step is performed after a hybridization complex comprising a probe and a target is formed in a sample. In some embodiments, one or more post-fixing step is performed prior to a ligation reaction disclosed herein, such as the ligation to circularize a padlock probe.

In some embodiments, one or more post-fixing step is performed after contacting a sample with a binding or labelling agent (e.g., an antibody or antigen binding fragment thereof) for a non-nucleic acid analyte such as a protein analyte. The labelling agent can comprise a nucleic acid molecule (e.g., reporter oligonucleotide) comprising a sequence corresponding to the labelling agent and therefore corresponds to (e.g., uniquely identifies) the analyte. In some embodiments, the labelling agent can comprise a reporter oligonucleotide comprising one or more barcode sequences.

A post-fixing step may be performed using any suitable fixation reagent disclosed herein, for example, 3% (w/v) paraformaldehyde in DEPC-PBS.

(iv) Embedding

As an alternative to paraffin embedding described above, a biological sample can be embedded in any of a variety of other embedding materials to provide structural substrate to the sample prior to sectioning and other handling steps. In some cases, the embedding material can be removed e.g., prior to analysis of tissue sections obtained from the sample. Suitable embedding materials include, but are not limited to, waxes, resins (e.g., methacrylate resins), epoxies, and agar.

In some embodiments, the biological sample can be embedded in a matrix (e.g., a hydrogel matrix). Embedding the sample in this manner typically involves contacting the biological sample with a hydrogel such that the biological sample becomes surrounded by the hydrogel. For example, the sample can be embedded by contacting the sample with a suitable polymer material, and activating the polymer material to form a hydrogel. In some embodiments, the hydrogel is formed such that the hydrogel is internalized within the biological sample.

In some embodiments, the biological sample is immobilized in the hydrogel via cross-linking of the polymer material that forms the hydrogel. Cross-linking can be performed chemically and/or photochemically, or alternatively by any other hydrogel-formation method.

The composition and application of the hydrogel-matrix to a biological sample typically depends on the nature and preparation of the biological sample (e.g., sectioned, non-sectioned, type of fixation). As one example, where the biological sample is a tissue section, the hydrogel-matrix can include a monomer solution and an ammonium persulfate (APS) initiator/tetramethylethylenediamine (TEMED) accelerator solution. As another example, where the biological sample consists of cells (e.g., cultured cells or cells disassociated from a tissue sample), the cells can be incubated with the monomer solution and APS/TEMED solutions. For cells, hydrogel-matrix gels are formed in compartments, including but not limited to devices used to culture, maintain, or transport the cells. For example, hydrogel-matrices can be formed with monomer solution plus APS/TEMED added to the compartment to a depth ranging from about 0.1 m to about 2 mm.

Additional methods and aspects of hydrogel embedding of biological samples are described for example in Chen et al., Science 347(6221):543-548, 2015, the entire contents of which are incorporated herein by reference.

(v) Staining and Immunohistochemistry (IHC)

To facilitate visualization, biological samples can be stained using a wide variety of stains and staining techniques. In some embodiments, for example, a sample can be stained using any number of stains and/or immunohistochemical reagents. One or more staining steps may be performed to prepare or process a biological sample for an assay described herein or may be performed during and/or after an assay. In some embodiments, the sample can be contacted with one or more nucleic acid stains, membrane stains (e.g., cellular or nuclear membrane), cytological stains, or combinations thereof. In some examples, the stain may be specific to proteins, phospholipids, DNA (e.g., dsDNA, ssDNA), RNA, an organelle or compartment of the cell. The sample may be contacted with one or more labeled antibodies (e.g., a primary antibody specific for the analyte of interest and a labeled secondary antibody specific for the primary antibody). In some embodiments, cells in the sample can be segmented using one or more images taken of the stained sample.

In some embodiments, the stain is performed using a lipophilic dye. In some examples, the staining is performed with a lipophilic carbocyanine or aminostyryl dye, or analogs thereof (e.g, DiI, DiO, DiR, DiD). Other cell membrane stains may include FM and RH dyes or immunohistochemical reagents specific for cell membrane proteins. In some examples, the stain may include but is not limited to, acridine orange, acid fuchsin, Bismarck brown, carmine, coomassie blue, cresyl violet, DAPI, eosin, ethidium bromide, acid fuchsine, haematoxylin, Hoechst stains, iodine, methyl green, methylene blue, neutral red, Nile blue, Nile red, osmium tetroxide, ruthenium red, propidium iodide, rhodamine (e.g., rhodamine B), or safranine, or derivatives thereof. In some embodiments, the sample may be stained with haematoxylin and eosin (H&E).

The sample can be stained using hematoxylin and eosin (H&E) staining techniques, using Papanicolaou staining techniques, Masson's trichrome staining techniques, silver staining techniques, Sudan staining techniques, and/or using Periodic Acid Schiff (PAS) staining techniques. PAS staining is typically performed after formalin or acetone fixation. In some embodiments, the sample can be stained using Romanowsky stain, including Wright's stain, Jenner's stain, Can-Grunwald stain, Leishman stain, and Giemsa stain.

In some embodiments, biological samples can be destained. Methods of destaining or discoloring a biological sample generally depend on the nature of the stain(s) applied to the sample. For example, in some embodiments, one or more immunofluorescent stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., *J. Histochem. Cytochem.* 2017; 65(8): 431-444, Lin et al., *Nat Commun.* 2015; 6:8390, Pirici et al., *J. Histochem. Cytochem.* 2009; 57:567-75, and Glass et al., *J. Histochem. Cytochem.* 2009; 57:899-905, the entire contents of each of which are incorporated herein by reference.

(vi) Isometric Expansion

In some embodiments, a biological sample embedded in a matrix (e.g., a hydrogel) can be isometrically expanded. Isometric expansion methods that can be used include hydration, a preparative step in expansion microscopy, as described in Chen et al., *Science* 347(6221):543-548, 2015.

Isometric expansion can be performed by anchoring one or more components of a biological sample to a gel, followed by gel formation, proteolysis, and swelling. In some embodiments, analytes in the sample, products of the analytes, and/or probes associated with analytes in the sample can be anchored to the matrix (e.g., hydrogel). Isometric expansion of the biological sample can occur prior to immobilization of the biological sample on a substrate, or after the biological sample is immobilized to a substrate. In some embodiments, the isometrically expanded biological sample can be removed from the substrate prior to contacting the substrate with probes disclosed herein.

In general, the steps used to perform isometric expansion of the biological sample can depend on the characteristics of the sample (e.g., thickness of tissue section, fixation, cross-linking), and/or the analyte of interest (e.g., different conditions to anchor RNA, DNA, and protein to a gel).

In some embodiments, proteins in the biological sample are anchored to a swellable gel such as a polyelectrolyte gel. An antibody can be directed to the protein before, after, or in conjunction with being anchored to the swellable gel. DNA and/or RNA in a biological sample can also be anchored to the swellable gel via a suitable linker. Examples of such linkers include, but are not limited to, 6-((Acryloyl) amino) hexanoic acid (Acryloyl-X SE) (available from ThermoFisher, Waltham, MA), Label-IT Amine (available from MirusBio, Madison, WI) and Label X (described for example in Chen et al., Nat. Methods 13:679-684, 2016, the entire contents of which are incorporated herein by reference).

Isometric expansion of the sample can increase the spatial resolution of the subsequent analysis of the sample. The increased resolution in spatial profiling can be determined by comparison of an isometrically expanded sample with a sample that has not been isometrically expanded.

In some embodiments, a biological sample is isometrically expanded to a size at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded size. In some embodiments, the sample is isometrically expanded to at least 2× and less than 20× of its non-expanded size.

(vii) Crosslinking and De-Crosslinking

In some embodiments, the biological sample is reversibly cross-linked prior to or during an in situ assay. In some aspects, the analytes, polynucleotides and/or amplification product (e.g., amplicon) of an analyte or a probe bound thereto can be anchored to a polymer matrix. For example, the polymer matrix can be a hydrogel. In some embodiments, one or more of the polynucleotide probe(s) and/or amplification product (e.g., amplicon) thereof can be modified to contain functional groups that can be used as an anchoring site to attach the polynucleotide probes and/or amplification product to a polymer matrix. In some embodiments, a modified probe comprising oligo dT may be used to bind to mRNA molecules of interest, followed by reversible crosslinking of the mRNA molecules.

A hydrogel may include a macromolecular polymer gel including a network. Within the network, some polymer chains can optionally be cross-linked, although cross-linking does not always occur.

In some embodiments, a hydrogel can include hydrogel subunits, such as, but not limited to, acrylamide, bis-acrylamide, polyacrylamide and derivatives thereof, poly(ethylene glycol) and derivatives thereof (e.g., PEG-acrylate (PEG-DA), PEG-RGD), gelatin-methacryloyl (GelMA), methacrylated hyaluronic acid (MeHA), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose, and the like, and combinations thereof.

In some embodiments, a hydrogel includes a hybrid material, e.g., the hydrogel material includes elements of both synthetic and natural polymers. Examples of suitable hydrogels are described, for example, in U.S. Pat. Nos. 6,391,937, 9,512,422, and 9,889,422, and in U.S. Patent Application Publication Nos. 2017/0253918, 2018/0052081 and 2010/0055733, the entire contents of each of which are incorporated herein by reference.

In some embodiments, the hydrogel can form the substrate. In some embodiments, the substrate includes a hydrogel and one or more second materials. In some embodiments, the hydrogel is placed on top of one or more second materials. For example, the hydrogel can be pre-formed and then placed on top of, underneath, or in any other configuration with one or more second materials. In some embodiments, hydrogel formation occurs after contacting one or more second materials during formation of the substrate. Hydrogel formation can also occur within a structure (e.g., wells, ridges, projections, and/or markings) located on a substrate.

In some embodiments, hydrogel formation on a substrate occurs before, contemporaneously with, or after probes are provided to the sample. For example, hydrogel formation can be performed on the substrate already containing the probes.

In some embodiments, hydrogel formation occurs within a biological sample. In some embodiments, a biological sample (e.g., tissue section) is embedded in a hydrogel. In some embodiments, hydrogel subunits are infused into the biological sample, and polymerization of the hydrogel is initiated by an external or internal stimulus.

In embodiments in which a hydrogel is formed within a biological sample, functionalization chemistry can be used. In some embodiments, functionalization chemistry includes hydrogel-tissue chemistry (HTC). Any hydrogel-tissue backbone (e.g., synthetic or native) suitable for HTC can be used for anchoring biological macromolecules and modulating functionalization. Non-limiting examples of methods using HTC backbone variants include CLARITY, PACT, ExM, SWITCH and ePACT. In some embodiments, hydrogel formation within a biological sample is permanent. For example, biological macromolecules can permanently adhere to the hydrogel allowing multiple rounds of interrogation. In some embodiments, hydrogel formation within a biological sample is reversible.

In some embodiments, additional reagents are added to the hydrogel subunits before, contemporaneously with, and/or after polymerization. For example, additional reagents can include but are not limited to oligonucleotides (e.g., probes), endonucleases to fragment DNA, fragmentation buffer for DNA, DNA polymerase enzymes, dNTPs used to amplify the nucleic acid and to attach the barcode to the amplified fragments. Other enzymes can be used, including without limitation, RNA polymerase, ligase, proteinase K, and DNAse. Additional reagents can also include reverse transcriptase enzymes, including enzymes with terminal transferase activity, primers, and switch oligonucleotides. In some embodiments, optical labels are added to the hydrogel subunits before, contemporaneously with, and/or after polymerization.

In some embodiments, HTC reagents are added to the hydrogel before, contemporaneously with, and/or after polymerization. In some embodiments, a cell labelling agent is added to the hydrogel before, contemporaneously with, and/or after polymerization. In some embodiments, a cell-penetrating agent is added to the hydrogel before, contemporaneously with, and/or after polymerization.

Hydrogels embedded within biological samples can be cleared using any suitable method. For example, electrophoretic tissue clearing methods can be used to remove biological macromolecules from the hydrogel-embedded sample. In some embodiments, a hydrogel-embedded sample is stored before or after clearing of hydrogel, in a medium (e.g., a mounting medium, methylcellulose, or other semi-solid mediums).

In some embodiments, a method disclosed herein comprises de-crosslinking the reversibly cross-linked biological sample. The de-crosslinking does not need to be complete. In some embodiments, only a portion of crosslinked molecules in the reversibly cross-linked biological sample are de-crosslinked and allowed to migrate.

(viii) Tissue Permeabilization and Treatment

In some embodiments, a biological sample can be permeabilized to facilitate transfer of species (such as probes) into the sample. If a sample is not permeabilized sufficiently, the amount of species (such as probes) in the sample may be too low to enable adequate analysis. Conversely, if the tissue sample is too permeable, the relative spatial relationship of the analytes within the tissue sample can be lost. Hence, a balance between permeabilizing the tissue sample enough to obtain good signal intensity while still maintaining the spatial resolution of the analyte distribution in the sample is desirable.

In general, a biological sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, Triton X-100™ or Tween-20™), and enzymes (e.g., trypsin, proteases). In some embodiments, the biological sample can be incubated with a cellular permeabilizing agent to facilitate permeabilization of the sample. Additional methods for sample permeabilization are described, for example, in Jamur et al., Method Mol. Biol. 588:63-66, 2010, the entire contents of which are incorporated herein by reference. Any suitable method for sample permeabilization can generally be used in connection with the samples described herein.

In some embodiments, the biological sample can be permeabilized by adding one or more lysis reagents to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes.

Other lysis agents can additionally or alternatively be added to the biological sample to facilitate permeabilization. For example, surfactant-based lysis solutions can be used to lyse sample cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

In some embodiments, the biological sample can be permeabilized by non-chemical permeabilization methods. Non-chemical permeabilization methods that can be used include, but are not limited to, physical lysis techniques such as electroporation, mechanical permeabilization methods (e.g., bead beating using a homogenizer and grinding balls to mechanically disrupt sample tissue structures), acoustic permeabilization (e.g., sonication), and thermal lysis techniques such as heating to induce thermal permeabilization of the sample.

Additional reagents can be added to a biological sample to perform various functions prior to analysis of the sample. In some embodiments, DNase and RNase inactivating agents or inhibitors such as proteinase K, and/or chelating agents such as EDTA, can be added to the sample. For example, a method disclosed herein may comprise a step for increasing accessibility of a nucleic acid for binding, e.g., a denaturation step to open up DNA in a cell for hybridization by a probe. For example, proteinase K treatment may be used to free up DNA with proteins bound thereto.

(ix) Selective Enrichment of RNA or cDNA Species

In some embodiments, where RNA or cDNA is the analyte, one or more RNA or cDNA analyte species of interest can be selectively enriched. For example, one or more species of RNA or cDNA of interest can be selected by addition of one or more oligonucleotides to the sample. In some embodiments, the additional oligonucleotide is a sequence used for priming a reaction by an enzyme (e.g., a polymerase). For example, one or more primer sequences with sequence complementarity to one or more RNAs or cDNAs of interest can be used to amplify the one or more RNAs or cDNAs of interest, thereby selectively enriching these RNAs or cDNAs.

In some aspects, when two or more analytes are analyzed, a first and second probe that is specific for (e.g., specifically hybridizes to) each RNA or cDNA analyte are used. For example, in some embodiments of the methods provided herein, templated ligation is used to detect gene expression in a biological sample. An analyte of interest (such as a protein), bound by a labelling agent or binding agent (e.g., an antibody or epitope binding fragment thereof), wherein the binding agent is conjugated or otherwise associated with a reporter oligonucleotide comprising a reporter sequence that identifies the binding agent, can be targeted for analysis. Probes may be hybridized to the reporter oligonucleotide and ligated in a templated ligation reaction to generate a product for analysis. In some embodiments, gaps between the probe oligonucleotides may first be filled prior to ligation, using, for example, Mu polymerase, DNA polymerase, RNA polymerase, reverse transcriptase, VENT polymerase, Taq polymerase, and/or any combinations, derivatives, and variants (e.g., engineered mutants) thereof. In some embodiments, the assay can further include amplification of templated ligation products (e.g., by multiplex PCR).

In some embodiments, the analytes may be further enriched for in situ readout by immobilization at a location in the biological sample. In a non-limiting example, the analytes may comprise one or more fragments that are specific to a location in the biological sample.

Alternatively, one or more species of RNA can be down-selected (e.g., removed) using any of a variety of methods. For example, probes can be administered to a sample that selectively hybridize to ribosomal RNA (rRNA), thereby reducing the pool and concentration of rRNA in the sample. Additionally and alternatively, duplex-specific nuclease (DSN) treatment can remove rRNA (see, e.g., Archer, et al, Selective and flexible depletion of problematic sequences from RNA-seq libraries at the cDNA stage, *BMC Genomics*, 15 401, (2014), the entire contents of which are incorporated herein by reference). Furthermore, hydroxyapatite chromatography can remove abundant species (e.g., rRNA) (see, e.g., Vandernoot, V. A., cDNA normalization by hydroxyapatite chromatography to enrich transcriptome diversity in RNA-seq applications, *Biotechniques*, 53(6) 373-80, (2012), the entire contents of which are incorporated herein by reference).

A biological sample may comprise one or a plurality of analytes of interest. Methods for performing multiplexed assays to analyze two or more different analytes in a single biological sample are provided.

VI. Compositions, Kits, and Systems

Provided herein are kits, for example comprising one or more oligonucleotides, e.g., any described in Sections I-V, and instructions for performing the methods provided herein. In some embodiments, the kits further comprise one or more reagents for performing the methods provided herein (e.g., nucleotide mixes, probes, etc.). In some embodiments, the kits further comprise one or more reagents required for one or more steps comprising hybridization, ligation, extension, amplification, detection, and/or sample preparation as described herein. In some embodiments, the kit further comprises an enzyme such as a ligase and/or a polymerase described herein. In some embodiments, the kit comprises a polymerase, for instance for performing extension of the primers and to incorporate nucleotides. In some embodiments, the kits may contain reagents for forming a functionalized matrix (e.g., a hydrogel), such as any suitable functional moieties. In some examples, also provided are buffers and reagents for tethering the probes and products (e.g., RCA products) to the functionalized matrix. The various components of the kit may be present in separate containers or certain compatible components may be pre-combined into a single container. In some embodiments, the kits further contain instructions for using the components of the kit to practice the provided methods.

In some embodiments, the kits can contain reagents and/or consumables required for performing one or more steps of the provided methods. In some embodiments, the kits contain reagents for fixing, embedding, and/or permeabilizing the biological sample. In some embodiments, the kits contain reagents, such as enzymes and buffers for ligation and/or amplification, such as ligases and/or polymerases. In some aspects, the kit can also comprise any of the reagents described herein, e.g., wash buffer and ligation buffer. In some embodiments, the kits contain reagents for detection and/or sequencing, such as detectably labeled nucleotides, polymerases, or conjugates. In some embodiments, the kits optionally contain other components, for example nucleic acid primers, enzymes and reagents, buffers, nucleotides, modified nucleotides, reagents for additional assays.

VII. Opto-Fluidic Instruments for Analysis of Biological Samples

Provided herein is an instrument having integrated optics and fluidics modules (an "opto-fluidic instrument" or "opto-fluidic system") for detecting target molecules (e.g., nucleic acids, proteins, antibodies, etc.) in biological samples (e.g., one or more cells or a tissue sample) as described herein. In an opto-fluidic instrument, the fluidics module is configured to deliver one or more reagents (e.g., detectably labeled nucleotides, polymerases, or conjugates) to the biological sample and/or remove spent reagents therefrom. Additionally, the optics module is configured to illuminate the biological sample with light having one or more spectral emission curves (over a range of wavelengths) and subsequently capture one or more images of emitted light signals from the biological sample during one or more sequencing cycles (e.g., as described in Section III). In some embodiments, an in situ assay (e.g., sequencing-by-synthesis) disclosed herein can be performed using an automated instrument or system, e.g., an opto-fluidic instrument or system disclosed herein.

In various embodiments, the captured images may be processed in real time and/or at a later time to determine the presence of the one or more target molecules in the biological sample, as well as three-dimensional position information associated with each detected target molecule. Additionally, the opto-fluidics instrument includes a sample module configured to receive (and, optionally, secure) one or more biological samples. In some instances, the sample module includes an X-Y stage configured to move the biological sample along an X-Y plane (e.g., perpendicular to an objective lens of the optics module).

In various embodiments, the opto-fluidic instrument is configured to analyze one or more target molecules (e.g., any of the analytes described in Section III) in their naturally occurring place (i.e., in situ) within the biological sample. For example, an opto-fluidic instrument may be an in-situ analysis system used to analyze a biological sample and detect target molecules (e.g., analytes) including but not limited to DNA, RNA, proteins, antibodies, and/or the like.

An opto-fluidic instrument that can be used for in situ target molecule detection via base-by-base sequencing (e.g., sequencing of an identifier sequence such as a barcode sequence) and/or other imaging or target molecule detection technique. That is, for example, an opto-fluidic instrument may include a fluidics module that includes fluids needed for establishing the experimental conditions required for the probing of target molecules in the sample. Further, such an opto-fluidic instrument may also include a sample module configured to receive the sample, and an optics module including an imaging system for illuminating (e.g., exciting one or more fluorescently labeled nucleotides within the sample) and/or imaging light signals received from the sample. The in-situ analysis system may also include other ancillary modules configured to facilitate the operation of the opto-fluidic instrument, such as, but not limited to, cooling systems, motion calibration systems, etc.

Figure 5:
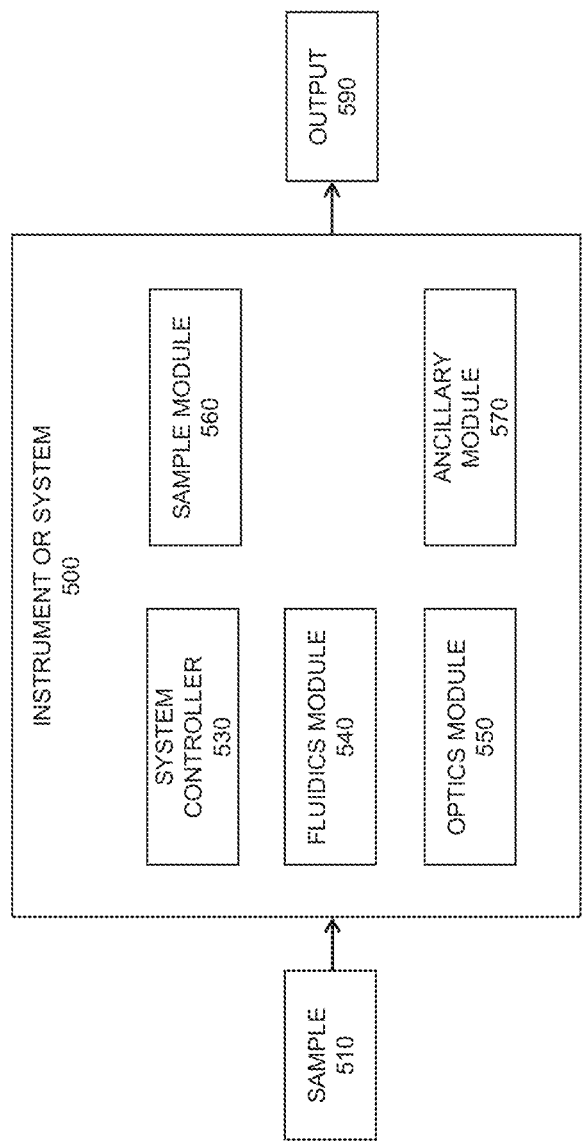
FIG. 5 is an example workflow of analysis of a biological sample (e.g., a cell or tissue sample) using an opto-fluidic instrument, according to various embodiments.

FIG. 5 shows an example workflow of analysis of a biological sample 510 (e.g., cell or tissue sample) using an opto-fluidic instrument or system 500, according to various embodiments. In various embodiments, the sample 510 can be a biological sample (e.g., a tissue) that includes molecules such as DNA, RNA, proteins, antibodies, etc. For example, the sample 510 can be a sectioned tissue that is treated to access the RNA thereof for probe hybridization and sequencing described herein (e.g., in Section III).

In various embodiments, the sample 510 may be placed in the opto-fluidic instrument or system 500 for analysis and detection of the molecules in the sample 510. In various embodiments, the opto-fluidic instrument or system 500 can be a system configured to facilitate the experimental conditions conducive for the detection of the target molecules. For example, the opto-fluidic instrument or system 500 can include a fluidics module 540, an optics module 550, a sample module 560, and an ancillary module 570, and these modules may be operated by a system controller 530 to create the experimental conditions for the base-by-base sequencing of nucleic acid molecules in the sample 510, as well as to facilitate the imaging of the sample (e.g., by an imaging system of the optics module 550). In various embodiments, the various modules of the opto-fluidic instrument or system 500 may be separate components in communication with each other, or at least some of them may be integrated together.

In various embodiments, the sample module 550 may be configured to receive the sample 510 into the opto-fluidic instrument or system 500. For instance, the sample module 560 may include a sample interface module (SIM) that is configured to receive a sample device (e.g., cassette) onto which the sample 510 can be deposited. That is, the sample 510 may be placed in the opto-fluidic instrument or system 500 by depositing the sample 510 (e.g., the sectioned tissue) on a sample device that is then inserted into the SIM of the sample module 560. In some instances, the sample module 560 may also include an X-Y stage onto which the SIM is mounted. The X-Y stage may be configured to move the SIM mounted thereon (e.g., and as such the sample device containing the sample 510 inserted therein) in perpendicular directions along the two-dimensional (2D) plane of the opto-fluidic instrument or system 500.

The experimental conditions that are conducive for the detection of the molecules in the sample 510 may depend on the target molecule detection technique that is employed by the opto-fluidic instrument or system 500. For example, in various embodiments, the opto-fluidic instrument or system 500 can be a system that is configured to detect molecules (e.g., by detecting nucleotides incorporated into extending sequencing primers using an identifier sequence as a template) in the sample 510.

In various embodiments, the fluidics module 540 may include one or more components that may be used for storing the reagents, as well as for transporting said reagents to and from the sample device containing the sample 510. For example, the fluidics module 540 may include reservoirs configured to store the reagents, as well as a waste container configured for collecting the reagents (e.g., and other waste) after use by the opto-fluidic instrument or system 500 to analyze and detect the molecules of the sample 510. Further, the fluidics module 540 may also include pumps, tubes, pipettes, etc., that are configured to facilitate the transport of the reagent to the sample device (e.g., and as such the sample 510). For instance, the fluidics module 540 may include pumps ("reagent pumps") that are configured to pump washing/stripping reagents to the sample device for use in washing/stripping the sample 510 (e.g., as well as other washing functions such as washing an objective lens of the imaging system of the optics module 550).

In various embodiments, the ancillary module 570 can be a cooling system of the opto-fluidic instrument or system 500, and the cooling system may include a network of coolant-carrying tubes that are configured to transport coolants to various modules of the opto-fluidic instrument or system 500 for regulating the temperatures thereof. In such cases, the fluidics module 540 may include coolant reservoirs for storing the coolants and pumps (e.g., "coolant pumps") for generating a pressure differential, thereby forcing the coolants to flow from the reservoirs to the various modules of the opto-fluidic instrument or system 500 via the coolant-carrying tubes. In some instances, the fluidics module 540 may include returning coolant reservoirs that may be configured to receive and store returning coolants, i.e., heated coolants flowing back into the returning coolant reservoirs after absorbing heat discharged by the various modules of the opto-fluidic instrument or system 500. In such cases, the fluidics module 540 may also include cooling fans that are configured to force air (e.g., cool and/or ambient air) into the returning coolant reservoirs to cool the heated coolants stored therein. In some instance, the fluidics module 540 may also include cooling fans that are configured to force air directly into a component of the opto-fluidic instrument or system 500 so as to cool said component. For example, the fluidics module 540 may include cooling fans that are configured to direct cool or ambient air into the system controller 530 to cool the same.

As discussed above, the opto-fluidic instrument or system 500 may include an optics module 550 which include the various optical components of the opto-fluidic instrument or system 500, such as but not limited to a camera, an illumination module (e.g., LEDs), an objective lens, and/or the like. The optics module 550 may include a fluorescence imaging system that is configured to image the fluorescence emitted by the detectably labeled nucleotides are incorporated in extending sequencing primers in the sample 510 after the detectable labels are excited by light from the illumination module of the optics module 550.

In some instances, the optics module 550 may also include an optical frame onto which the camera, the illumination module, and/or the X-Y stage of the sample module 560 may be mounted.

In various embodiments, the system controller 530 may be configured to control the operations of the opto-fluidic instrument or system 500 (e.g., and the operations of one or more modules thereof). In some instances, the system controller 530 may take various forms, including a processor, a single computer (or computer system), or multiple computers in communication with each other. In various embodiments, the system controller 530 may be communicatively coupled with data storage, set of input devices, display system, or a combination thereof. In some cases, some or all of these components may be considered to be part of or otherwise integrated with the system controller 530, may be separate components in communication with each other, or may be integrated together. In other examples, the system controller 530 can be, or may be in communication with, a cloud computing platform.

In various embodiments, the opto-fluidic instrument or system 500 may analyze the sample 510 and may generate the output 590 that includes indications of the presence of the target molecules in the sample 510. For instance, with respect to the example embodiment discussed above where the opto-fluidic instrument or system 500 employs a hybridization technique for detecting molecules, the opto-fluidic instrument or system 500 may cause the sample 510 to undergo successive sequencing cycles, where during the same sequencing cycle the sample is imaged to detect signals associated with nucleotide binding and/or incorporation events at at least some locations (e.g., locations where one or more genes in gene block 1 shown in FIG. 3 are present) in the sample 510, as well as absence of signals (e.g., absence of signals can be due to the use of unmodified nucleotides as dark bases or the absence of an agent capable of detecting the incorporated nucleotides) at other locations (e.g., locations where one or more genes in gene block 2 shown in FIG. 3 are present) in the sample. In such cases, the output 590 may include optical signatures (e.g., a codeword) specific to each identifier sequence (e.g., a barcode sequence), which allow the identification of the target molecules.

VIII. Terminology

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

The terms "polynucleotide," "polynucleotide," and "nucleic acid molecule", used interchangeably herein, refer to polymeric forms of nucleotides of any length, either ribonucleotides or deoxyribonucleotides. Thus, this term comprises, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups.

"Hybridization" as used herein may refer to the process in which two single-stranded polynucleotides bind non-covalently to form a stable double-stranded polynucleotide. In one aspect, the resulting double-stranded polynucleotide can be a "hybrid" or "duplex." "Hybridization conditions" typically include salt concentrations of approximately less than 1 M, often less than about 500 mM and may be less than about 200 mM. A "hybridization buffer" includes a buffered salt solution such as 5% SSPE, or other such buffers. Hybridization temperatures can be as low as 5° C., but are typically greater than 22° C., and more typically greater than about 30° C., and typically in excess of 37° C. Hybridizations are often performed under stringent conditions, i.e., conditions under which a sequence will hybridize to its target sequence but will not hybridize to other, non-complementary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the $T_m$ for the specific sequence at a defined ionic strength and pH. The melting temperature $T_m$ can be the temperature at which a population of double-stranded nucleic acid molecules becomes half dissociated into single strands. As indicated by standard references, a simple estimate of the $T_m$ value may be calculated by the equation, $T_m=81.5+0.41$ (% G+C), when a nucleic acid is in aqueous solution at 1 M NaCl (see e.g., Anderson and Young, Quantitative Filter Hybridization, in *Nucleic Acid Hybridization* (1985)). Other references (e.g., Allawi and SantaLucia, Jr., *Biochemistry*, 36:10581-94 (1997)) include alternative methods of computation which take structural and environmental, as well as sequence characteristics into account for the calculation of $T_m$.

In general, the stability of a hybrid is a function of the ion concentration and temperature. Typically, a hybridization reaction is performed under conditions of lower stringency, followed by washes of varying, but higher, stringency. Exemplary stringent conditions include a salt concentration of at least 0.01 M to no more than 1 M sodium ion concentration (or other salt) at a pH of about 7.0 to about 8.3 and a temperature of at least 25° C. For example, conditions of 5×SSPE (750 mM NaCl, 50 mM sodium phosphate, 5 mM EDTA at pH 7.4) and a temperature of approximately 30° C. are suitable for allele-specific hybridizations, though a suitable temperature depends on the length and/or GC content of the region hybridized. In one aspect, "stringency of hybridization" in determining percentage mismatch can be as follows: 1) high stringency: 0.1×SSPE, 0.1% SDS, 65° C.; 2) medium stringency: 0.2×SSPE, 0.1% SDS, 50° C. (also referred to as moderate stringency); and 3) low stringency: 1.0×SSPE, 0.1% SDS, 50° C. It is understood that equivalent stringencies may be achieved using alternative buffers, salts and temperatures. For example, moderately stringent hybridization can refer to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions can be conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C. Low stringency hybridization can refer to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M EDTA. Other suitable moderate stringency and high stringency hybridization buffers and conditions are described, for example, in Sambrook et al., Molecular Cloning: A Laboratory Manual, 2nd ed., Cold Spring Harbor Press, Plainview, N.Y. (1989); and Ausubel et al., Short Protocols in Molecular Biology, 4th ed., John Wiley & Sons (1999).

Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See M. Kanehisa, Nucleic Acids Res. 12:203 (1984).

A "primer" used herein can be an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers usually are extended by a DNA polymerase.

"Ligation" may refer to the formation of a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide.

"Sequencing," "sequence determination" and the like means determination of information relating to the nucleotide base sequence of a nucleic acid. Such information may include the identification or determination of partial as well as full sequence information of the nucleic acid. Sequence information may be determined with varying degrees of statistical reliability or confidence. In one aspect, the term includes the determination of the identity and ordering of a plurality of contiguous nucleotides in a nucleic acid. "High throughput digital sequencing" or "next generation sequencing" means sequence determination using methods that determine many (typically thousands to billions) of nucleic acid sequences in an intrinsically parallel manner, i.e. where DNA templates are prepared for sequencing not one at a time, but in a bulk process, and where many sequences are read out preferably in parallel, or alternatively using an ultra-high throughput serial process that itself may be parallelized. Such methods include but are not limited to pyrosequencing (for example, as commercialized by 454 Life Sciences, Inc., Branford, Conn.); sequencing by ligation (for example, as commercialized in the SOLiD™ technology, Life Technologies, Inc., Carlsbad, Calif.); sequencing by synthesis using modified nucleotides (such as commercialized in TruSeq™ and HiSeq™ technology by Illumina, Inc., San Diego, Calif; HeliScope™ by Helicos Biosciences Corporation, Cambridge, Ma.; and PacBio RS by Pacific Biosciences of California, Inc., Menlo Park, Calif.), sequencing by ion detection technologies (such as Ion Torrent™ technology, Life Technologies, Carlsbad, Calif); sequencing of DNA nanoballs (Complete Genomics, Inc., Mountain View, Calif.); nanopore-based sequencing technologies (for example, as developed by Oxford Nanopore Technologies, LTD, Oxford, UK), and like highly parallelized sequencing methods. "Multiplexing" or "multiplex assay" herein may refer to an assay or other analytical method in which the presence and/or amount of multiple targets, e.g., multiple nucleic acid target sequences, can be assayed simultaneously by using more than one probes, each of which has at least one different detection characteristic, e.g., fluorescence characteristic (for example excitation wavelength, emission wavelength, emission intensity, FWHM (full width at half maximum peak height), or fluorescence lifetime) or a unique nucleic acid or protein sequence characteristic.

The term "about" as used herein refers to the usual error range for the respective value readily known to the skilled person in this technical field. Reference to "about" a value or parameter herein comprises (and describes) embodiments that are directed to that value or parameter per se.

As used herein, the singular forms "a," "an," and "the" comprise plural referents unless the context clearly dictates otherwise. For example, "a" or "an" means "at least one" or "one or more."

Throughout the present disclosure, various aspects are presented in a range format. It should be understood that the description in range format is merely for convenience and brevity and should not be construed as an inflexible limitation on the scope of the present disclosure. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the present disclosure. The upper and lower limits of these smaller ranges may independently be comprised in the smaller ranges, and are also encompassed within the present disclosure, subject to any specifically excluded limit in the stated range. Where the stated range comprises one or both of the limits, ranges excluding either or both of those comprised limits are also comprised in the present disclosure. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

EXEMPLARY EMBODIMENTS

Embodiment 1. A method of analyzing a biological sample, comprising:
  a) contacting the biological sample with a first probe and a second probe, wherein:
    the biological sample is a cell or tissue sample,
    the biological sample comprises a first analyte and a second analyte at a first location and a second location, respectively, in the biological sample,
    the first probe and the second probe directly or indirectly bind to the first analyte and the second analyte, respectively,
    the first probe or a product thereof comprises i) a first priming site for a first sequencing primer and ii) a first identifier sequence associated with the first analyte, and
    the second probe or a product thereof comprises i) a second priming site for a second sequencing primer and ii) a second identifier sequence associated with the second analyte;
  b) performing base-by-base sequencing of the first and second identifier sequences using the first and second sequencing primers, thereby generating a first signal code sequence and a second signal code sequence, each comprising signal codes each corresponding to a signal (an ON signal), an absence of signal (an OFF signal), or a combination thereof detected in sequential cycles at the first location and the second location, respectively,
    wherein in one or more of the sequential cycles, an ON signal is detected at the first location and an OFF signal is detected at the second location; and
  c) detecting the first and second identifier sequences in the biological sample based on the first and a second signal code sequences.

Embodiment 2. The method of Embodiment 1, wherein the first and second analytes are the same or different.

Embodiment 3. The method of Embodiment 1 or 2, wherein the first and second identifier sequences are different.

Embodiment 4. The method of any of Embodiments 1-3, wherein the first and second identifier sequences comprise analyte sequences or complements thereof.

Embodiment 5. The method of any of Embodiments 1-4, wherein the first and second identifier sequences comprise barcode sequences or complements thereof assigned to the first and second analytes, respectively.

Embodiment 6. The method of Embodiment 5, comprising assigning a first barcode sequence to the first analyte and a second barcode sequence to the second analyte.

Embodiment 7. The method of Embodiment 6, wherein a nucleotide in the first barcode sequence detected in a particular cycle corresponds to a signal code comprising an ON signal, and the corresponding nucleotide in the second barcode sequence detected in the particular cycle corresponds to a signal code comprising an OFF signal.

Embodiment 8. The method of Embodiment 7, wherein the nucleotide in the first barcode sequence detected in the particular cycle corresponds to ON signal(s) only, and the corresponding nucleotide in the second barcode sequence detected in the particular cycle corresponds to OFF signal(s) only.

Embodiment 9. The method of any of Embodiments 6-8, wherein one or more pairs of corresponding nucleotides in the first and second barcode sequences to be detected in the same cycle are chosen to reduce optical crowding of signals detected in the cycle.

Embodiment 10. The method of any of Embodiments 1-9, wherein the base-by-base sequencing is performed by contacting the biological sample with nucleotides in sequential cycles,
  wherein in each cycle a complex is formed, the complex comprising i) the first or second sequencing primer or an extension product thereof hybridized to the first or second priming site, respectively, ii) a polymerase, and iii) a cognate nucleotide that base pairs with a nucleotide in the first or second identifier sequence, and
  a signal (an ON signal) and/or an absence of signal (an OFF signal) associated with the cognate nucleotide and/or the polymerase in the complex is detected at a particular location in the biological sample, wherein the ON signal, the OFF signal, or a combination thereof corresponds to the base in the cognate nucleotide and the corresponding nucleotide in the first or second identifier sequence.

Embodiment 11. The method of any of Embodiments 1-10, wherein 25% or more of the nucleotides in the first and/or second identifier sequences correspond to OFF signals.

Embodiment 12. The method of Embodiment 11, wherein 40% or more, 45% or more, 50% or more, 55% or more, 60% or more, 65% or more, 70% or more, 75% or more, 80% or more, 85% or more, 90% or more, or 95% or more of the nucleotides in the first and/or second identifier sequences are assigned to correspond to OFF signals.

Embodiment 13. The method of any of Embodiments 1-12, wherein multiple different identifier sequences are detected in the biological sample, and each different identifier sequence is detected at one or more locations in the biological sample.

Embodiment 14. The method of Embodiment 13, wherein 50% or more of the different identifier sequences each comprises 50% or more of the nucleotides in the identifier sequence that correspond to OFF signals.

Embodiment 15. The method of Embodiment 13 or 14, wherein 80% or more of the different identifier sequences each comprises 80% or more of the nucleotides in the identifier sequence that correspond to OFF signals.

Embodiment 16. The method of any of Embodiments 1-15, wherein the signal codes each corresponds to a signal of a first color, a signal of a second color, a signal of a third color, or absence of signal, and wherein the first, second, and third colors are different.

Embodiment 17. The method of any of Embodiments 1-15, wherein the signal codes each corresponds to a signal of a first color, a signal of a second color, a combination of signals of the first and second colors, or absence of signal, wherein the first and second colors are different.

Embodiment 18. The method of any of Embodiments 1-15, wherein the signal codes each corresponds to a combination of a signal (an ON signal) and/or absence of signal (an OFF signal), wherein the combination of ON and/or OFF signals is detected in two or more imaging steps.

Embodiment 19. The method of any of Embodiments 1-18, further comprising detecting the first and second analytes in the biological sample based on detecting the first and second identifier sequences.

Embodiment 20. The method of any of Embodiments 1-19, wherein the first identifier sequence is a first barcode sequence or a complement thereof, and the second identifier sequence is a second barcode sequence or a complement thereof.

Embodiment 21. The method of Embodiment 20, wherein: the first barcode sequence identifies the first analyte, and/or the second barcode sequence identifies the second analyte.

Embodiment 22. The method of Embodiment 20 or 21, wherein: the first probe is provided in a first plurality of probes that directly or indirectly bind to the first analyte, the first plurality of probes collectively comprise a first combination of barcode sequences, and the first combination of barcode sequences identifies the first analytes, and/or the second probe is provided in a second plurality of probes that directly or indirectly bind to the second analyte, the second plurality of probes collectively comprise a second combination of barcode sequences, and the second combination of barcode sequences identifies the second analytes.

Embodiment 23. The method of any of Embodiments 1-19, wherein the first and second analytes comprise nucleic acid sequences, the first identifier sequence is a sequence of the first analyte or a complement thereof, and the second identifier sequence is a sequence of the second analyte or a complement thereof.

Embodiment 24. The method of any of Embodiments 1-23, wherein the base-by-base sequencing comprises:
  using a polymerase that is fluorescently labeled and one or more nucleotides that are not fluorescently labeled;
  using a polymerase-nucleotide conjugate comprising a fluorescently labeled polymerase linked to a nucleotide moiety that is not fluorescently labeled; or
  using a multivalent polymer-nucleotide conjugate comprising a polymer core, multiple nucleotide moieties, and one or more fluorescent labels.

Embodiment 25. The method of Embodiment 24, wherein a cognate nucleotide is not incorporated by the polymerase into the first or second sequencing primer, or an extension product thereof.

Embodiment 26. The method of Embodiment 24, wherein incorporation of a cognate nucleotide by the polymerase into the first or second sequencing primer or an extension product thereof is attenuated or inhibited.

Embodiment 27. The method of any of Embodiments 1-23, wherein the base-by-base sequencing comprises contacting the biological sample with a nucleotide mix comprising a fluorescently labeled nucleotide and a nucleotide that is not fluorescently labeled.

Embodiment 28. The method of Embodiment 27, wherein a cognate nucleotide is incorporated by a polymerase into the first or second sequencing primer or an extension product thereof, and the cognate nucleotide is or is not fluorescently labeled.

Embodiment 29. The method of Embodiment 27 or 28, wherein the base-by-base sequencing comprises:
  contacting the biological sample with a first nucleotide mix in which nucleotides comprising a first base are not detectably labeled, whereas nucleotides comprising bases other than the first base are each labeled with one or more detectably labels, and
  contacting the biological sample with a subsequent nucleotide mix in which nucleotides comprising a subsequent base are not detectably labeled, whereas nucleotides comprising bases other than the subsequent base are each labeled with one or more detectably labels,
  wherein the subsequent base is the same as the first base, optionally wherein the first and subsequent bases are A, T, C, or G.

Embodiment 30. The method of Embodiment 27 or 28, wherein the base-by-base sequencing comprises:
  contacting the biological sample with a first nucleotide mix in which nucleotides comprising a first base are not detectably labeled, whereas the other nucleotides in the first nucleotide mix are each labeled with one or more detectably labels, and
  contacting the biological sample with a subsequent nucleotide mix in which nucleotides comprising a subsequent base are not detectably labeled, whereas the other nucleotides in the subsequent nucleotide mix are each labeled with one or more detectably labels,
  wherein the subsequent base is different from the first base.

Embodiment 31. The method of Embodiment 30, wherein the biological sample is contacted with two or more of the following nucleotide mixes in sequential cycles in any order:
  nucleotide mix 1 in which nucleotides comprising G are not detectably labeled, whereas nucleotides comprising A, C, or T are detectably labeled;
  nucleotide mix 2 in which nucleotides comprising T are not detectably labeled, whereas nucleotides comprising A, C, or G are detectably labeled;
  nucleotide mix 3 in which nucleotides comprising C are not detectably labeled, whereas nucleotides comprising A, G, or T are detectably labeled; and
  nucleotide mix 4 in which nucleotides comprising A are not detectably labeled, whereas nucleotides comprising G, C, or T are detectably labeled.

Embodiment 32. The method of Embodiment 31, wherein independent of one another, each nucleotide mix is contacted with the biological sample in one or more cycles, wherein the cycles are consecutive or nonconsecutive.

Embodiment 33. The method of Embodiment 31 or 32, wherein independent of one another, in each nucleotide mix, the detectably labeled nucleotides comprise:
  i) fluorescent labels of three different colors, one for each of the three bases;
  ii) fluorescent labels of two different colors, one each for two of the three bases, wherein nucleotides comprising the remaining base are labeled with both colors; or
  iii) fluorescent labels of the same color, wherein fluorescent labels on nucleotides comprising one of the three bases are configured to be cleaved, and nucleotides comprising another one of the three bases are configured to be labeled with the fluorescent label.

Embodiment 34. The method of any of Embodiments 1-33, wherein the first priming site and the second priming site are different, and the method comprises:
  b1) hybridizing the first sequencing primer to the first priming site and performing base-by-base sequencing to generate an extension product of the first sequencing primer and the first signal code sequence;
  b2) removing, cleaving, or blocking the extension product of the first sequencing primer in b1); and
  b3) hybridizing the second sequencing primer to the second priming site and performing base-by-base sequencing to generate an extension product of the second sequencing primer and the second signal code sequence.

Embodiment 35. The method of Embodiment 34, wherein probes or products thereof for a first plurality of analytes share a common first priming site, and probes or products thereof for a second plurality of analytes share a common second priming site.

Embodiment 36. The method of Embodiment 35, wherein the second plurality of analytes comprises two or more different analytes that are different from two or more different analytes of the first plurality of analytes.

Embodiment 37. The method of any of Embodiments 1-36, wherein: in a), the biological sample is contacted with a plurality of probes each configured to directly or indirectly bind to a different analyte, and each probe or product thereof comprises a combination of different priming sites.

Embodiment 38. The method of Embodiment 37, wherein: the first probe or product thereof comprises a first combination of different priming sites comprising the first priming site, and/or the second probe or product thereof comprises a second combination of different priming sites comprising the second priming site.

Embodiment 39. The method of Embodiment 38, wherein: in a), the biological sample is contacted with a third probe that directly or indirectly binds to a third analyte, the third probe or product thereof comprises a third combination of different priming sites comprising the first priming site, the second priming site, and/or a third priming site.

Embodiment 40. The method of Embodiment 39, wherein any two or more of the first combination, the second combination, and the third combination share one or more common priming sites.

Embodiment 41. The method of any of Embodiments 37-40, comprising:
  b') contacting the biological sample with the first sequencing primer for base-by-base sequencing, thereby hybridizing the first sequencing primer to the first priming site in the first probe or product thereof and in one or more other probes or products thereof, and generating extension products of the first sequencing primer;
  b") removing, cleaving, or blocking the extension products of the first sequencing primer in b'); and
  b''') contacting the biological sample with the second sequencing primer for base-by-base sequencing, thereby hybridizing the second sequencing primer to the second priming site in the second probe or product thereof and in one or more other probes or products thereof, and generating extension products of the second sequencing primer.

Embodiment 42. The method of Embodiment 41, wherein the base-by-base sequencing in b') is performed by:
  contacting the biological sample with nucleotides in sequential cycles, detecting signals associated with nucleotide incorporation or binding for each sequential cycle, and generating signal code sequences for a first plurality of analytes.

Embodiment 43. The method of Embodiment 41 or 42, wherein the base-by-base sequencing in b''') is performed by:
  contacting the biological sample with nucleotides in sequential cycles,
  detecting signals associated with nucleotide incorporation or binding for each sequential cycle, and
  generating signal code sequences for a second plurality of analytes.

Embodiment 44. The method of Embodiment 43, wherein the first plurality of analytes and the second plurality of analytes comprise one or more common analytes.

Embodiment 45. The method of Embodiment 43, wherein the first plurality of analytes and the second plurality of analytes do not comprise a common analyte.

Embodiment 46. The method of any of Embodiments 1-45, wherein each analyte is independently a nucleic acid analyte or non-nucleic acid analyte.

Embodiment 47. The method of any of Embodiments 1-46, wherein each probe is independently i) a primary probe that directly binds to its corresponding analyte, or ii) a probe that directly or indirectly binds to the primary probe.

Embodiment 48. The method of Embodiment 47, wherein the primary probe and the probe that directly or indirectly binds to the primary probe are independently selected from the group consisting of: a probe comprising a 3' or 5' overhang, optionally wherein the 3' or 5' overhang comprises one or more barcode sequences; a probe comprising a 3' overhang and a 5' overhang, optionally wherein the 3' overhang and the 5' overhang each independently comprises one or more barcode sequences; a circular probe; a circularizable probe or probe set; a probe or probe set comprising a split hybridization region configured to hybridize to a splint, optionally wherein the split hybridization region comprises one or more barcode sequences; and a combination thereof.

Embodiment 49. The method of any of Embodiments 1-48, wherein the product of each probe is a rolling circle amplification (RCA) product generated in situ in the biological sample.

Embodiment 50. The method of any of Embodiments 1-49, wherein in b), the base-by-base sequencing is performed in situ in the biological sample.

Embodiment 51. A method of analyzing a biological sample, comprising:
  a) contacting the biological sample with a first probe and a second probe, wherein:
    the biological sample is a cell or tissue sample,
    the biological sample comprises a first analyte and a second analyte at a first location and a second location, respectively, in the biological sample,
    the first probe and the second probe directly or indirectly bind to the first analyte and the second analyte, respectively,
    the first probe or a product thereof comprises i) a first priming site for a first sequencing primer and ii) a first identifier sequence associated with the first analyte, and
    the second probe or a product thereof comprises i) a second priming site for a second sequencing primer and ii) a second identifier sequence associated with the second analyte;
  b) performing base-by-base sequencing of the first identifier sequence using the first sequencing primer to generate signal codes detected in sequential cycles at the first location; and
  c) subsequently performing base-by-base sequencing of the second identifier sequence using the second sequencing primer to generate signal codes detected in additional sequential cycles at the second location;
  wherein in at least one or more of the sequential cycles in b) and the additional sequential cycles in c), an OFF signal is detected.

EXAMPLES

The following examples are included for illustrative purposes only and are not intended to limit the scope of the present disclosure.

Example 1: Dark Bases

This Example describes the use of a probe comprising a barcode to detect target genes in situ. The probe is designed in a way to significantly reduce optical crowding of fluorescent signals during multiple rounds of decoding. The probe design enables in situ detection of a large number of target genes in parallel by achieving dark cycles (no signal detected, e.g., by not detecting the nucleotide binding or incorporation events) for a majority of genes using sequencing-by-synthesis (SBS) or sequencing-by-binding (SBB). The probes used in this Example are configured to have one priming site to initiate sequencing in addition to a downstream barcode sequence per probe.

FIG. 2 depicts an exemplary probe and a rolling circle amplification (RCA) product thereof. The probe includes a sequence that is complementary to a sequence of the target analyte (e.g., nucleic acid such as an mRNA molecule) in a biological sample. The probe additionally comprises a priming site for hybridization to a sequencing primer and a downstream identifier sequence (e.g., barcode sequence). The barcode sequence corresponds to the analyte to which the probe is hybridized. Thus, identification of the barcode sequence by SBS or SBB permits decoding of the analytes.

The barcode sequence is designed in such a way that during SBS or SBB, one of the four nucleotides (e.g., A, T, G, and C) that is incorporated (SBS) or bound (SBB) to the nucleotide in the barcode sequence is not fluorescently labeled (e.g., dark base), while the other 3 nucleotides are fluorescently labeled. The three nucleotides are fluorescently labeled with three different colors, one for each base (e.g., 3-channel chemistry such as A-red, G-green, and T-blue). Alternatively, the three fluorescently labeled nucleotides may be labeled with two different colors, one each for two of the three bases, wherein the nucleotide comprising the remaining base is labeled with both colors (e.g., 2-channel chemistry such as A-red, G-green, and T-(red and green)). Alternatively, the three fluorescently labeled nucleotides may be labeled with the same color, wherein the fluorescent labels may be configured to be cleaved (e.g., 1-channel chemistry). In another example, two nucleotides are fluorescently labeled nucleotides and the two other nucleotides are not fluorescently labeled.

Further, the barcode sequence is designed such that the majority of the bases in the sequence are dark bases, where the majority of the bases in the barcode sequence pair with nucleotides that are not detectably labeled. Only a minority of the bases within the barcode sequence hybridize to fluorescently labeled nucleotides. For example, a barcode sequence may comprise nucleotides of which the vast majority (e.g., 80%) comprise the dark base G. In this instance, fluorescently labeled nucleotides A, C, and T will base pair with the cognate T, G, and A nucleotides within the barcode sequence. Cognate nucleotide C that is not fluorescently labeled will hybridize to the dark base G of the barcode sequence. In various cycles, the nucleotide designated as the dark base can be switched. In this instance, 80% of the nucleotides correspond to OFF signals only. Alternatively, 30% or more, 40% or more, 50% or more, 60% or more, 70% or more, 80% or more, or 90% or more of the nucleotides in the barcode sequence may correspond to OFF signals. The use of a probe with the barcode design as described above can reduce optical crowding of signals detected during multiple rounds of decoding. In some instances, a specified number of ON bits may be required in each code word. For example, each code word may comprise 5 ON bits/cycle corresponding to signals in at least 2, 3 or 4 different color channels to allow the an imaged feature to be distinguished from background fluorescent sources which will tend to emit in a single color channel.

A first probe and a second probe targeting a first and a second analyte at two different locations in the biological sample, are pooled. The probe mixture is then incubated with the biological sample (e.g., a cell culture sample or a thin tissue section sample) along with a hybridization buffer for hybridization to the target analytes in the sample. The sample is washed to remove excess or unbound probes and is incubated with a ligase (e.g., T4 DNA ligase) for ligation of the probes. The ligated product is incubated with a rolling-circle amplification (RCA) mixture containing a polymerase and dNTPs. After hybridization, ligation, and amplification, the RCA products are sequenced to decode the target analytes. For sequencing, the sample is incubated with a mixture containing a sequencing primer that binds to the priming site, a polymerase, and a mixture of nucleotides (e.g., labeled and unlabeled nucleotides). The first probe or the amplification product thereof comprises a first priming site for a first sequencing primer and a first barcode sequence such as one described above. The second probe or the amplification product thereof comprises a second priming site for a second sequencing primer and a second barcode sequence such as one described above.

Sequencing (e.g., SBS) of the first and second barcodes is initiated by incubating the sample with a nucleotide mixture in which nucleotides comprise one base (e.g., C) that is not fluorescently labeled (e.g., a dark base) while the other three bases are fluorescently labeled. As sequencing progresses, fluorescent signal codes are generated and imaged. A first signal code and a second signal code is generated, each corresponding to a signal (e.g., an ON signal) or the absence of a signal (e.g., an OFF signal), respectively at the two locations in the sample. Specifically, a nucleotide in the first barcode sequence detected in one sequencing cycle corresponds to a signal code comprising an ON signal, and the corresponding nucleotide in the second barcode sequence detected in the same cycle corresponds to a signal code comprising an OFF signal. In some instances, between two sequencing cycles, there is clain termination and termination reversal before next round. For instance, the nucleotide mixture may comprise reversibly-terminated nucleotides to limit SBS approaches to incorporation of a single nucleotide, and the reversible terminating group may be removed following each sequencing cycle prior to initiating the next sequencing cycle. The next round of decoding is performed where a subsequent nucleotide base pairs with its cognate nucleotide in the first and second barcode sequence. Signal codes are again generated wherein each signal code corresponds to either the absence of a signal (an OFF signal) or the presence of a signal of a first, second, third, or fourth color (an ON signal). In some aspects, the signal codes may correspond to a combination of any colors or absence thereof. The pairs of corresponding nucleotides in the first and second barcode sequences to be detected in the same cycle are specifically chosen to reduce optical crowding of signals detected in the cycles.

Multiple cycles of sequencing are performed in situ to completely decode the first and second barcode sequences while simultaneously reducing optical crowding of signals during the decoding rounds. As the barcode sequence corresponds to identity of the analyte to which the probe is hybridized, the signal codes generated during sequencing enable identification of the first and second analytes. In this manner, a large number of genes in a tissue or cell sample can be detected in parallel without optically crowding the sample.

Example 2: Use of Different Nucleotide Mixtures During Cycles of Decoding

This Example describes a method of reducing optical crowding of signals using the probes disclosed in Example 1 and different nucleotide mixtures. The different nucleotide mixtures are generated by altering the assignment of the dark base in each mixture and using a different mixture in each round of decoding. In this manner, the identity of the dark base is cycle-dependent. The method described herein offers the advantage of reducing optical crowding in situ without creating large stretches of the same base in the barcode sequence that may interfere with sequencing chemistry. In some cases, the dark base is a different nucleotide in each round, a given base need not be sacrificed to the dark channel, thus improving the analysis of the genes.

In this Example, probe design is similar to the one described in Example 1. The probe comprises a sequence complementary to the target analyte, a priming site to initiate sequencing, and a downstream barcode sequence. The barcode sequence designed in this Example contains more uniformity in the balance of bases. For instance, a barcode sequence can comprise equal proportions (25%) of A, T, C, and G bases. In some aspects, a barcode sequence can have any proportions or combinations of A, T, G, and C. The method disclosed in this Example uses different nucleotide mixtures in each round of decoding. The nucleotide mixture in each round contains a different dark base.

A first probe and a second probe targeting a first and a second analyte at two different locations in the biological sample, are pooled. The probe mixture is then incubated with the biological sample (e.g., a cell culture sample or a thin tissue section sample) along with a hybridization buffer for hybridization to the target analytes in the sample. The sample is washed to remove excess or unbound probes and is incubated with a ligase (e.g., T4 DNA ligase) for ligation of the probes. The ligated product is incubated with a rolling-circle amplification (RCA) mixture containing a polymerase and dNTPs. After hybridization, ligation, and amplification, the RCA products are sequenced to decode the target analytes. For sequencing, the sample is incubated with a mixture containing a sequencing primer that binds to the priming site, polymerase, and a specific mixture of nucleotides (e.g., labeled and unlabeled nucleotides) per cycle. The first probe or the amplification product thereof comprises a first priming site for a first sequencing primer and a first barcode sequence such as one described in Example 2. In some aspects, the second probe or product thereof comprises a second priming site for a second sequencing primer and a second barcode sequence such as one described in Example 2.

Sequencing (e.g., SBS) of the first and second barcodes is initiated by incubating the sample with a first nucleotide mixture, in which nucleotides comprising one base (e.g., a first base) not fluorescently labeled, whereas the other nucleotides in the first nucleotide mixture are each labeled with one or more fluorescent labels. For instance, the first nucleotide mixture contains nucleotides A-red label, C-green label, T-blue label, while nucleotide G is not labeled and is a dark base. As sequencing initiates, fluorescent signal codes generated are imaged. Signal codes are generated in such a way that a nucleotide in the first barcode sequence detected in the first cycle corresponds to a signal code comprising an ON signal, and the corresponding nucleotide in the second barcode sequence detected in the same cycle corresponds to a signal code comprising an OFF signal or a different colored ON signal. In some instances, the nucleotide mixture may comprise reversibly-terminated nucleotides to limit SBS approaches to incorporation of a single nucleotide, and the reversible terminating group may be removed following each sequencing cycle prior to initiating the next sequencing cycle and allow nucleotide incorporation. The next round of decoding is performed where the sample is washed and a second nucleotide mixture is incubated. The second nucleotide mixture contains a different dark base, whereas the other nucleotides in the mixture are each labeled with one or more fluorescent labels. The dark base that is not fluorescently labeled in the second round is different from the dark base used in the first nucleotide mixture in the previous round. For instance, the first nucleotide mixture contains nucleotides A-red label, C-green label, T-blue label, while nucleotide G is not labeled and is a dark base. The second nucleotide mixture contains nucleotides A-green label, C-blue label, G-red label, and T is not labeled and is a dark base. In this manner, the biological sample is incubated with different nucleotide mixtures in sequential cycles of decoding. Next, a third nucleotide mixture containing T-green label, C-blue label, G-red label, and A is a dark base is used. In each nucleotide mixture, the three fluorescently labeled nucleotides are labeled with three different colors, one for each base (e.g., 3-channel chemistry such as A-red, G-green, and T-blue). Alternatively, the three fluorescently labeled nucleotides may be with labeled with two different colors, one each or two of the three bases wherein the nucleotide comprising the remaining base is labeled with both colors (e.g., 2-channel chemistry such as A-red, G-green, and T-(red and green)). Alternatively, the three fluorescently labeled nucleotides may be labeled with the same color wherein fluorescent labels on nucleotides are configured to be cleaved (e.g., 1-channel chemistry).

Multiple cycles of sequencing are performed in situ to decode the first and second barcode sequences while simultaneously reducing optical crowding of signals during the decoding rounds. The first and second analytes are accordingly identified based on the signal codes generated while sequencing the first and second barcode sequences. In this manner, a large number of genes in a tissue or cell sample can be detected in parallel without creating large stretches of dark cycles.

Example 3: Method of Using a Common Sequencing Primer to Decode a Given Block of Different Analytes This Example describes a method of detecting multitude of genes in situ by sequentially decoding clusters of genes without optically crowding the biological sample. The method disclosed in this Example utilizes a relatively simple probe design comprising one priming site and barcode per probe, as described in Example 1 and 2. However, the priming site is common to a group of probes that hybridize to different analytes in the sample.

As illustrated in FIG. 3, a biological sample comprising six analytes (e.g., genes) at six different locations is analyzed. Six different probes targeting the six analytes are pooled, incubated with the biological sample (e.g., tissue sample or cell sample), and with hybridization buffer for hybridization to the target analytes. The sample is washed to remove excess or unbound probes and is incubated with a ligase (e.g., T4 DNA ligase) for ligation of the probes. The ligated product is incubated with a rolling-circle amplification (RCA) mixture containing a polymerase and dNTPs. After hybridization, ligation, and amplification, the RCA products are sequenced to decode the target analytes. For sequencing, the sample is incubated with a mixture containing a polymerase, a mixture of nucleotides (e.g., labeled and unlabeled nucleotides), and a sequencing primer-1. The sequencing primer-1 anneals to a common priming site present within a first group of probes hybridized to analytes 1, 2, and 3 (as shown in red in FIG. 3). Sequencing (e.g., SBS) of the first group of probes (Gene Block 1 in FIG. 3) is initiated by incubating the sample with a nucleotide mixture in which nucleotides comprise at least one base (e.g., C) that is not fluorescently labeled (e.g., a dark base) while the other bases are fluorescently labeled. As sequencing progresses, fluorescent signal codes corresponding to a combination of ON and OFF signals are generated and imaged in each decoding round (FIG. 2) as described in Examples 1 and 2. Once the barcode sequences within the probes of the first group or gene block 1 are sequenced, the sequencing primers-1 are removed via stripping or cleaving. In some instances, the sequencing primer extension product may also be blocked to prevent further nucleotide incorporation or binding. Next, the sample is washed and incubated with sequencing primer-2, which anneals to a common priming site present within a second group of probes hybridized to analytes 4, 5, and 6 (as shown in blue in FIG. 3). Sequencing (e.g., SBS) of the second group of probes (Gene block 2 in FIG. 3) is initiated by incubating the sample with a nucleotide mixture in which nucleotides comprise one base (e.g., A) that is not fluorescently labeled (e.g., a dark base) while the other three bases are fluorescently labeled. As sequencing progresses, fluorescent signal codes corresponding to a combination of ON and OFF signals are generated and imaged in each decoding round (FIG. 2) as described in Examples 1 and 2.

In this Example, decoding rounds are separated into blocks (e.g., block diagonal codes), where each block comprises a group of analytes bound to probes comprising a common priming site. In some instances, using block diagonal codes means only non-zero states are in blocks or submatrices. The block diagonal codes therefore may be densely packed within the locations of the genes. However, the method disclosed in this Example enables in situ detection of a large number of target genes by sequentially decoding clusters of genes without optically crowding the biological sample.

Example 4: Method of Using Multiple Sequencing Primers to Decode the Same Analyte This Example describes a method of detecting numerous genes in parallel without the constraints of block diagonal codes. The probes and methods described in this Example significantly reduce optical crowding of fluorescent signals while simultaneously optimizing the efficiency of encoding signal code sequences.

The probes used in this Example each comprise two or more priming sites and corresponding barcode sequences. As illustrated in FIG. 4, a probe hybridized to gene 1 comprises priming sites for sequencing primer 1 and 2, a probe hybridized to gene 2 comprises priming sites for sequencing primer 1 and 3, a probe hybridized to gene 3 comprises priming sites for sequencing primer 1 and 4, a probe hybridized to gene 4 comprises priming sites for sequencing primer 2 and 4, and a probe hybridized to gene 5 comprises priming sites for sequencing primer 2 and 4.

Each probe additionally comprises a corresponding barcode downstream of the priming site. Further, two different probes can have a common sequencing priming site and have a second unique priming site.

A biological sample comprising five different analytes (e.g., genes) at five different locations is analyzed. Five different probes targeting the five analytes are pooled, incubated with the biological sample (e.g., tissue sample or cell sample), and with hybridization buffer for hybridization to the target analytes. The sample is washed to remove excess or unbound probes and is incubated with a ligase (e.g., T4 DNA ligase) for ligation of the probes. The ligated products are incubated with a rolling-circle amplification (RCA) mixture containing a polymerase and dNTPs. After hybridization, ligation, and amplification, the RCA products are sequenced to decode the target analytes. For sequencing, the sample is incubated with a mixture containing a polymerase, a mixture of nucleotides (e.g., labeled and unlabeled nucleotides), and a mixture of sequencing primers (e.g., sequencing primers 1 as shown in FIG. 4). The mixture of sequencing primer 1 anneal to probes hybridized to genes 1, 2, and 3. Sequencing (e.g., SBS) is initiated by incubating the sample with a nucleotide mixture in which nucleotides comprise one base (e.g., G) that is not fluorescently labeled (e.g., a dark base) while the other three bases are fluorescently labeled. As sequencing progresses, fluorescent signal codes corresponding to a combination of ON and OFF signals are generated for genes 1, 2, and 3 and are imaged in each decoding round (FIG. 4) as described in Examples 1 and 2. No signals are acquired from barcodes downstream of the second priming sites for probes bound to genes 1, 2, and 3. Similarly, probes bound to genes 4 and 5 also remain dark. After multiple decoding rounds, the barcode sequence downstream of the sequencing primer 1 is decoded and the sequencing primer 1 is stripped off. The sample is then washed to remove the sequencing primers. The sample is then incubated with a subsequent mixture of sequencing primers (e.g., sequencing primer 2). The mixture of sequencing primer 2 anneals to probes hybridized to genes 1, 4, and 5. Similarly, sequencing is initiated, fluorescent signal codes corresponding to a combination of ON and OFF signals are generated at the locations of the genes 1, 4 and 5. After multiple decoding rounds, the barcode sequence downstream of the sequencing primer 2 is decoded and genes 1, 4, and partially identified. In this manner, multiple cycles of hybridization of a mixture of sequencing primers, sequencing, decoding, striping and re hybridization of a new mixture of sequencing primers are performed until all the barcodes within a given probe are decoded and the analytes are identified.

In this Example, large number of genes can be detected in parallel without the constraint of block diagonal codes. Using combinations of sequencing primers, the different sequencing primers can be mixed and matched for use in sequencing the genes, and this can allow increased complexity of the codes. As the barcodes within several genes are simultaneously decoded, the signal code sequences generated are spatially dispersed thus optimizing the efficiency of encoding the signals. The methods disclosed herein allow in situ detection of multitudes of genes in parallel without optically crowding the sample.

The present disclosure is not intended to be limited in scope to the particular disclosed embodiments, which are provided, for example, to illustrate various aspects of the present disclosure. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method of gene expression analysis, comprising:
a) providing a library of amplicons within a cell or tissue sample attached to a solid support-by chemical bonding, physical forces or a coating on the solid support, wherein the library of amplicons comprises a first amplicon comprising i) a first sequencing priming site and ii) a first identifier sequence, and a second amplicon comprising i) a second sequencing priming site different from the first sequencing priming site and ii) a second identifier sequence,
wherein the first and second identifier sequences comprise a sequence of a first analyte and a second analyte, respectively, in the cell or tissue sample;
b) using a first sequencing primer to sequence the first identifier sequence of the first amplicon,
wherein the sequencing comprises using a polymerase to incorporate a plurality of cognate nucleotides into the first sequencing primer or an extension product thereof;
c) removing, cleaving, or blocking the extension product of the first sequencing primer; and
d) using a second sequencing primer different from the first sequencing primer to sequence the second identifier sequence of the second amplicon,
wherein the sequencing comprises using a polymerase to incorporate an additional plurality of cognate nucleotides into the second sequencing primer or an extension product thereof;
wherein the plurality of cognate nucleotides and additional plurality of cognate nucleotides in b) and d), respectively, have the structure:

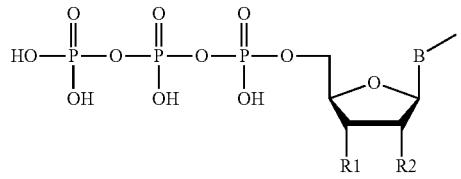

wherein B is selected from the group consisting of a purine base, a pyrimidine base, and a derivative of a purine or pyrimidine base, and B is coupled to a label via a linker; R1 is a terminator moiety; and R2 is H;
thereby using the sequenced first and second identifier sequences to identify an expressed transcript associated with a member of the library of amplicons.

2. The method of claim 1, wherein b) and d) each comprises contacting the cell or tissue sample with a nucleotide mix comprising a fluorescently labeled nucleotide and a nucleotide that is not fluorescently labeled.

3. The method of claim 1, wherein b) and d) each comprises contacting the cell or tissue sample with one of the following nucleotide mixes:
nucleotide mix 1 in which nucleotides comprising G are not detectably labeled, whereas nucleotides comprising A, C, or T are detectably labeled;
nucleotide mix 2 in which nucleotides comprising T are not detectably labeled, whereas nucleotides comprising A, C, or G are detectably labeled;
nucleotide mix 3 in which nucleotides comprising C are not detectably labeled, whereas nucleotides comprising A, G, or T are detectably labeled; or
nucleotide mix 4 in which nucleotides comprising A are not detectably labeled, whereas nucleotides comprising G, C, or T are detectably labeled.

4. The method of claim 3, wherein independent of one another, in each nucleotide mix, the detectably labeled nucleotides comprise:
i) fluorescent labels of three different colors, one for each of the three bases in the detectably labeled nucleotides;
ii) fluorescent labels of two different colors, one each for two of the three bases in the detectably labeled nucleotides, wherein nucleotides comprising the remaining base are labeled with both colors; or
iii) fluorescent labels of the same color, wherein fluorescent labels on nucleotides comprising one of the three bases in the detectably labeled nucleotides are configured to be cleaved, and nucleotides comprising another one of the three bases are configured to be labeled with the fluorescent label.

5. The method of claim 1, wherein the first sequencing priming site is assigned to the first analyte and the second sequencing priming site is assigned to the second analyte based on a decision rule designed to minimize a maximum predicted density of signals detected in each sequencing cycle of nucleotide incorporation of the sequencing in the cell or tissue sample.

6. The method of claim 5, wherein the decision rule uses expression data for the first analyte and the second analyte.

7. The method of claim 5, wherein the assigning comprises assignment based on expression data for the first analyte and the second analyte in clustered cell types.

8. The method of claim 7, wherein the expression data for the first analyte and the second analyte comprises spatial gene expression data, spatial protein expression data, single cell gene expression data, single cell protein expression data, or any combination thereof.

9. The method of claim 1, wherein:
prior to a), the cell or tissue sample is contacted with a first probe and a second probe that directly or indirectly binds to the first analyte and the second analyte, respectively.

10. The method of claim 9, further comprising ligating the first probe using the first analyte as template to form a first circularized template and ligating the second probe using the second analyte as template to form a second circularized template.

11. The method of claim 10, wherein the first circularized template and the second circularized template are each formed from a probe or probe set comprising a split hybridization region configured to hybridize to a splint.

12. The method of claim 9, wherein the first probe and the second probe are each a circular probe.

13. The method of claim 9, wherein the first probe is a first padlock probe comprising a sequence complementary to the first analyte in the arms of the first padlock probe and the second probe is a second padlock probe comprising a sequence complementary to the second analyte in the arms of the second padlock probe.

14. The method of claim 1, wherein the cell or tissue sample comprises a first plurality of amplicons that share a common first sequencing priming site and a second plurality of amplicons that share a common second sequencing priming site.

15. The method of claim 14, wherein:
the first plurality of amplicons comprises identifier sequences from two or more different analytes; and/or
the second plurality of amplicons comprises identifier sequences from two or more different analytes.

16. The method of claim 1, wherein the linker is a cleavable linker.

17. The method of claim 1, wherein b) and d) each comprises contacting the cell or tissue sample with a first nucleotide mix in a first sequencing cycle and contacting the cell or tissue sample with a second nucleotide mix in a second sequencing cycle, wherein the first nucleotide mix and the second nucleotide mix each comprises nucleotides of four different bases and nucleotides of three different bases are detectably labeled and nucleotides of the other base are not detectably labeled.

18. The method of claim 17, wherein the base of the nucleotides that are not fluorescently labeled in the second nucleotide mix is different from the base of the nucleotides that are not fluorescently labeled in the first nucleotide mix.

19. The method of claim 1, wherein multiple different identifier sequences are detected in the cell or tissue sample, and each different identifier sequence is detected at a plurality of locations in the cell or tissue sample.

20. The method of claim 1, wherein optical crowding is reduced compared to methods where the first and second identifier sequences are sequenced in the same series of sequencing cycles using the same sequencing primer.

\* \* \* \* \*